United States Patent [19]

Tatsuoka et al.

[11] Patent Number: 5,071,845
[45] Date of Patent: Dec. 10, 1991

[54] BENZOXAZEPINE DERIVATIVE

[75] Inventors: Toshio Tatsuoka, Nishinomiya; Kayoko Nomura; Makoto Shibata, both of Takatsuki, all of Japan

[73] Assignee: Suntory Limited, Osaka, Japan

[21] Appl. No.: 454,273

[22] Filed: Dec. 21, 1989

[30] Foreign Application Priority Data

Dec. 28, 1988 [JP] Japan .................................. 63-329103

[51] Int. Cl.⁵ ...................... A61K 31/53; C07D 521/00
[52] U.S. Cl. ....................................... 514/211; 540/490
[58] Field of Search ........................ 540/490; 514/211

[56] References Cited

U.S. PATENT DOCUMENTS

| | | | |
|---|---|---|---|
| 3,738,999 | 6/1973 | Krapcho et al. | 540/490 |
| 3,794,639 | 2/1974 | Krapcho et al. | 540/490 |
| 4,386,090 | 5/1983 | Moinet et al. | 568/808 |
| 4,431,851 | 2/1984 | Moinet et al. | 544/106 |
| 4,504,663 | 3/1985 | Moinet et al. | 546/144 |

FOREIGN PATENT DOCUMENTS

| | | | |
|---|---|---|---|
| 2496653 | 6/1982 | France | 544/106 |
| 63-83067 | 4/1988 | Japan | 544/373 |
| 63-83085 | 4/1988 | Japan | 544/368 |
| 63-183576 | 7/1988 | Japan | 546/198 |
| 64-68368 | 3/1989 | Japan | 544/238 |
| 1-106868 | 4/1989 | Japan | 544/377 |
| 1-28756 | 6/1989 | Japan | 544/372 |
| 1-157979 | 6/1989 | Japan | 544/373 |
| 1-34226 | 7/1989 | Japan | 544/360 |
| 1-193221 | 8/1989 | Japan | 544/333 |
| 1-502756 | 9/1989 | Japan | 544/362 |
| 1-502757 | 9/1989 | Japan | 544/361 |
| 1-249769 | 10/1989 | Japan | 544/361 |
| 1-249779 | 10/1989 | Japan | 544/333 |
| 1-311059 | 12/1989 | Japan | 544/12 |

OTHER PUBLICATIONS

Huckle et al., "The Preparation of Some 2,3-Dihydro-1,4-Benzoxazepin-5(4H)-ones and Related Compounds", *Journal of the Chemical Society* (Feb. 1965, pp. 1137–1141.

Primary Examiner—Robert T. Bond
Attorney, Agent, or Firm—Burns, Doane, Swecker & Mathis

[57] ABSTRACT

A benzoxazepine derivative suitable for use as a psychotropic composition having the formula:

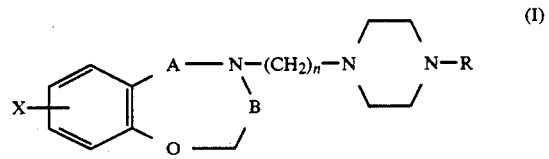

wherein A and B are both carbonyl groups, or one thereof represents a methylene group and the other a carbonyl group, R represents an aromatic group or a heterocyclic group, which may be substituted, X represents a hydrogen atom, a halogen atom, a $C_1$–$C_5$ lower alkyl group, a $C_1$–$c_5$ lower alkoxy group, a $C_7$–$C_9$ arylalkoxy group, a hydroxyl group, a nitro group, or an ester group, and n is an integer of 2 to 10 and salts thereof.

16 Claims, No Drawings

BENZOXAZEPINE DERIVATIVE

BACKGROUND OF THE INVENTION

1. Field of the Invention

The present invention relates to a benzoxazepine derivative having the formula:

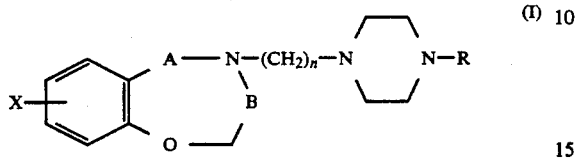

wherein A and B are both carbonyl groups, or one thereof represents a methylene group and the other a carbonyl group, R represents an aromatic group or a heterocyclic group which may be substituted, X represents a hydrogen atom, a halogen atom, preferably chlorine, bromine, fluorine, a $C_1$-$C_5$ lower alkyl group, preferably a $C_1$-$C_3$ alkyl group, a $C_1$-$C_5$ lower alkoxy group, preferably a $C_1$-$C_3$ alkoxy group, a $C_7$-$C_9$ arylalkoxy group, preferably a phenylalkoxy group, a hydroxyl group, a nitro group, or an ester group, and n is an integer of 2 to 10, preferably 2 to 8, more preferably 2 to 5, and salts thereof, and to a psycotropic composition containing the same as an active ingredient as well as the intermediate compounds for the preparation of the compound (I).

The novel benzoxazepine derivative having formula (I) of the present invention and its salts have a potent affinity for a serotonin receptor and an anticonflict activity, and are useful as drugs for psychotic disorders such as anxiety neurosis, phobic disorder, obsessive-compulsive disorder, psychosomatic disorder, post traumatic stress disorder, depressive neurosis, and as therapeutic drugs for diseases related to serotonergic neuron system, for example, eating disorder, climacteric disorder, and infantile autism.

2. Description of the Related Art

In the prior art, benzodiazepine type drugs, antipsychotic drugs and antidepressant drugs, are used as a therapeutic, for an anxiety neurosis, phobia, and obsessive-compulsive neurosis, but these drugs each have a problem with regard to the efficacy and side effects thereof.

Particularly, benzodiazepine type drugs are primarily used for an anxiety neurosis, but since a hypnotic action, muscle relaxing action, and a continuing dependence occur, there is an urgent need for the development of specific antianxiety drugs that do not have these side effects.

Various attempts have been made to solve these problems, and as a result, drugs having a selective affinity for a $5HT_{1A}$ subtype considered probably useful as antianxiety drugs with little side effects. Namely, buspirone, gepirone, ipsapirone and the like have been or are being developed.

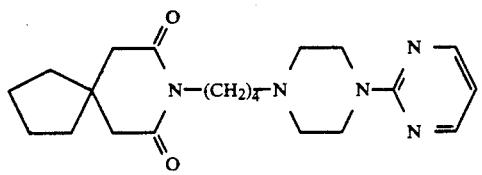
Buspirone

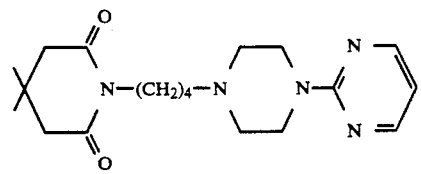
Gepirone

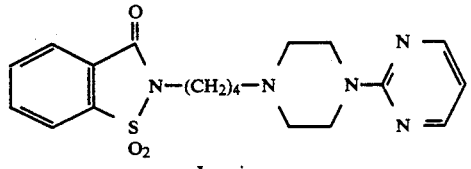
Ipsapirone

The above-mentioned buspirone, gepirone, and ipsapirone can partially alleviate various side effects, compared with benzodiazapine type drugs of the prior art, but can not be considered absolutely satisfactory, and there is a strong demand for antianxiety drugs having a high specificity with less side effects.

SUMMARY OF THE INVENTION

Accordingly, an object of the present invention is to solve the above-mentioned problems of the prior art and to provide a novel compound having a more potent affinity for a $5HT_{1A}$ receptor with a higher selectivity, which is usable as an antianxiety drug.

Another object of the present invention is to provide a novel compound useful for preparing the above-mentioned novel compound.

Other objects and advantages of the present invention will be apparent from the following description.

In accordance with the present invention, there are provided a benzoxazepine derivative having the formula (I) and a pharmacologically acceptable acid addition salt thereof, and a psychotropic composition containing the benzoxazepine derivative or the salt thereof as an active ingredient.

In accordance with the present invention, there is also provided an intermediate benzoxazepine derivative having the formula (II):

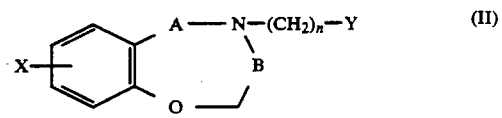

wherein A and B are both carbonyl groups, or one thereof represents a methylene group and the other a carbonyl group, Y represents a halogen atom, which may be substituted, X represents a hydrogen atom, a halogen atom, preferably chlorine, bromine, fluorine, a $C_1$-$C_5$ lower alkyl group, preferably a $C_1$-$C_3$ alkyl group, a $C_1$-$C_5$ lower alkoxy group, preferably a $C_1$-$C_3$ alkoxy group, a $C_7$-$C_9$ arylalkoxy group, preferably a phenylalkoxy group, a hydroxyl group, a nitro group, or an ester group, Y represents a halogen, preferably chlorine, bromine, fluorine, and n is an integer of 2 to 10, preferably 2 to 8, more preferably 2 to 5, and salts thereof.

This compound (II) can be prepared as follows.

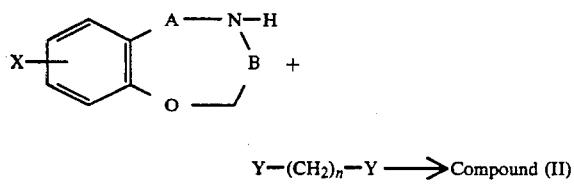

$$Y-(CH_2)_n-Y \longrightarrow \text{Compound (II)}$$

The resultant compound (II) can be condensed with a piperadine derivative to form the above-mentioned compound (I).

DESCRIPTION OF THE PREFERRED EMBODIMENT

The present inventors considered that it is most important to create a drug having a more potent affinity for a 5HT1A receptor with a higher selectivity, to develop usable antianxiety drugs not having the drawbacks mentioned above, and thus made an intensive study of this subject and, as a result, found that a novel benzoxazepine derivative, which is the compound of the present invention, has a very potent $5HT_{1A}$ receptor affinity as well as antianxiety activity as indexed by an anticonflict activity. The compound of the formula (I) according to the present invention can be prepared as described below. That is, in the compounds represented by the above formula (I), the compound represented by the following formula (Ia) wherein A is a carbonyl group and B is a methylene group:

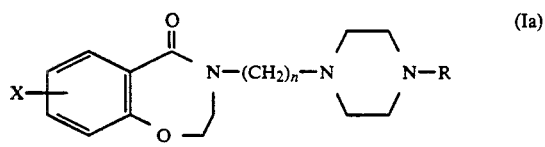

can be synthesized by reacting the compound (III) of the structure shown below, and obtained by the method or milar methods as described by G. S. Sidhu, G. Thyagarajan and U. T. Bhalerao, J. Chem. Soc. (C), 969 (1966):

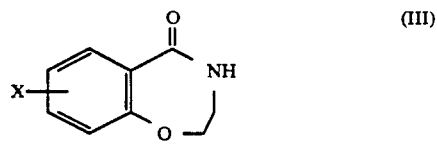

with, for example, a dibromoalkane, to obtain the compound (IV) of the following structure:

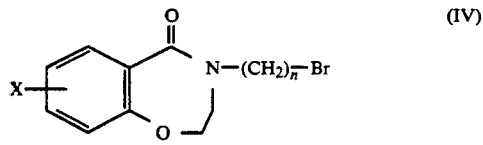

and then condensing same with a piperazine derivative in a conventional manner.

Also, in the compounds represented by the above formula (I), the compound (Ib) represented by the following formula (Ib) wherein A is a methylene group and B is a carbonyl compound:

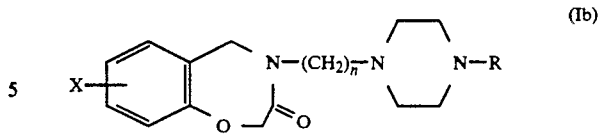

can be synthesized by reacting a compound (V) having the structure shown below, obtained according to the method or similar methods described in Kost, A. N., Stankevicius, A; Khim. Geterotsiki, Soedin, 7 (9) 1288 (1971), with a dibromoalkane to obtain a compound (VI) having the structure shown below:

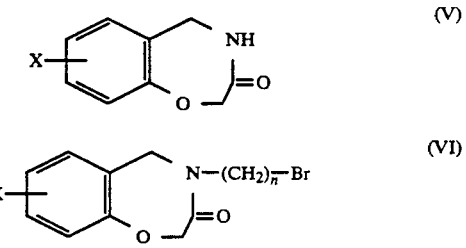

and then condensing same with a piperazine derivative.

Further, in the compounds represented by the above formula (I), the compound represented by the formula (Ic) wherein A and B are both carbonyl groups:

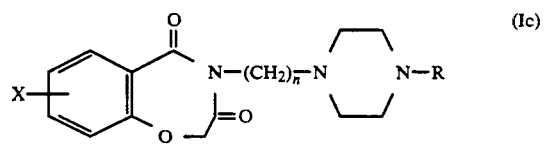

can be synthesized by reacting a compound (VII), obtained according to the method or similar methods described in A. Cattaneo, P. Galimberti, M. Melandri: Boll. Chim. Farm., 102, 541 (1963):

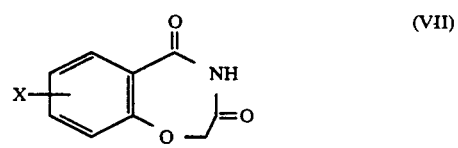

with d to obtain a compound (VIII) of the following formula:

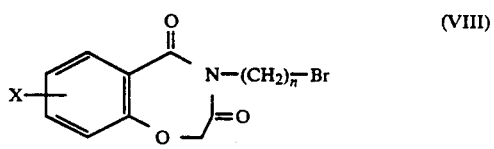

and then condensing same with a piperazine derivative. In the benzoxazepine derivative of the above formula (I) according to the present invention, R represents an aromatic group and a heterocyclic group which may be also substituted. Examples of such aromatic groups include $C_6$-$C_{10}$ aromatic groups, specifically, a phenyl group, a naphthyl group, and these aromatic groups may be substituted with halogen atoms (chlorine, bromine, fluorine, etc.), a hydroxyl group, a $C_1$-$C_6$ lower alkyl group, a $C_1$-$C_5$ lower alkoxy group, a $C_7$-$C_9$ arylalkoxy group a cyano group, an amino group, an amide group, a nitro group, a trifluoromethyl group an ester group (e.g., COO.C$_1$-C$_5$ lower alkyl group), etc. Further, the heterocyclic groups preferably include rings containing 1 to 3 nitrogen atoms in a 5 - 7-membered ring, specifically a pyridine ring, pyrimidinyl ring, pyrazinyl ring, imidazolyl ring, pyridazinyl ring, etc., and these heterocyclic rings may be also substituted with the substituents as mentioned above.

The novel benzoxazepine derivative represented by the above formula (I), and its pharmacologically acceptable salts (e.g. hydrochloride, nitrate, sulfate, oxalate, phosphate, methanesulfonate, hydrobromide, acetate, succinate, malonate, tartrate, maleate, fumarate, lactate, citrate), may be administered alone as such, but can be administered orally or parenterally in a desired dosage form (e.g. tablets, capsules, powders, liquid formulations, injections, suppositories) by mixing with pharmacologically acceptable conventional additives such as carriers, excipients, and vehicles. Examples of such diluents or carriers are polyvinyl pyrrolidone, gum arabic, gelatin, sorbitol, cyclodextrin, tragacanth gum, magnesium stearate, talc, polyethylene glycol, polyvinyl alcohol, silica, lactose, crystalline cellulose, sugar, starch, calcium phosphate, vegetable oil, calcium carboxymethyl cellulose, sodium lauryl sulfate, water, ethanol, glycerol, mannitol, and syrup.

The concentration of the compound of the formula (I) in such a pharmaceutical preparation is not particularly limited, but is generally about 1 to 100% by weight of the preparation, preferably about 10 to 100% by weight. Also, the dose thereof is not particularly limited, but is suitably 0.1 to 1000 mg/day/person, preferably 1 to 500 mg/day/person, and the dosage number is generally 1 to 4 times per day.

EXAMPLES

The present invention is now described with reference to, but is by no means limited to, the following Examples and Test Examples.

First, syntheses of the intermediate compounds are shown in Examples 1 to 18 and those of the active compounds are shown in Examples 19 to 93.

EXAMPLE 1

Synthesis of 4-(3-chloropropyl)-2,3,4,5-tetrahydro-1,4-benzoxazepin-5-one

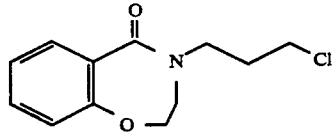

One gram of 2,3,4,5-tetrahydro-1,4-benzoxazepin-one was dissolved in 50 ml of dioxane and 5 ml of dimethyl sulfoxide, and 368 mg (1.5 equivalent) of 60% sodium hydride was added, followed by heating at 110° C. for one hour while stirring.

After cooling, 1.82 ml (3 equivalents) of 1-bromochloropropane was added to the reaction mixture obtained, and the mixture was stirred at room temperature for 17 hours. Dioxane was evaporated from the reaction mixture obtained, ice-water was added, and the mixture was extracted with ether. The ether extract was washed three times with aqueous sodium chloride, and dried over anhydrous magnesium sulfate. Then the ether solution was concentrated, and the residue was developed with hexane-ethyl acetate (6:4) by silica gel column chromatography to give 1.21 g of the desired compound (yield 83%).

EXAMPLE 2

Synthesis of 4-(3-bromopropyl)-2,3,4,5-tetrahydro-1,4-benzoxazepine-3,5-dione

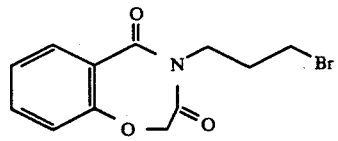

A 100 mg amount of 2,3,4,5-tetrahydro-1,4-benzoxazepine-3,5-dione was dissolved in 10 ml of dimethylformamide, and after ice-cooling, 0.172 ml (3 equivalents) of 1,3-dibromopropane and 27.1 mg (1.2 equivalents) of 60% sodium hydride were added, followed by stirring under ice-cooling for one hour.

The reaction mixture obtained was poured into an aqueous citric acid under ice-cooling and extracted with ether, and after washing with aqueous sodium chloride, the mixture was dried over anhydrous magnesium sulfate. The ether solution was concentrated, and the residue was developed with hexane-ethyl acetate (8:2) by silica gel column chromatography, to give 79.8 mg of the desired compound (yield 47%).

EXAMPLE 3

Synthesis of 4-(3-bromopropyl)-7-methoxy-2,3,4,5-tetrahydro-1,4-benzoxazepine-3,5-dione

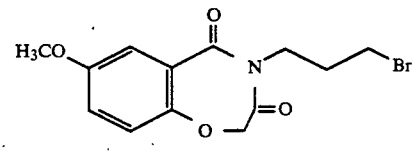

An 828 mg amount of 7-methoxy-2,3,4,5-tetrahydro-1,4benzoxazepine-3,5-dione was dissolved in 20 ml of dimethylformamide, 1.62 g (2 equivalents) of 1,3-dibromopropane were added, and after ice-cooling, 240 mg (1.5 equivalents) of 60% sodium hydride was added, followed by stirring under ice-cooling for one hour.

The reaction treatment and purification were conducted as in Example 2, to give 280 mg of the desired compound (yield 21.3%).

EXAMPLE 4

Synthesis of 4-(3-bromopropyl)-8-methyl-2,3,4,5-tetrahydro-1,4-benzoxazepine-3,5-dione

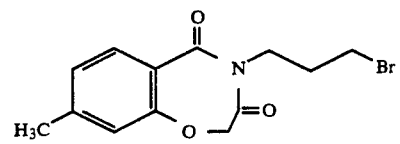

A 764 mg amount of 8-methyl-2,3,4,5-tetrahydro-1,4-benzoxazepine-3,5-dione was dissolved in 20 ml of dimethylformamide, 1.62 mg (2 equivalents) of 1,3-dibromopropane was added, and after ice-cooling, 240 mg (1.5 equivalents) of 60% sodium hydride was added, followed by stirring at room temperature for 30 minutes.

The reaction treatment and purification were conducted as in Example 2, to give 417 mg of the desired compound (yield 33.4%).

EXAMPLE 5

Synthesis of 4-(4-bromobutyl)-2,3,4,5-tetrahydro-1,4-benzoxazepin-5-one

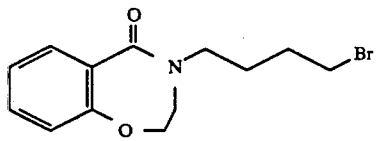

To a solution of 2 g of 2,3,4,5-tetrahydro-1,4-benzoxazepin-5-one dissolved in 100 ml of dioxane and 10 ml of dimethyl sulfoxide, 736 mg (1.5 equivalents) of 60% sodium hydride was added, and the mixture was heated at 110° C. for 30 minutes while stirring. The reaction mixture was ice-cooled, and then 4.49 ml (3 equivalents) of 1,4-dibromobutane was added, followed by stirring at room temperature for 2 hours.

The reaction treatment and purification were conducted as in Example 1, to give 2.56 g of the desired product (yield 70%).

EXAMPLE 6

Synthesis of 4-(4-bromobutyl)-2,3,4,5-tetrahydro-1,4-benzoxazepin-3-one

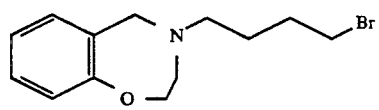

To a solution of 500 mg of 2,3,4,5-tetrahydro-1,4-benzoxazepin-3-one benzoxazepin-3-one dissolved in 50 ml of dioxane and 5 ml of dimethyl sulfoxide, 184 mg (1.5 equivalents) of 60% sodium hydride was added, and the mixture was heated at room temperature for 30 minutes while stirring. To the reaction mixture were added 1.12 ml (3 equivalents) of 1,4-dibromobutane and 5 ml of dimethylformamide, and the mixture was stirred at room temperature for 3 hours.

Then to the reaction mixture obtained was added ice-water, the mixture was extracted with ether, and the extract was washed with aqueous sodium chloride, followed by drying over anhydrous magnesium sulfate. The ether solution was concentrated, and the residue was developed with hexane-ethyl acetate (7:3) by silica gel column chromatography, to give 504 mg of the desired compound (yield 55.1%).

EXAMPLE 7

Synthesis of 4-(4-bromobutyl)-2,3,4,5-tetrahydro-1,4-benzoxazepine-3,5-dione

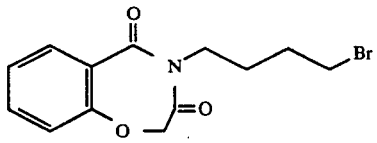

A 10 g amount of 2,3,4,5-tetrahydro-1,4-benzoxazepine-3,5-dione was dissolved in 100 ml of dimethylformamide, and after ice-cooling, 20.7 ml (3 equivalents) of 1,4-dibromobutane and 2.71 g (1.2 equivalents) of 60% sodium hydride were added, followed by stirring under ice-cooling for 1.5 hours.

The reaction treatment and purification were conducted as in Example 2, to give 10.3 g of the desired compound (yield 58%).

EXAMPLE 8

Synthesis of 4-(4-bromobutyl)-7-methoxy-2,3,4,5-tetrahydro-1,4-benzoxazepine-3,5-dione

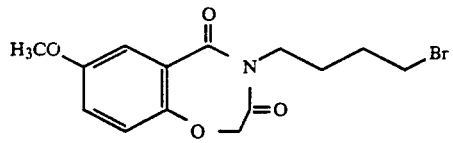

A 414 mg amount of 7-methoxy-2,3,4,5-tetrahydro-1,4-benzoxazepine-3,5-dione was dissolved in 10 ml of dimethylformamide, and after ice-cooling, 120 mg (1.5 equivalents) of 60% sodium hydride was added. After stirring for 10 minutes, 860 mg (2 equivalents) of 1,4-bromobutane was added, followed by stirring at room temperature for one hour.

The reaction treatment and purification were conducted as in Example 2, to give 345 mg of the desired product (yield 50.4%).

EXAMPLE 9

Synthesis of 8-chloro-4-(4-bromobutyl)-2,3,4,5-tetrahydro-1,4-benzoxazepine-3,5-dione

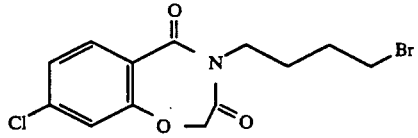

A 1.5 g amount of 8-chloro-2,3,4,5-tetrahydro1,4-benzoxazepine-3,5-dione was dissolved in 40 ml of dimethylformamide, and after ice-cooling, 1.30 ml (1.5 equivalents) of 1,4-dibromobutane and 340 mg (1.2 equivalents) of 60% sodium hydride were added, followed by stirring under ice-cooling for 30 minutes.

The reaction treatment and purification were conducted as in Example 2, to give 920 mg of the desired compound (yield 37%).

EXAMPLE 10

Synthesis of 4-(4-bromobutyl)-8-methyl-2,3,4,5-tetrahydro-1,4-benzoxazepine-3,5-dione

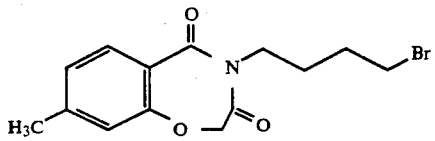

To a solution of 764 mg of 8-methyl-2,3,4,5-tetrahydro-1,4-benzoxazepine-3,5-dione dissolved in ml of dimethylformamide 1.72 g (2 equivalents) of 1,4-dibromobutane was added, and after ice-cooling, mg (1.5 equivalents) of 60% sodium hydride was added, followed by stirring at room temperature for 1.5 hours.

The reaction treatment and purification were conducted as in Example 2, to give 880 mg of the desired compound (yield 67.5%).

EXAMPLE 11

Synthesis of 8-methoxy-4-(4-bromobutyl)-2,3,4,5-tetrahydro-1,4-benzoxazepine-3,5-dione

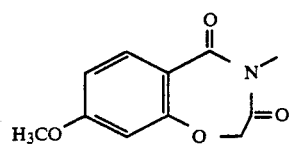

One gram of 8-methoxy-2,3,4,5-tetrahydro-1,4-benzoxazepine-3,5-dione was dissolved in 30 ml of dimethylformamide, and after ice-cooling, 1.77 ml (3 equivalents) of 1,4-dibromobutane and 232 mg (1.2 equivalents) of 60% sodium hydride were added, followed by stirring under ice-cooling for 1.5 hours.

The reaction treatment and purification were conducted as in Example 2, to give 1.25 g of the desired compound (yield 76%).

EXAMPLE 12

Synthesis of 6-methoxy-4-(4-bromobutyl)-2,3,4,5-tetrahydro-1,4-benzoxazepine-3,5-dione

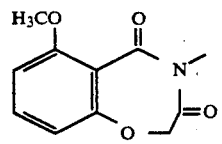

A 204 mg amount of 6-methoxy-2,3,4,5-tetrahydro-1,4-benzoxazepine-3,5-dione was dissolved in 20 ml of dimethylformamide, and after ice-cooling, 0.361 mg (3 equivalents) of 1,4-dibromobutane and 47.4 mg (1.2 equivalents) of 60% sodium hydride were added, followed by stirring under ice-cooling for 1.5 hours.

The reaction treatment and purification were conducted as in Example 2, to give 117 mg of the desired compound (yield 35%).

EXAMPLE 13

Synthesis of 6-benzyloxy-4-(4-bromobutyl)-2,3,4,5-tetrahydro-1,4-benzoxazepine-3,5-dione

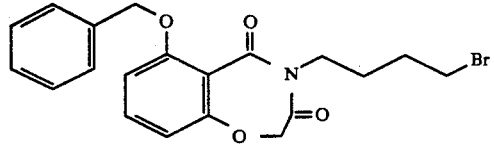

A 410 mg amount of 6-benzyloxy-2,3,4,5-tetrahydro-1,4-benzoxazepine-3,5-dione was dissolved in 40 ml of dimethylformamide, and after ice-cooling, 0.265 ml (1.5 equivalents) of 1,4-dibromobutane and 69.5 mg (1.2 equivalents) of 60% sodium hydride were added, followed by stirring under ice-cooling for one hour.

The reaction treatment and purification were conducted as in Example 2, to give 450 mg of the desired compound (yield 74%).

EXAMPLE 14

Synthesis of 7-nitro-4-(4-bromobutyl)-2,3,4,5-tetrahydro-1,4-benzoxazepine-3,5-dione

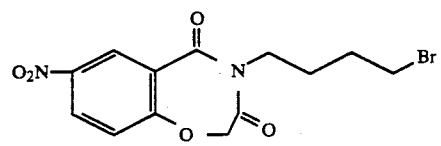

A 56.3 mg amount of 7-nitro-2,3,4,5-tetrahydro-1,4-benzoxazepine-3,5-dione was dissolved in 10 ml of dimethylformamide, and after ice-cooling, 0.0927 ml (3 equivalents) of 1,4-dibromobutane and 12.2 mg (1.2 equivalents) of 60% sodium hydride were added, followed by stirring at room temperature for 2 hours under ice-cooling.

The reaction treatment and purification were conducted as in Example 2, to give 16.4 mg of the desired compound (yield 18%).

EXAMPLE 15

Synthesis of 7-methoxycarbonyl-4-(4-bromobutyl)-2,3,4,5-tetrahydro-1,4-benzoxazepine-3,5-dione

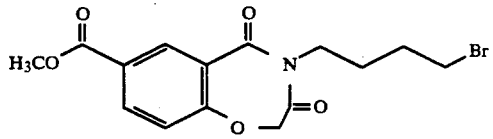

A 125 mg amount of 7-methoxycarbonyl-2,3,4,5-tetrahydro-1,4-benzoxaepine-3,5-dione was dissolved in 10 ml of dimethylformaide, and, after ice-cooling, 0.193 ml (3 equivalents) of 1,4-dibromobutane, and 25.3 mg (1.2 equivalents) of 60% sodium hydride were added, followed by stirring under ice-cooling for 1 hour.

the reaction treatment and purification were conducted as in Example 2, to give 124 mg of the desired compound (yield 63%).

EXAMPLE 16

Synthesis of 4-(5-bromopentyl)-2,3,4,5-tetrahydro-1,4-benzoxaepine-3,5-dione

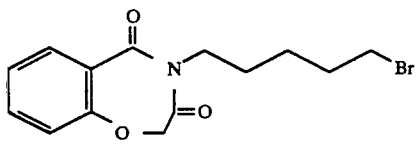

A 300 mg amount of 2,3,4,5-tetrahydro-1,4-benzoxaepine-3,5-dione was dissolved in 30 ml of dimethylforamide, and after ice-cooling, 0.693 ml (3 equivalents) of 1,5-dibromopentane and 81.4 mg (1.2 equivalents) of 60% sodium hydride were added, followed by stirring under ice-cooling for 30 minutes.

The reaction treatment and purification were conducted as in Example 2, to give 238 mg of the desired compound (yield 43%).

EXAMPLE 17

Synthesis of 4-(5-bromopentyl)-7-methoxy-2,3,4,5-tretrahydro-1,4-benzoxazepine-3,5-dione

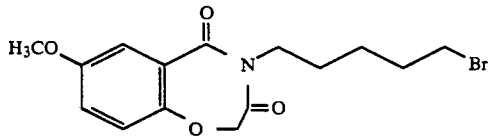

A 621 mg amount of 7-methoxy-2,3,4,5-tetrahydro-1,4-benzoxazepine-3,5-dione was dissolved in 10 ml of dimethylformamide, and 1.38 g (2 equivalents) of 1,5-bromopentane were added, and after ice-cooling, 180 mg (1.5 equivalents) of 60% sodium hydride was added, followed by stirring at room temperature for 4 hours.

The reaction treatment and purification were conducted as in Example 2, to give 396 mg of the desired compound (yield 37.1%).

EXAMPLE 18

Synthesis of 4-(5-bromopentyl)-8-methyl-2,3,4,5-tetrahydro-1,4-benzoxazepine-3,5-dione

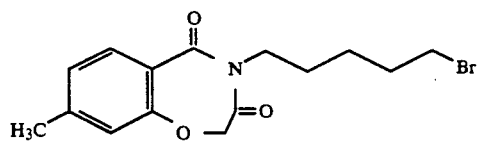

A 764 mg amount of 8-methyl-2,3,4,5-tetrahydro-1,4-benzoxazepine-3,5-dione was dissolved in 20 ml of dimethylformamide, and 2.07 g (2 equivalents) of 1,5-dibromopentane was added, and after ice-cooling, 240 mg (1.5 equivalents) of 60% sodium hydride was added, followed by stirring at room temperature for 30 minutes.

The reaction treatment and purification were conducted as in Example 2, to give 680 mg of the desired compound (yield 50.0%).

The physical data of the compounds obtained in the above-mentioned Examples 1 to 18 is shown in Table 1.

TABLE 1

| Example | m.p. | IR (cm$^{-1}$) | NMR ($\delta$ ppm) | Mass |
|---|---|---|---|---|
| 1 | 73–75° C. | 2930, 2850<br>1635, 1600<br>1470, 1440<br>1410, 1350<br>1310, 1300<br>1280, 1205<br>1130, 1100<br>1035, 970<br>940, 860<br>800, 780<br>760, 700 | 2.17(quintett, 2H, J=6.6Hz),<br>3.55(t, 2H, J=5.3Hz), 3.65<br>(t, 2H, J=6.6Hz), 3.75(t,<br>2H, J=6.6Hz), 4.39(t, 2H,<br>J=5.3Hz), 7.01(d, 1H,<br>J=7.3Hz), 7.16(t, 1H,<br>J=7.3Hz), 7.42(dt, 1H,<br>J=2.0Hz & 7.3Hz), 7.79(dd,<br>1H, J=2.0Hz & 7.3Hz) | calcd. 239.0712<br>obsd. 239.0732<br>(2.0) |
| 2 | 59–60° C. | 2950, 2900<br>1705, 1660<br>1640, 1600<br>1480, 1450<br>1370, 1320<br>1235, 1210<br>1125, 1105<br>1050, 1005<br>815, 780<br>760, 695 | 2.55(quintett, 2H, J=6.8Hz)<br>3.44(t, 2H, J=6.8Hz), 4.11<br>(t, 2H, J=6.8Hz), 4.76(s,<br>2H), 7.10(d, 1H, J=7.9Hz),<br>7.25(t, 1H, J=7.9Hz), 7.53<br>(dt, 1H, J=2.0Hz & 7.9Hz),<br>8.16(dd, 1H, J=2.0Hz &<br>7.9Hz) | cald. 297.0000<br>obsd. 296.9994<br>(−0.6) |
| 3 | Oily product | 2920, 2870<br>1700, 1640<br>1490, 1410<br>1200, 1050<br>820, 780 | 2.25(m, 2H), 3.45(t, 2H,<br>J=7.3Hz), 3.84(s, 3H), 4.12<br>(t, 2H, J=7.3Hz), 4.73(s,<br>2H), 7.00–7.10(m, 2H), 7.58<br>(d, 1H, J=3.3Hz) | cald. 327.0106<br>obsd. 327.0106<br>(0.0) |
| 4 | 57–58° C. | 2930, 2900<br>1700, 1640<br>1620, 1410<br>1330, 1230<br>1140, 820<br>770 | 2.24(m, 2H), 2.39(s, 3H),<br>3.44(t, 2H, J=7.3Hz), 4.10<br>(t, 2H, J=7.3Hz), 4.73(s,<br>2H), 6.90(s, 1H), 7.04(d, 1H,<br>J=7.9Hz), 8.06(d, 1H,<br>J=7.9Hz) | calcd. 311.0157<br>obsd. 311.0171<br>(1.4) |
| 5 | Oily product | 2920, 2855<br>1635, 1600<br>1460, 1415<br>1315, 1275<br>1200, 1100<br>1040, 760 | 1.82(quintett, 2H,<br>J=6.7Hz), 1.97(quintett, 2H,<br>J=6.7Hz), 3.48–3.53(m,<br>4H), 3.66(t, 2H, J=6.7Hz),<br>4.39(t, 2H, J=5.4Hz), 7.01<br>(d, 1H, J=7.9Hz), 7.17(t, | calcd. 297.0363<br>obsd. 297.0361<br>(0.2) |

TABLE 1-continued

| Example | m.p. | IR (cm$^{-1}$) | NMR (δ ppm) | Mass |
|---|---|---|---|---|
| | | 700 | 1H, J=7.9Hz), 7.42(dt, 1H, J=2.0 & 7.9Hz), 7.79(dd, 1H, J=2.0 & 7.9Hz) | |
| 6 | Oily product | 2920, 1660 1630, 1485 1450, 1430 1225, 1190 1105, 1045 1020, 755 700 | 1.73–1.87(m, 4H), 3.42(t, 2H, J=6.6Hz), 3.59(t, 2H, J=6.6Hz), 4.49(s, 2H), 4.69 (s, 2H), 7.03–7.08(m, 2H), 7.18(dd, 1H, J=1.3 & 7.9Hz), 7.30(dt, 1H, J=1.3 & 7.9Hz) | calcd. 297.0364 obsd. 297.0408 (4.4) |
| 7 | 45–46° C. | 2930, 1700 1660, 1595 1475, 1440 1325, 1285 1210, 1115 1045, 755 | 1.81–1.92(m, 4H), 3.44(t, 2H, J=6.6Hz), 4.02(t, 2H, J=7.2Hz), 4.76(s, 2H), 7.10 (dd, 1H, J=1.3 & 7.9Hz), 7.26(dt, 1H, J=1.3 & 7.9Hz), 7.52(dt, 1H, J=2.0 & 7.9Hz), 8.16(dd, 1H, J=2.0 & 7.9Hz) | calcd. 311.0157 obsd. 311.0162 (0.5) |
| 8 | Oily product | 2950, 1710 1650, 1610 1490, 1290 1210, 1130 1050, 1030 830, 740 | 1.75–1.99(m, 4H), 3.44(t, 2H, J=6.6Hz), 3.84(s, 3H), 4.02(t, 2H, J=7.3Hz), 4.72 (s, 2H), 7.00–7.10(m, 2H), 7.57(d, 1H, J=3.3Hz) | calcd. 341.0261 obsd. 341.0227 (−3.4) |
| 9 | Oily product | 2950, 2860 1705, 1650 1600, 1560 1410, 1335 1310, 1285 1245, 1210 1130, 1085 1050, 880 860, 825 760 | 1.74–1.77(m, 4H), 3.43(t, 2H, J=6.6Hz), 4.00(t, 2H, J=6.6Hz), 4.76(5, 2H), 7.13 (d, 1H, J=2.0Hz, H-9), 7.22 (dd, 1H, J=2.0Hz & 8.6Hz), 8.13(d, 1H, J=8.6Hz) | calcd. 344.9766 obsd. 344.9733 (−3.3) |
| 10 | Oily product | 2950, 1700 1640, 1610 1410, 1290 1220, 1140 1060, 1020 820, 760 | 1.74–1.96(m, 4H), 2.39(s, 3H), 3.43(t, 2H, J=6.6Hz), 4.00(t, 2H, J=7.3Hz), 4.72 (s, 2H), 6.89(s, 1H), 7.04(d, 1H, J=7.9Hz), 8.06(d, 1H, J=7.9Hz) | calcd. 325.0312 obsd. 325.0280 (−3.2) |
| 11 | Oily product | 2920, 2830 1700, 1640 1605, 1445 1370, 1330 1270, 1235 1200, 1160 1130, 1130 840, 760 | 1.77–1.95(m, 4H), 3.43(t, 2H, J=3.9Hz), 3.86(s, 3H) 3,98(t, 2H, J=3.9Hz), 4.73 (s, 2H), 6.59(d, 1H, J= 2.6Hz), 6.77(dd, 1H, J= 2.6Hz & 9.0Hz) 8.14(d, 1H, J=9.0Hz) | calcd. 341.0262 obsd. 341.0262 (0.0) |
| 12 | Oily product | 2930, 2840 1705, 1660 1600, 1570 1470, 1430 1320, 1260 1240, 1095 1045, 1000 935, 800 | 1.77–1.97(m, 4H), 3.45(t, 2H, J=6.6Hz), 3.89(s, 3H), 4.04(t, 2H, J=6.6Hz), 4.72 (s, 2H), 6.70(d, 1H, J=8.6Hz), 6.82(d, 1H, J=8.6Hz), 7.40(t, 1H, J=8.6Hz) | calcd. 341.0263 obsd. 341.0304 (4.1) |
| 13 | 99–102° C. | 2930, 2850 1710, 1665 1600, 1460 1320, 1285 1265, 1240 1095, 805 735, 690 | 1.77–1.90(m, 4H), 3.32(t, 2H, J=6.5Hz), 4.03(t, 2H, J=6.5Hz), 4.72(s, 2H), 5.15 (s, 2H), 6.70(d, 1H, J=8.6Hz), 6.85(d, 1H, J=8.6Hz), 7.31–7.46(m, 6H) | |
| 14 | Oily product | 2940, 1730 1690, 1610 1585, 1520 1480, 1430 1340, 1305 1260, 1205 1150, 1120 1070, 1020 840, 770 745 | 1.80–1.87(m, 4H), 3.40(t, 2H, J=5.9Hz), 3.98–4.10 (m, 2H), 4.71(s, 2H), 7.49(s, 1H, J=9.2Hz), 8.48(dd, 1H, J=2.6Hz & 9.2Hz), 8.78(d, 1H, J=2.6Hz) | calcd. 356.0006 obsd. 355.9977 (−2.9) |
| 15 | 131–134° C. | 2940, 2850 1710, 1650 1600, 1490 1430, 1405 1310, 1270 1245, 1110 1040, 975 930, 845 | 1.75–1.98(m, 4H), 3.44(t, 2H, J=6.5Hz), 3.94(s, 3H), 4.02(t, 2H, J=6.5Hz), 4.79 (s, 2H), 7.16(d, 1H, J=8.6Hz), 8.17(dd, 1H, J=2.0Hz & 8.6Hz), 8.90(d, 1H, J=2.0Hz) | calcd. 369.0211 obsd. 369.0241 (3.0) |

TABLE 1-continued

| Example | m.p. | IR (cm$^{-1}$) | NMR (δ ppm) | Mass |
|---|---|---|---|---|
| 16 | 42–43° C. | 765<br>2930, 2850<br>1710, 1650<br>1600, 1480<br>1450, 1365<br>1340, 1295<br>1220, 1120<br>1055, 1040<br>820, 780<br>765, 695 | 1.51(quintett, 2H, J=<br>7.3Hz), 1.67(quintett, 2H,<br>J=7.3Hz), 1.91(quintett, 2H,<br>J=7.3Hz), 3.42(t, 2H,<br>J=7.3Hz), 3.98(t, 2H,<br>J=7.3Hz), 4.75(s, 2H), 7.10<br>(d, 1H, J=7.9Hz), 7.25(t,<br>1H, J=7.9Hz), 7.52(dt, 1H,<br>J=1.3Hz & 7.9Hz), 8.16(dd,<br>1H, J=1.3Hz & 7.9Hz) | calcd. 325.0312<br>obsd. 325.0298<br>(−1.4) |
| 17 | Oily product | 2950, 2850<br>1705, 1650<br>1605, 1490<br>1410, 1290<br>1030, 1030<br>820, 740 | 1.51(m, 2H), 1.69(m, 2H),<br>1.91(m, 2H), 3.42(t, 2H,<br>J=6.6Hz), 3.84(s, 3H), 3.98<br>(t, 2H, J=7.3Hz), 4.72(s,<br>2H), 6.97–7.06(m, 2H), 7.57<br>(d, 1H, J=3.3Hz) | calcd. 355.0418<br>obsd. 355.0386<br>(−3.2) |
| 18 | 43–44° C. | 2950, 2870<br>1710, 1640<br>1620, 1340<br>1140, 1030<br>830, 770<br>740 | 1.52(m, 2H), 1.68(m, 2H),<br>1.91(m, 2H), 2.39(s, 3H),<br>3.40(t, 2H, J=6.6Hz), 3.96<br>(t, 2H, J=7.3Hz), 4.72<br>(s, 2H), 6.89(s, 1H), 7.03<br>(d, 1H, J=7.9Hz),<br>8.06(d, 1H, J=7.9Hz) | calcd. 339.0468<br>obsd. 339.0465<br>(−0.3) |

EXAMPLE 19

Synthesis of 4-(3-(4-(2-pyridyl)piperazinyl)propyl)-2,3,4,5-tetrahydro-1,4-benzoxazepine-5-one

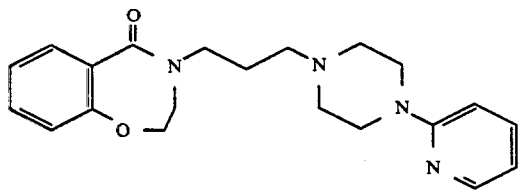

To a solution of 289 mg of the compound of Example 1 dissolved in 30 ml of dioxane, 0.937 ml (5 equivalents) of 1-(2-pyridyl)piperazine was added, and the mixture was heated under reflux for 17 hours. The dioxane was evaporated, aqueous sodium hydrogen carbonate was added, and the mixture was extracted with methylene chloride.

The extract was washed with saturated aqueous sodium chloride, and then dried over anhydrous magnesium sulfate. Then the methylene chloride solution was concentrated, and the residue was developed with methylene chloride-methanol (97:3) by silica gel column chromatography, to give 320 mg of the desired product (yield 73%). The hydrochloride was obtained by forming the hydrochloride in a conventional manner, followed by recrystallization from ethanol-ether.

EXAMPLE 20

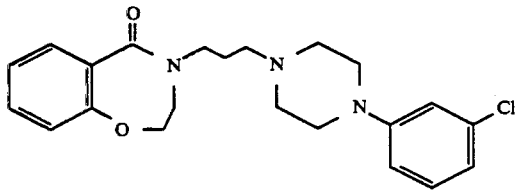

To a solution of 300 mg of the compound of Example 1 dissolved in 30 ml of dioxane, 1.23 g (5 equivalents) of 1-(3-chlorophenyl)piperazine was added, and the mixture was heated under reflux for 17 hours. The reaction treatment and purification were conducted as in Example 19, to give 380 mg of the desired compound (yield 76%). The hydrochloride was obtained by forming the hydrochloride in a conventional manner, followed by recrystallization from ethanol-ether.

EXAMPLE 21

Synthesis of 4-(3-(4-(2-pyridyl)piperazinyl)propyl)-2,3,4,5-tetrahydro-1,4-benzoxazepine-3,5-dion A 50 mg amount of the compound of Example 2 was dissolved in 10 ml of dioxane, and 0.133 ml of (5 equivalents) of 1-(2-pyridyl)piperazine was added, followed by stirring at 100° C. for 17 hours.

The reaction treatment was conducted as in Example 19, and developed with ethyl acetate-hexane (3:1) by silica gel column chromatography, to give 48.0 mg of the desired compound (yield 75%). The hydrochloride was obtained by forming the hydrochloride in a conventional manner, followed by recrystallization from methylene chloride-ether.

EXAMPLE 22

Synthesis of 4-(3-(4-(2-pyrimidinyl)piperazinyl)propyl)-2,3,4,5-tetrahydro-1,4-benzoxazepine -3,5-dione

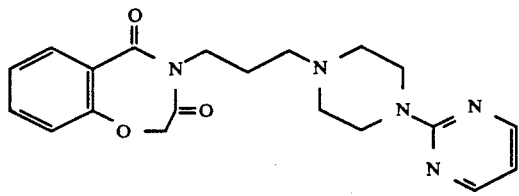

A 60 mg amount of the compound of Example 2 was dissolved in 10 ml of dioxane, and 168 mg (5 equivalents) of 1-(2-pyrimidinyl) piperazine was added, followed by stirring at 100° C. for 17 hours.

After the post-treatment conducted as in Example 19 and the purification as in Example 21, 61.6 mg of the desired compound was obtained (yield 80%). The hydrochloride was obtained by forming the hydrochloride in a conventional manner, followed by recrystallization from methylene chloride-ether.

EXAMPLE 23

Synthesis of 7-methoxy-4-(3-(2-pyridyl)piperazinyl)-propyl-2,3,4,5-tetrahydro-1,4-benzoxazepine-3,5

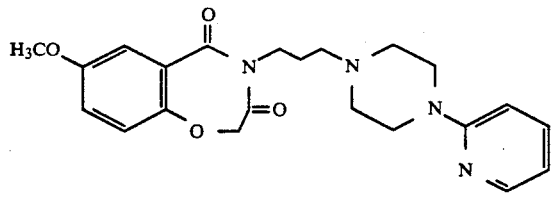

A 98 mg amount of the compound of Example 3 was dissolved in 10 ml of dioxane, and 147 mg (3 equivalents) of 1-(2-pyridyl)piperazine was added, followed by stirring at 100° C. for 20 hours.

The reaction mixture was poured into water and extracted with ethyl acetate, the organic layer was dried over anhydrous magnesium sulfate, and the solvent was evaporated under a reduced pressure. The residue was developed with ethyl acetate by silica gel column chromatography, to give 88 mg of the desired compound (yield 71.5%). The hydrochloride was obtained by forming the hydrochloride in a conventional manner, followed by recrystallization from methylene chloride-ether.

EXAMPLE 24

Synthesis of 7-methoxy-4-(3-(2-pyrimidinyl)-piperazinyl)propyl)-2,3,4,5-tetrahydro-1,4-benzoxazepine-3

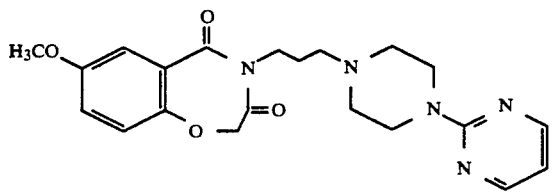

A 98 mg amount of the compound of Example 3 was dissolved in 10 ml of dioxane, and 147 mg (3 equivalents) of 1-(2-pyrimidinyl)piperazine was added, followed by stirring at 100° C. for 20 hours.

The reaction treatment and purification were conducted as in Example 23, to give 107 mg of the desired compound (yield 86.8%). The hydrochloride was obtained by forming the hydrochloride in a conventional manner, followed by recrystallization from methylene chloride-ether.

EXAMPLE 25

Synthesis of 8-methyl-4-(3-(2-pyridyl)piperazinyl) propyl)-2,3,4,5-tetrahydro-1,4-benzoxazepine-3,5-dione

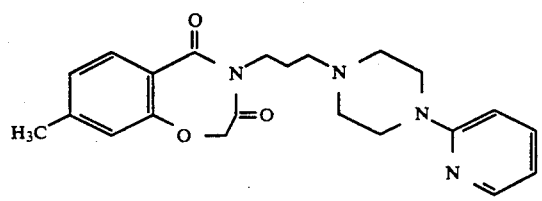

A 125 mg amount of the compound of Example 4 was dissolved in 10 ml of dioxane, and 196 mg (3 equivalents) of 1-(2-pyridyl)piperazine was added, followed by refluxing for 48 hours.

The reaction treatment and purification were conducted as in Example 23, to give 113 mg of the desired compound (yield 71.7%). The hydrochloride was obtained by forming the hydrochloride in a conventional manner, followed by recrystallization from methylene chloride-ether.

EXAMPLE 26

Synthesis of 8-methyl-4-(3-(2-pyrimidinyl)-piperazinyl)propyl-2,3,4,5-tetrahydro-1,4-benzoxazepine-3,5

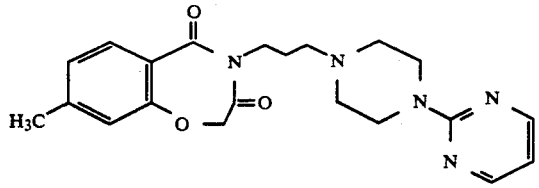

A 125 mg amount of the compound of Example 4 was dissolved in 10 ml of dioxane, and 196 mg (3 equivalents) of 1-(2-pyrimidinyl)piperazine was added, followed by stirring at 90 to 100° C. for 48 hours.

The reaction treatment and purification were conducted as in Example 23, to give 133 mg of the desired compound (yield 84.1%). The hydrochloride was obtained by forming the hydrochloride in a conventional manner, followed by recrystallization from methylene chloride-ether.

EXAMPLE 27

Synthesis of
4-(4-(4-(2-pyridyl)piperazinyl)butyl)-2,3,4,5-tetrahydro-1,4-benzoxazepine-5-one

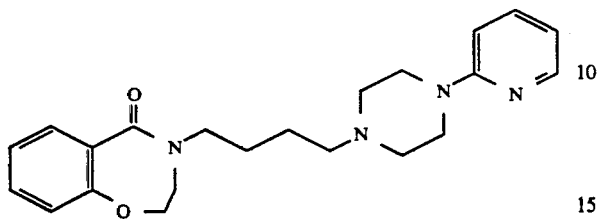

A 300 mg amount of the compound of Example 5 was dissolved in 30 ml of dioxane, and 0.782 ml (5 equivalents) of 1-(2-pyridyl)piperazine was added, followed by heating under reflux for 2 hours.

The reaction treatment and the purification were conducted as in Example 19, to give 342 mg of the desired compound (yield 89.4%).

EXAMPLE 28

Synthesis of
4-(4-(4-(2-pyrimidinyl)piperazinyl)butyl)-2,3,4,5-tetrahydro-1,4-benzoxazepine-5-one

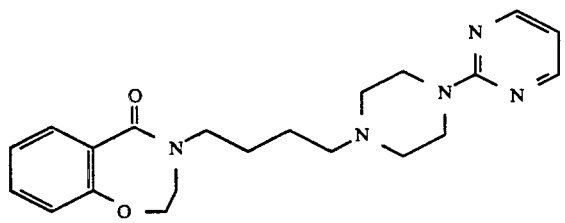

A 300 mg amount of the compound of Example 5 was dissolved in 30 ml of dioxane, and 825 mg (5 equivalents) of 1-(2-pyrimidinyl)piperazine was added, followed by heating under reflux for 17 hours.

The reaction treatment and the purification were conducted as in Example 19, to give 275 mg of the desired compound (yield 71.7%). The hydrochloride was obtained by forming the hydrochloride in a conventional manner, followed by recrystallization from ethanol-ether.

EXAMPLE 29

Synthesis of
4-(4-(4-(3-chlorophenyl)piperazinyl)butyl)-2,3,4,5-tetrahydro-1,4-benzoxazepine-5-on

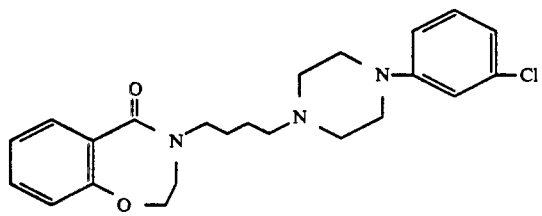

A 300 mg amount of the compound of Example 5 was dissolved in 30 ml of dioxane, and 986 mg (5 equivalents) of 1-(3-chlorophenyl)piperazine was added, followed by heating under reflux for 4 hours.

The reaction treatment and purification were conducted as in Example 19, to give 399 mg of the desired compound (yield 96%). The hydrochloride was obtained by forming the hydrochloride in a conventional manner, followed by recrystallization from ethanol-ether.

EXAMPLE 30

Synthesis of
4-(4-(4-(2-methoxyphenyl)piperazinyl)butyl-2,3,4,5-tetrahydro-1,4-benzoxazepine-5-on

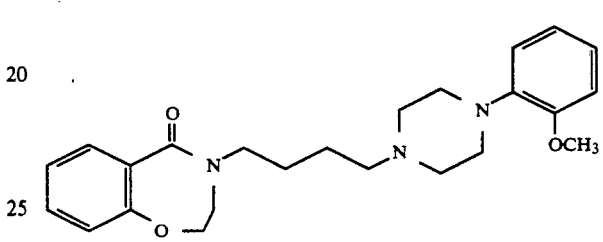

A 300 mg amount of the compound of Example 5 was dissolved in 30 ml of dioxane, and 0.902 ml (5 equivalents) of 1-(2-methoxyphenyl)piperazine was added, followed by heating under reflux for 2 hours.

The reaction treatment and purification were conducted as in Example 19, to give 387 mg of the desired compound (yield 94%). The hydrochloride was obtained by forming the hydrochloride in a conventional manner, followed by recrystallization from ethanol-ether.

EXAMPLE 31

Synthesis of
4-(4-(4-(2-pyridyl)piperazinyl)butyl)-2,3,4,5-tetrahydro-1,4-benzoxazepine-3-one

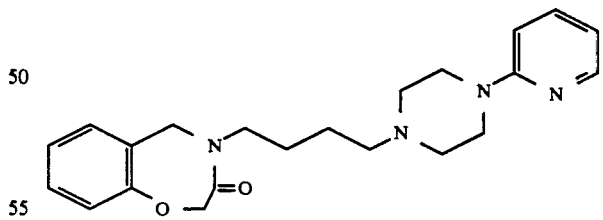

A 100 mg amount of the compound of Example 6 was dissolved in 10 ml of dioxane, and 0.26 ml (5 equivalents) of 1-(2-pyridyl)piperazine was added, followed by heating under reflux for 11 hours.

The reaction treatment and purification were conducted as in Example 19, to give 125 mg of the desired compound (yield 98%). The hydrochloride was obtained by forming the hydrochloride in a conventional manner, followed by recrystallization from methylene chloride-ether.

EXAMPLE 32

Synthesis of
4-(4-(4-(2-pyrimidinyl)piperazinyl)butyl-2,3,4,5-tetrahydro-1,4-benzoxazepine-3-one

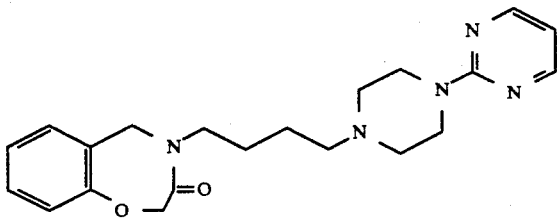

A 100 mg amount of the compound of Example 6 was dissolved in 10 ml of dioxane, and 275 mg (5 equivalents) of 1-(2-pyrimidinyl)piperazine was added, followed by heating under reflux for 17 hours.

The reaction treatment and purification were conducted as in Example 19, to give 118 mg of the desired compound (yield 92.3%). The hydrochloride was obtained by forming the hydrochloride in a conventional manner, followed by recrystallization from methylene chloride-ether.

EXAMPLE 33

Synthesis of
4-(4-(4-(3-chlorophenyl)piperazinyl)butyl)-2,3,4,5-tetrahydro-1,4-benzoxazepine -3,5-dione

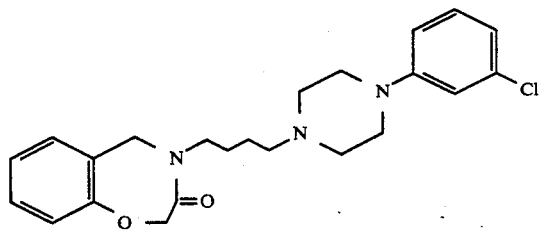

A 100 mg amount of the compound of Example 6 was dissolved in 10 ml of dioxane, and 330 mg (5 equivalents) of 1-(3-chlorophenyl)piperazine was added, followed by heating under reflux for 11 hours.

The reaction treatment and purification were conducted as in Example 19, to give 137 mg of the desired compound (yield 99%). The hydrochloride was obtained by forming the hydrochloride in a conventional manner, followed by recrystallization from ethanol-ether.

EXAMPLE 34

Synthesis of 4-(4-(4-phenylpiperazinyl)butyl)2,3,4,5-tetrahydro-1,4-benzoxazepine-3,5-dione

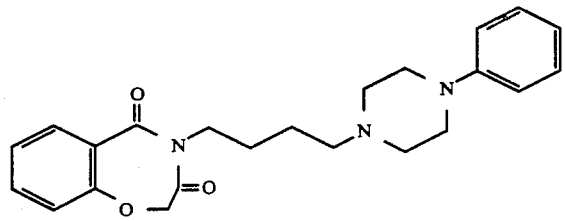

A 156 mg amount of the compound of Example 7 was dissolved in 10 ml of dioxane, and 243 mg (3 equivalents) of phenylpiperazine was added, followed by stirring at 90 to 100° C. for 12 hours.

The reaction treatment and purification were conducted as in Example 23, to give 180 mg of the desired compound (yield 91.5%). The hydrochloride was obtained by forming the hydrochloride in a conventional manner, followed by recrystallization from methylene chloride-ethyl acetate.

EXAMPLE 35

Synthesis of
4-(4-(4-(2-fluorophenyl)piperazinyl)butyl)-2,3,4,5-tetrahydro-1,4-benzoxazepine-3,5

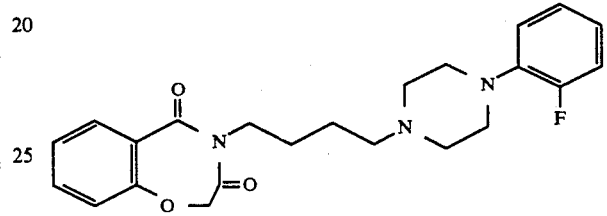

A 100 mg amount of the compound of Example 7 was dissolved in 10 ml of dioxane, and 173 mg (3 equivalents) of 1-(2-fluorophenyl)piperazine was added, followed by heating while stirring under reflux for 5 hours.

The reaction treatment was conducted as in Example 19 and purification as in Example 21, to give 126 mg of the desired compound (yield 96%). The hydrochloride was obtained by forming the hydrochloride in a conventional manner, followed by recrystallization from methylene chloride-ether.

EXAMPLE 36

Synthesis of
4-(4-(4-(2-chlorophenyl)piperazinyl)butyl)-2,3,4,5-tetrahydro-1,4-benzoxazepine-3,5

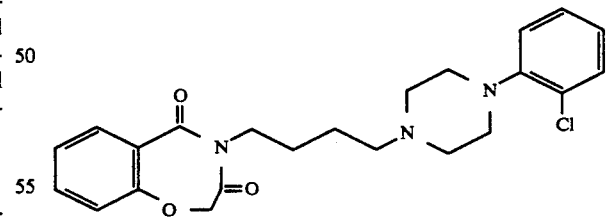

A 100 mg amount of the compound of Example 7 was dissolved in 10 ml of dioxane, and 315 mg (5 equivalents) of 1-(2-chlorophenyl)piperazine was added, followed by heating under reflux for 17 hours.

The reaction treatment was conducted as in Example 19 and purification as in Example 21, to give 114 mg of the title compound (yield 83%). The hydrochloride was obtained by forming the hydrochloride in a conventional manner, followed by recrystallization from methylene chloride-ether.

EXAMPLE 37

Synthesis of 4-(4-(4-(2-methoxyphenyl)piperazinyl)butyl)-2,3,4,5-tetrahydro-1,4-be 3-dione

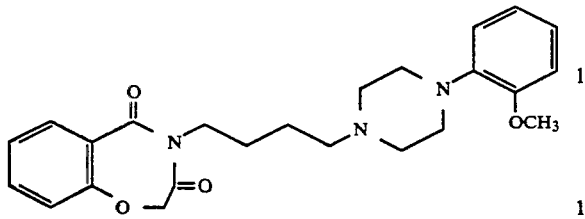

A 174 mg amount of the compound of Example 7 was dissolved in 20 ml of dioxane, and 0.5 ml of 1-(2-methoxyphenyl)piperazine was added, followed by heating under reflux for 6 hours.

The post-treatment was conducted as in Example 19 and the purification as in Example 21, to give 198 mg of the desired compound (yield 84%). The hydrochloride was obtained by forming the hydrochloride in a conventional manner, followed by recrystallization from methylene chloride-ether.

EXAMPLE 38

Synthesis of 4-(4-(4-(2-hydroxyphenyl)piperazinyl)butyl)-2,3,4,5-tetrahydro-1,4-benzoxazepine-3,5

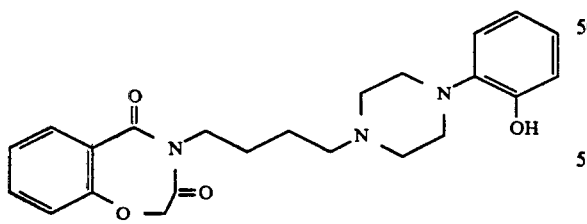

A 100 mg amount of the compound of Example 7 was dissolved in 20 ml of dioxane, and 171 mg (3 equivalents) of 1-(2-hydroxyphenyl)piperazine was added, followed by heating under stirring at 100° C. for hours.

The reaction treatment was conducted as in Example 19 and purification as in Example 21, to give mg of the desired compound (yield 98%). The hydrochloride was obtained by forming the hydrochloride in a conventional manner, followed by recrystallization from methylene chloride-ether.

EXAMPLE 39

Synthesis of 4-(4-(4-(3-chlorophenyl)piperazinyl)butyl-2,3,4,5-tetrahydro-1,4-benzoazepine-3,5

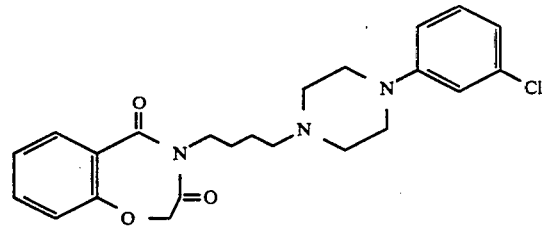

A 200 mg amount of the compound of Example 7 was dissolved in 20 ml of dioxane, and 631 mg (5 equivalents) of 1-(3-chlorophenyl)piperazine was added, followed by heating under reflux for 17 hours.

The reaction treatment was conducted as in Example 19 and purification as in Example 21, to give mg of the desired compound (yield 97%). The hydrochloride was obtained by forming the hydrochloride in a conventional manner, followed by recrystallization from methylene chloride-ether.

EXAMPLE 40

Synthesis of 4-(4-(4-(3-methoxyphenyl)piperazinyl)butyl)-2,3,4,5-tetrahydro-1,4-benzoxazepine-3,5

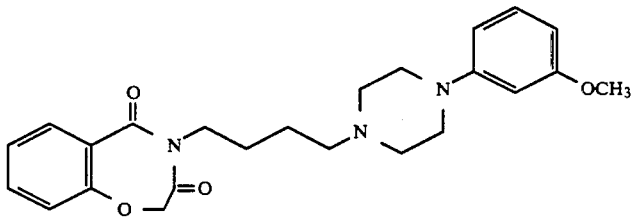

A 68.4 mg amount of the compound of Example 7 was dissolved in 10 ml of dioxane, and 131 mg (3 equivalents) of 1-(3-methoxyphenyl)piperazine was added, followed by heating under stirring at 100° C. for 17 hours.

The reaction treatment was conducted as in Example 19 and purification as in Example 21, to give 82.1 mg of the desired compound (yield 88%). The hydrochloride was obtained by forming the hydrochloride in a conventional manner, followed by recrystallization from methylene chloride-ether.

EXAMPLE 41

Synthesis of 4-(4-(4-(3-methylphenyl)piperazinyl)-butyl)-2,3,4,5-tetrahydro-1,4-benzoxazepine-3,5-d

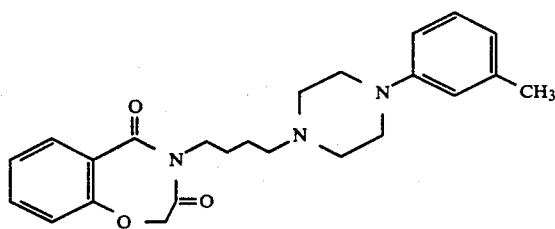

A 100 mg amount of the compound of Example 7 was dissolved in 20 ml of dioxane, and 169 mg (3 equivalents) of 1-(3-methylphenyl)piperazine was added, followed by heating under stirring at 100° C. for 10 hours.

The reaction treatment was conducted as in Example 19 and purification as in Example 21, to give 127 mg of the desired compound (yield 97%). The hydrochloride was obtained by forming the hydrochloride in a conventional manner, followed by recrystallization from methylene chloride-ether.

EXAMPLE 42

Synthesis of 4-(4-(4-(3-trifluoromethylphenyl)piperazinyl)butyl)-2,3,4,5-tetrahydro-1,4-benzoxazepine-

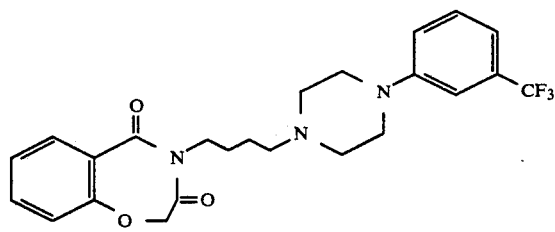

A 100 mg amount of the compound of Example 7 was dissolved in 10 ml of dioxane, and 228 mg (3 equivalents) of 1-(3-trifluoromethylphenyl) piperazine was added, followed by heating under stirring at 100° C. for 17 hours.

The reaction treatment was conducted as in Example 19 and purification as in Example 21, to give 136 mg of the desired compound (yield 91%). The hydrochloride was obtained by forming the hydrochloride in a conventional manner, followed by recrystallization from methylene chloride-ether.

EXAMPLE 43

Synthesis of 4-(4-(4-(4-fluorophenyl)piperazinyl)-butyl)-2,3,4,5-tetrahydro-1,4-benzoxazepine-3,5

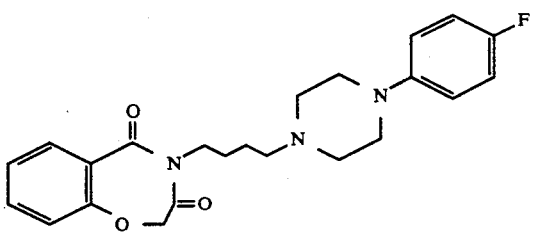

A 100 mg amount of the compound of Example 7 was dissolved in dioxane, and 151 mg (3 equivalents) of 1-(4-fluorophenyl)piperazine was added, followed by heating under stirring at 100° C for 17 hours.

The reaction treatment was conducted as in Example 19 and purification as in Example 21, to give mg of the desired compound (yield 99%). The hydrochloride was obtained by forming the hydrochloride in a conventional manner, followed by recrystallization from methylene chloride-ether.

EXAMPLE 44

Synthesis of 4-(4-(4-(4-chlorophenyl)piperazinyl)butyl)-2,3,4,5-tetrahydro-1,4-benzoxazepine -3,5-dione

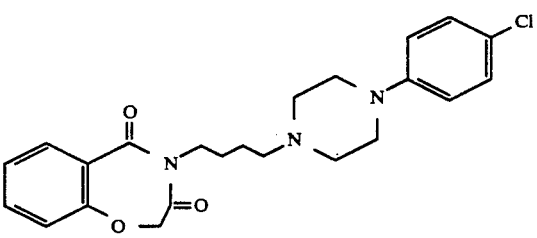

A 100 mg amount of the compound of Example 7 was dissolved in 10 ml of dioxane, and 189 mg (3 equivalents) of 1-(4-chlorophenyl)piperazine was added, followed by heating while stirring under reflux for 15 hours.

The reaction treatment was conducted as in Example 19 and purification as in Example 21, to give mg of the desired compound (yield 83%). The hydrochloride was obtained by forming the hydrochloride in a conventional manner, followed by recrystallization from methylene chloride-ether.

EXAMPLE 45

Synthesis of
4-(4-(4-(4-methoxyphenyl)piperazinyl)butyl)-2,3,4,5-tetrahydro-1,4-benzoxazepine -3,5-di

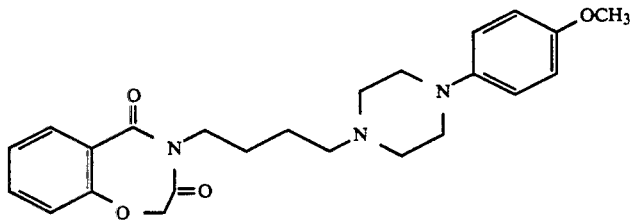

A 94.1 mg amount of the compound of Example 7 was dissolved in 10 ml of dioxane, and 299 mg (5 equivalents) of 1-(4-methoxyphenyl)piperazine was added, followed by heating under reflux for 6 hours.

The reaction treatment was conducted as in Example 19 and purification as in Example 21, to give mg of the desired compound (yield 81%). The hydrochloride was obtained by forming the hydrochloride in a conventional manner, followed by recrystallization from methylene chloride-ether.

EXAMPLE 46

Synthesis of
4-(4-(4-(4-acetylphenyl)piperazinyl)butyl)-2,3,4,5-tetrahydro-1,4-benzoxazepine -3,5-dione

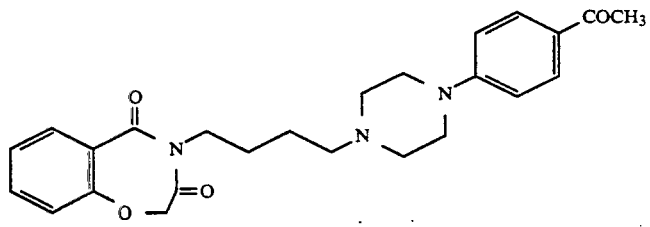

A 100 mg amount of the compound of Example 7 was dissolved in 10 ml of dioxane, and 216 mg (3 equivalents) of 94% 4-piperazinoacetophenone was added, followed by heating under stirring at 100° C. for hours.

The reaction treatment was conducted as in Example 19 and purification as in Example 21, to give mg of the desired compound (yield 72%). The hydrochloride was obtained by forming the hydrochloride in a conventional manner, followed by recrystallization from methylene chloride-ether.

EXAMPLE 47

Synthesis of
4-(4-4-(2-(pyridyl)piperazinyl)butyl)-2,3,4,5-tetrahydro-1,4-benz ,5-dione

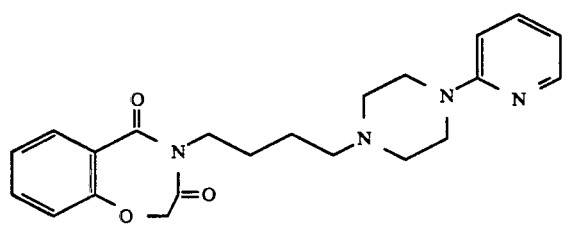

A 200 mg amount of the compound of Example 7 was dissolved in 20 ml of dioxane, and 0.498 ml (5 equivalents) of 1-(2-pyridyl)piperazine was added, followed by heating under reflux for 17 hours.

The reaction treatment was conducted as in Example 19 and purification as in Example 21, to give mg of the desired compound (yield 77.6%). The hydrochloride was obtained by forming the hydrochloride in a conventional manner, followed by recrystallization from methylene chloride-ether.

EXAMPLE 48

Synthesis of
4-(4-(4-(3-chloro-2-pyridyl)piperazinyl)butyl)-2,3,4,5-tetrahydro-1,4-benzoxazepine

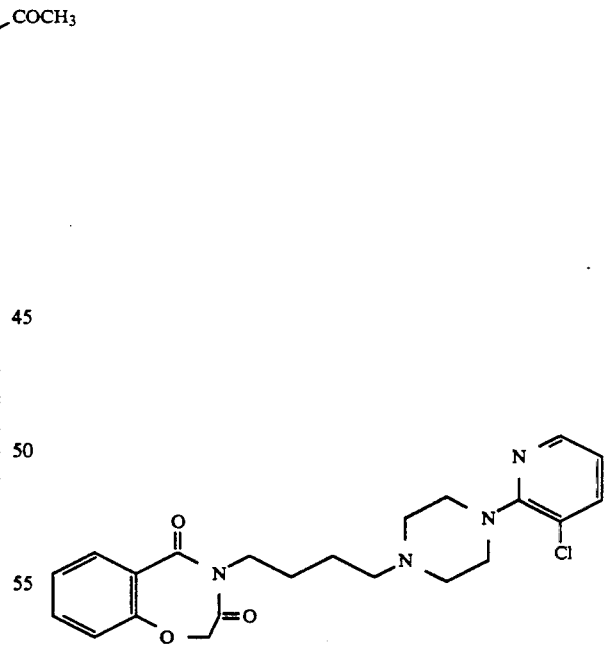

A 156 mg amount of the compound of Example 7 was dissolved in 10 ml of dioxane, and 295 mg (3 equivalents) of 1-(3-chloro-2-pyridyl)piperazine was added, followed by heating under stirring at 100° C. for hours.

The reaction treatment and purification were conducted as in Example 23, to give 225 mg of the desired compound (yield 98.0%). The hydrochloride was obtained by forming the hydrochloride in a conventional manner, followed by recrystallization from methylene chloride-ether.

EXAMPLE 49

Synthesis of
4-(4-(4-(3-nitro-2-pyridyl)piperazinyl)butyl)-2,3,4,5-tetrahydro-1,4-benzoxazepine-

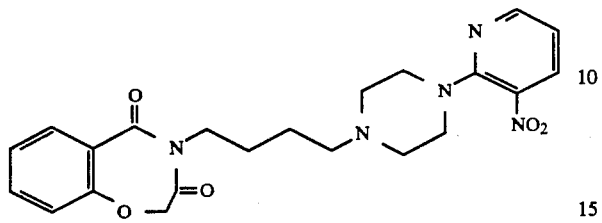

A 156 mg amount of the compound of Example 7 was dissolved in 10 ml of dioxane, and 312 mg (3 equivalents) of 1-(3-nitro-2-pyridyl)piperazine was added, followed by refluxing for 23 hours.

The reaction treatment and purification were conducted as in Example 23, to give 210 mg of the desired compound (yield 95.5%). The hydrochloride was obtained by forming the hydrochloride in a conventional manner, followed by recrystallization from methylene chloride-ether.

EXAMPLE 50

Synthesis of
4-(4-(4-(3-cyano-2-pyridyl)piperazinyl)butyl)-2,3,4,5-tetrahydro-1,4-benzoxazepine-

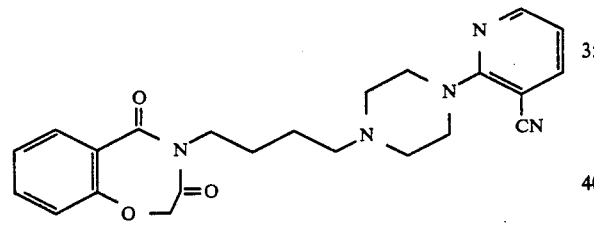

A 156 mg amount of the compound of Example 7 was dissolved in 10 ml of dioxane, and 282 mg (3 equivalents) of 1-(3-cyano-2-pyridyl)piperazine was added, followed by refluxing for 20 hours.

The reaction treatment and purification were conducted as in Example 23, to give 190 mg of the desired compound (yield 90.6%). The hydrochloride was obtained by forming the hydrochloride in a conventional manner, followed by recrystallization from methylene chloride-ether.

EXAMPLE 51

Synthesis of
4-(4-(4-(3-amino-2-pyridyl)-piperazinyl)butyl)-2,3,4,5-tetrahydro -1,4-benzoxazepine-3,5-dione

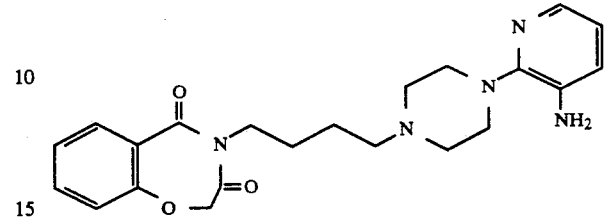

A 94 mg amount of the compound of Example 7 was dissolved in 6 ml of dioxane, and 160 mg (3 equivalents) of 1-(3-amino-2-pyridyl)piperazine was added, followed by refluxing for 48 hours.

The reaction treatment and purification were conducted as in Example 23, to give 94 mg of the desired compound (yield 76.5%). The hydrochloride was obtained by forming the hydrochloride in a conventional manner, followed by recrystallization from ethanol-ether.

EXAMPLE 52

Synthesis of
4-(4-(4-(2-pyrimidinyl)piperazinyl)butyl)-2,3,4,5-tetrahydro-1,4-benzoxazepine-3,5-d

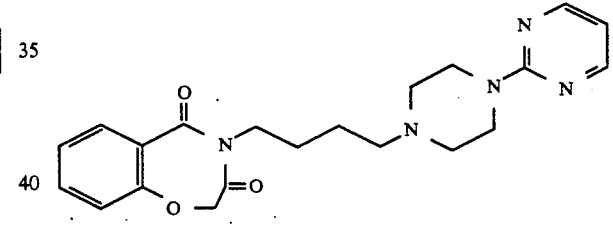

A 500 mg amount of the compound of Example 7 was dissolved in 50 ml of dioxane, and 1.31 g (5 equivalents) of 1-(2-pyrimidinyl)piperazine was added, followed by heating under reflux for 17 hours.

The reaction treatment was conducted as in Example 19 and purification as in Example 21, to give mg of the desired compound (yield 95.1%). The hydrochloride was obtained by forming the hydrochloride in a conventional manner, followed by recrystallization from methylene chloride-ether.

EXAMPLE 53

Synthesis of
7-methoxy-4-(4-(4-(2-pyridyl)piperazinyl)butyl)-2,3,4,5-tetrahydro-1,4-benzoxazepin 3,5-dione

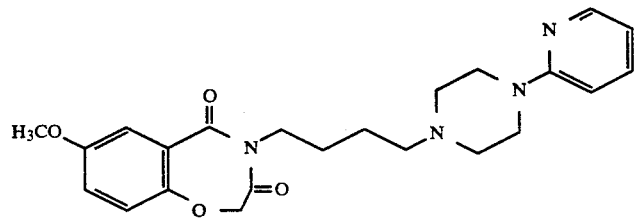

A 100 mg amount of the compound of Example 8 was dissolved in 10 ml of dioxane, and 147 mg (3 equivalents) of 1-(2-pyridyl)piperazine was added, followed by heating under stirring at 90° C. for 48 hours.

The reaction treatment and purification were conducted as in Example 23, to give 108 mg of the desired compound (yield 84.8%). The hydrochloride was obtained by forming the hydrochloride in a conventional manner, followed by recrystallization from methylene chloride-ether.

EXAMPLE 54

Synthesis of 7-methoxy-4-(4-(4-(3-chloro-2-pyridyl)-piperazinyl)butyl)-2,3,4,5-tetrahydro -1,4-benzoxazepine-3,5-dione A 137 mg amount of the compound of Example 8 was dissolved in 10 ml of dioxane, and 249 mg (3 equivalents) of 1-(3-nitro-2-pyridyl)piperazine was added, followed by refluxing for 40 hours.

The reaction treatment and purification were conducted as in Example 23, to give 182 mg of the desired compound (yield 96.9%). The hydrochloride was obtained by forming the hydrochloride in a conventional manner, followed by recrystallization from methylene chloride-ether.

EXAMPLE 57

Synthesis of 7methoxy-4-(4-(4-(3-cyano-2-pyridyl)-piperazinyl)butyl)-2,3,4,5-tetrahydro -1,4-benzoxazepine-3,5-dione

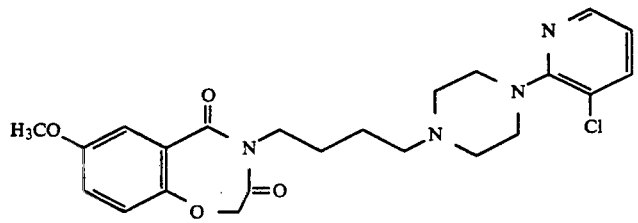

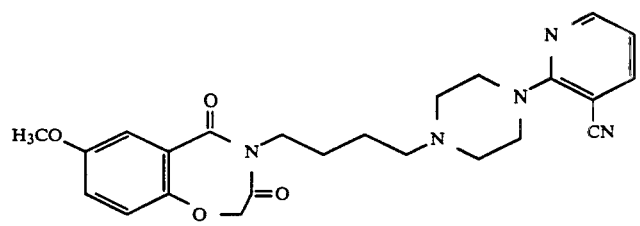

A 137 mg amount of the compound of Example 8 was dissolved in 10 ml of dioxane, and 236 mg (3 equivalents) of 1-(3-chloro-2-pyridyl)piperazine was added, followed by refluxing for 40 hours.

The reaction treatment and purification were conducted as in Example 23, to give 209 mg of the desired compound (yield 99.1%). The hydrochloride was obtained by forming the hydrochloride in a conventional manner, followed by recrystallization from methylene chloride-ether.

EXAMPLE 55

Synthesis of 7-methoxy-4-(4-(4-(3-nitro-2-pyridyl)piperazinyl)-butyl)-2,3,4,5-tetrahydro-1,4-3,5-dione A 138 mg amount of the compound of Example 8 was dissolved in 10 ml of dioxane, and 235 mg (3 equivalents) of 1-(3-cyano-2-pyridyl)piperazine was added, followed by refluxing for 40 hours.

The reaction treatment and purification were conducted as in Example 23, to give 182 mg of the desired compound (yield 98.5%). The hydrochloride was obtained by forming the hydrochloride in a conventional manner, followed by recrystallization from methylene chloride-ether.

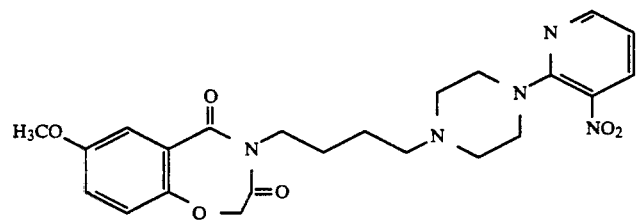

EXAMPLE 57

Synthesis of
7-methoxy-4-(4-(4-(3-amino-2-pyridyl)-piperazinyl)-butyl)-2,3,4,5-tetrahydro-1,4-benzoxazepine-3,5-dione

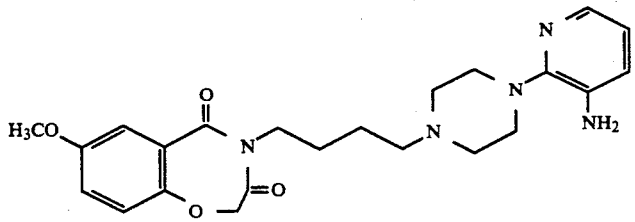

A 244 mg amount of the compound of Example 55 was dissolved in 10 ml of ethanol, and 50 mg of platinum dioxide was added to carry out hydrogenation for 0.5 hour.

The reaction mixture obtained was filtered, the filtrate was evaporated under a reduced pressure, and the residue was eluted with ethyl acetate by silica gel column chromatography, to give 179 mg of the desired compound (yield 83.4%). The hydrochloride was obtained by forming the hydrochloride in a conventional manner, followed by recrystallization from ethanol-ether.

EXAMPLE 58

Synthesis of
7-methoxy-4-(4-(4-(2-pyrimidinyl)piperazinyl)butyl)-2,3,4,5-tetrahydro-1,4-benzoxaze-3,5-dione

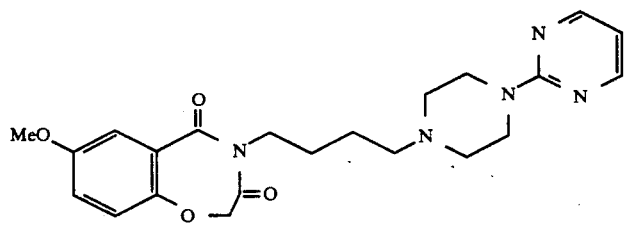

A 100 mg amount of the compound of Example 8 was dissolved in 10 ml of dioxane, and 147 mg (3 equivalents) of 1-(2-pyrimidinyl)piperazine was added, followed by stirring at 90° C. for 48 hours.

The reaction treatment and purification were conducted as in Example 23, to give 116 mg of the desired compound (yield 90.9%). The hydrochloride was obtained by forming the hydrochloride in a conventional manner, followed by recrystallization from methylene chloride-ether.

EXAMPLE 59

Synthesis of
8-chloro-4-(4-(4-(2-pyridyl)piperazinyl)butyl)-2,3,4,5-tetrahydro-1,4-benzoxazepine-3,5-dione

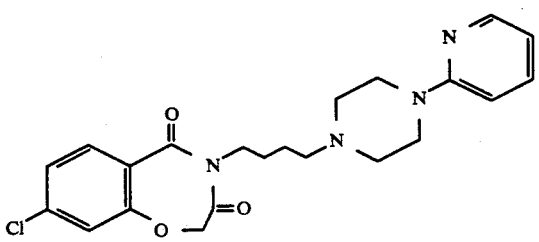

A 98.0 mg amount of the compound of Example 9 was dissolved in 10 ml of dioxane, and 0.132 ml (3 equivalents) of 1-(2-pyridyl)piperazine was added, followed by heating under stirring at 100° C. for 10

The reaction treatment was conducted as in Example 19 and purification as in Example 21, to give 86.8 mg of the desired compound (yield 72%). The hydrochloride was obtained by forming the hydrochloride in a conventional manner, followed by recrystallization from methylene chloride-ether.

EXAMPLE 60

Synthesis of
8-chloro-4-(4-(4-(3-chloro-2-pyridyl)piperazinyl)butyl)-2,3,4,5-tetrahydro-1,4-3,5-dione

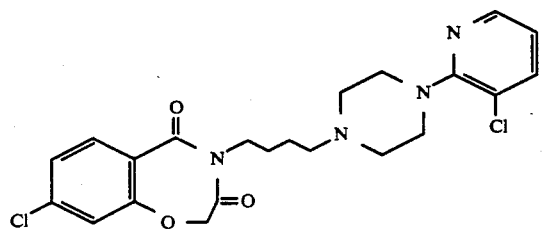

A 102 mg amount of the compound of Example 9 was dissolved in 10 ml of dioxane, and 58.1 mg (1 equivalent) of 1-(3-chloro-2-pyridyl)piperazine and mg (3 equivalent) of potassium carbonate were added, followed by heating under reflux for 2 days.

The reaction treatment was conducted as in Example 19 and purification as in Example 21, to give 86.3 mg of the desired compound (yield 63%). The hydrochloride was obtained by forming the hydrochloride in a conventional manner, followed by recrystallization from methylene chloride-ether.

EXAMPLE 61

Synthesis of
8-chloro-4-(4-(4-(3-nitro-2-pyridyl)piperazinyl)butyl)-
2,3,4,5-tetrahydro -1,4-3,5-dione

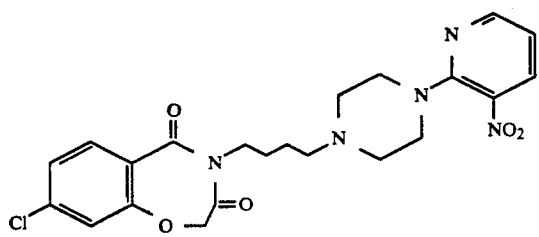

A 121 mg amount of the compound of Example 9 was dissolved in 15 ml of dioxane, and 218 mg (3 equivalents) of 1-(3-nitro-2-pyridyl)piperazine was added, followed by heating under reflux for 5 hours.

The reaction treatment was conducted as in Example 19 and purification as in Example 21, to give mg of the desired compound (yield 80%). The hydrochloride was obtained by forming the hydrochloride in a conventional manner, followed by recrystallization from methylene chloride-ether.

EXAMPLE 62

Synthesis of
8-chloro-4-(4-(4-(3-cyano-2-pyridyl)piperazinyl)butyl)-
2,3,4,5-tetrahydro -1,4-3,5-dione

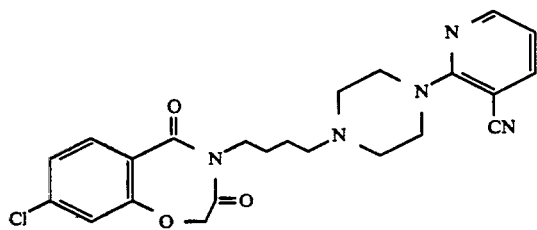

A 102 mg amount of the compound of Example 9 was dissolved in 10 ml of dioxane, and 55.3 mg (1 equivalent) of 1-(3-cyano-2-pyridyl)piperazine and mg (3 equivalents) of potassium carbonate were added, followed by heating under reflux for 2 days.

The reaction treatment was conducted as in Example 19 and purification as in Example 21, to give 88.2 mg of the desired compound (yield 66%). The hydrochloride was obtained by forming the hydrochloride in a conventional manner, followed by recrystallization from methylene chloride-ether.

EXAMPLE 63

Synthesis of
8-chloro-4-(4-(4-(3-amino-2-pyridyl)piperazinyl)butyl)-
2,3,4,5-tetrahydro -1,4-3,5-dione

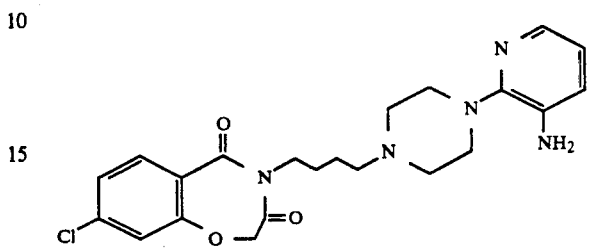

A 104 mg amount of the compound of Example 9 was dissolved in 10 ml of dioxane, and 160 mg (3 equivalents) of 1-(3-amino-3-pyridyl)piperazine was added, followed by heating under reflux for 17 hours.

The reaction treatment was conducted as in Example 19 and purification as in Example 21, to give mg of the desired compound (yield 87%). The hydrochloride was obtained by forming the hydrochloride in a conventional manner, followed by recrystallization from methylene chloride-ether.

EXAMPLE 64

Synthesis of
8-chloro-4-(4-(4-(2-pyrimidinyl)piperazinyl)butyl)-
2,3,4,5-tetrahydro -1,4-benzoxazepine-3,5-dione

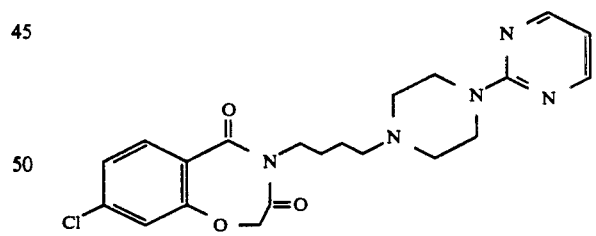

A 98.0 mg amount of the compound of Example 9 was dissolved in 10 ml of dioxane, and 139 mg (3 equivalents) of 1-(2-pyrimidinyl)piperazine was added, followed by heating under reflux for 4 hours.

The reaction treatment was conducted as in Example 19 and purification as in Example 21, to give 88.9 mg of the desired compound (yield 73%). The hydrochloride was obtained by forming the hydrochloride in a conventional manner, followed by recrystallization from methylene chloride-ether.

EXAMPLE 65

Synthesis of
8-methyl-4-(4-(4-(2-pyridyl)piperazinyl)butyl)-2,3,4,5-tetrahydro -1,4-benzoxazepine-3,5-dione

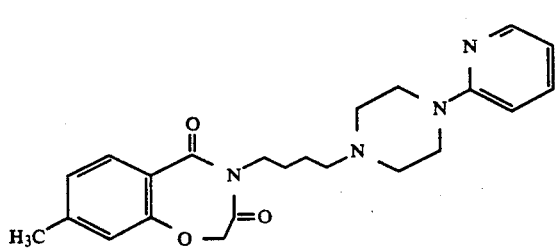

A 130 mg amount of the compound of Example 10 was dissolved in 10 ml of dioxane, and 196 mg (3 equivalents) of 1-(2-pyridyl)piperazine was added, followed by stirring at 90 to 100° C. for 48 hours.

The reaction treatment and purification were conducted as in Example 23, to give 149 mg of the desired compound (yield 91.2%). The hydrochloride was obtained by forming the hydrochloride in a conventional manner, followed by recrystallization from methylene chloride-ether.

EXAMPLE 66

Synthesis of
8-methyl-4-(4-(4-(3-chloro-2-pyridyl)piperazinyl)-butyl)-2,3,4,5-tetrahydro -1,4-3,5-dione

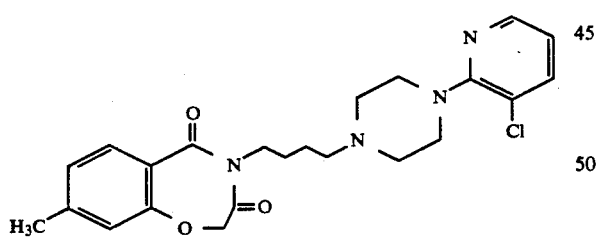

A 130 mg amount of the compound of Example 10 was dissolved in 10 ml of dioxane, and 236 mg (3 equivalents) of 1-(3-chloro-2-pyridyl)piperazine was added, followed by refluxing for 20 hours.

The reaction treatment and purification were conducted as in Example 23, to give 172 mg of the desired compound (yield 97.1%). The hydrochloride was obtained by forming the hydrochloride in a conventional manner, followed by recrystallization from methylene chloride-ether.

EXAMPLE 67

Synthesis of
8-methyl-4-(4-(4-(3-nitro-2-pyridyl)piperazinyl)butyl)-2,3,4,5-tetrahydro -1,4-3,5-dione

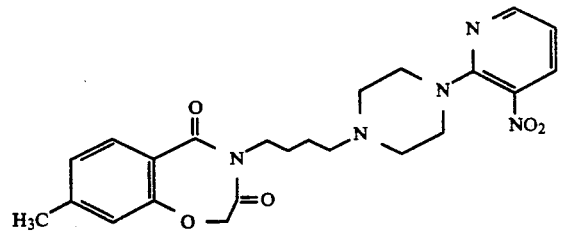

A 130 mg amount of the compound of Example 10 was dissolved in 10 ml of dioxane, and 249 mg (3 equivalents) of 1-(3-nitro-2-pyridyl)piperazine was added, followed by refluxing for 20 hours.

The reaction treatment and purification were conducted as in Example 23, to give 197 mg of the desired compound (yield 97.5%). The hydrochloride was obtained by forming the hydrochloride in a conventional manner, followed by recrystallization from methylene chloride-ether.

EXAMPLE 69

Synthesis of
8-methyl-4-(4-(4-(3-cyano-2-pyridyl)piperazinyl)butyl)-2,3,4,5-tetrahydro -1,4-3,5-dione

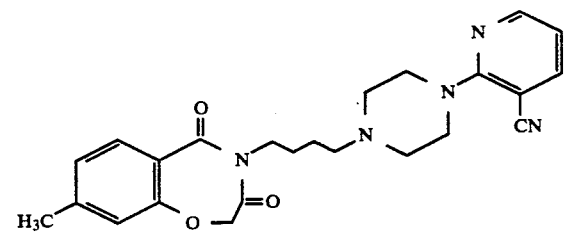

A 130 mg amount of the compound of Example 10 was dissolved in 10 ml of dioxane, and 225 mg (3 equivalents) of 1-(3-cyano-2-pyridyl)piperazine was added, followed by refluxing for 20 hours.

The reaction treatment and purification were conducted as in Example 23, to give 207 mg of the desired compound (yield 96.2%). The hydrochloride was obtained by forming the hydrochloride in a conventional manner, followed by recrystallization from methylene chloride-ether.

EXAMPLE 69

Synthesis of
8-methyl-4-(4-(4-(3-amino-2-pyridyl)piperazinyl)butyl)-2,3,4,5-tetrahydro-1,4-3,5-dione

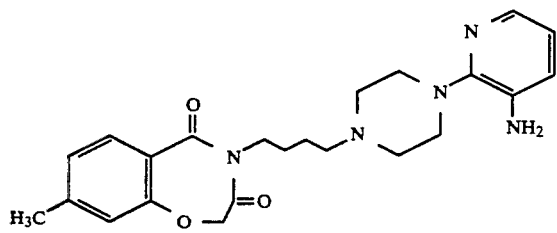

Using 249 mg of the compound of Example 67, the reaction treatment and purification were conducted as in Example 57, to give 101 mg of the desired compound (yield 48.9%). The hydrochloride was obtained by forming the hydrochloride in a conventional manner, followed by recrystallization from ethanol-ether.

EXAMPLE 70

Synthesis of
8-methyl-4-(4-(4-(2-pyrimidinyl)piperazinyl)butyl)-2,3,4,5-tetrahydro-1,4-benzoxazepine-3,5-dione

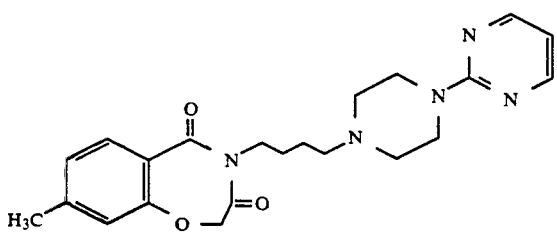

A 130 mg amount of the compound of Example 10 was dissolved in 10 ml of dioxane, and 196 mg (3 equivalents) of 1-(2-pyrimidinyl)piperazine was added, followed by stirring at 90 to 100° C. for 48 hours.

The reaction treatment and purification were conducted as in Example 23, to give 155 mg of the desired compound (yield 94.7%). The hydrochloride was obtained by forming the hydrochloride in a conventional manner, followed by recrystallization from methylene chloride-ether.

EXAMPLE 71

Synthesis of
8-methoxy-4-(4-(4(2-pyridyl)-piperazinyl)butyl)-2,3,4,5-tetrahydro-1,4-benzoxazepine-3,5-dione

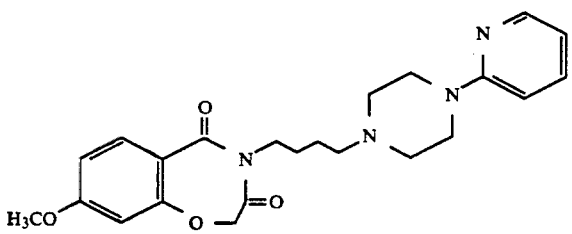

A 106 mg amount of the compound of Example 11 was dissolved in 10 ml of dioxane, and 0.144 ml (3 equivalents) of 1-(2-pyridyl)piperazine was added, followed by heating under reflux for 5 hours.

The reaction treatment was conducted as in Example 19 and purification as in Example 21, to give 81.8 mg of the desired compound (yield 62%). The hydrochloride was obtained by forming the hydrochloride in a conventional manner, followed by recrystallization from methylene chloride-ether.

EXAMPLE 72

Synthesis of
8-methoxy-4-(4-(4-(2-pyrimidinyl)piperazinyl)butyl)-2,3,4,5-tetrahydro-1,4-benzoxazepine-3,5-dione

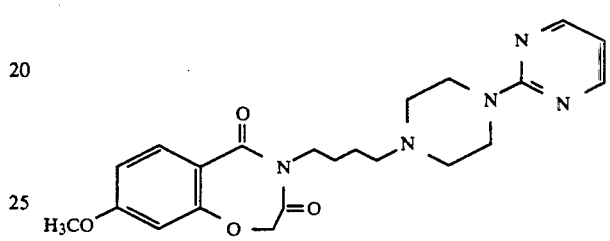

A 200 mg amount of the compound of Example 11 was dissolved in 20 ml of dioxane, and 288 mg (3 equivalents) of 1-(2-pyrimidinyl)piperazine was added, followed by heating under reflux for 5 hours.

The reaction treatment was conducted as in Example 19 and purification as in Example 21, to give mg of the desired compound (yield 57%). The hydrochloride was obtained by forming the hydrochloride in a conventional manner, followed by recrystallization from methylene chloride-ether.

EXAMPLE 73

Synthesis of
6-methoxy-4-(4-(4-(2-pyridyl)piperazinyl)butyl)-2,3,4,5-tetrahydro-1,4-benzoxazepine-3,5-dione

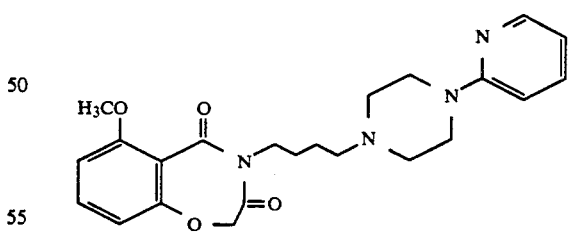

A 55 mg amount of the compound of Example 12 was dissolved in 10 ml of dioxane, and 0.0749 ml (3 equivalents) of 1-(2-pyridyl)piperazine was added, followed by heating under reflux for 7 hours.

The reaction treatment was conducted as in Example 19 and purification as in Example 21, to give 64.8 mg of the desired compound (yield 95%). The hydrochloride was obtained by forming the hydrochloride in a conventional manner, followed by recrystallization from methylene chloride-ether.

EXAMPLE 74

Synthesis of
6-methoxy-4-(4-(4-(2-pyrimidinyl)piperazinyl)butyl)-
2,3,4,5-tetrahydro -1,4-benzoxazepine-3,5-dione.

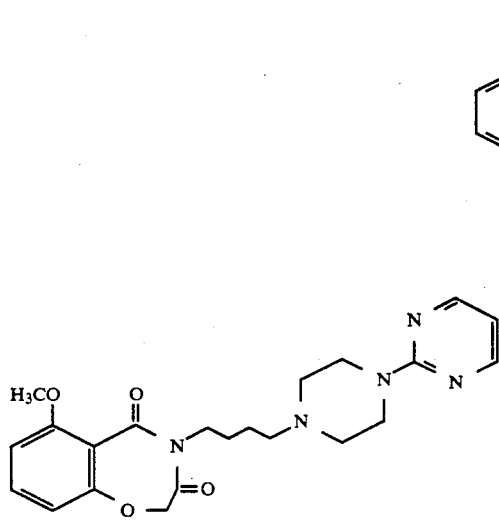

A 60.8 mg amount of the compound of Example 12 was dissolved in 10 ml of dioxane, and 87.4 mg (3 equivalents) of 1-(2-pyrimidinyl)piperazine was added, followed by heating under reflux for 7 hours.

The reaction treatment was conducted as in Example 19 and purification as in Example 21, to give 61.0 mg of the desired compound (yield 81%). The hydrochloride was obtained by forming the hydrochloride in a conventional manner, followed by recrystallization from methylene chloride-ether.

EXAMPLE 75

Synthesis of
6-benzyloxy-4-(4-(4-(2-pyridyl)piperazinyl)butyl)-
2,3,4,5-tetrahydro -1,4-benzoxazepine-3,5-dione

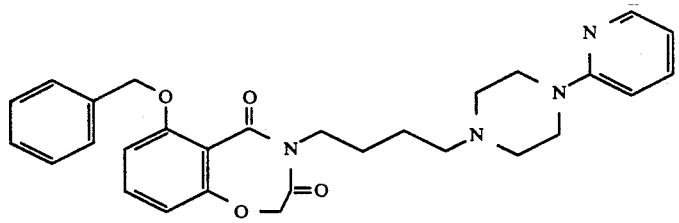

A 229 mg amount of the compound of Example 13 was dissolved in 20 ml of dioxane, and 0.255 ml (3 equivalents) of 1-(2-pyridyl)piperazine was added, followed by heating under reflux for 7 hours. Next, the dioxane was evaporated, aqueous sodium hydrogen carbonate was added, and the mixture was extracted with methylene chloride.

The extract was washed with saturated aqueous sodium chloride, dried over anhydrous magnesium sulfate, the methylene chloride solution was then concentrated, and the residue was developed with ethyl acetate by silica gel column chromatography to give 210 mg of the desired compound (yield 77%).

EXAMPLE 76

Synthesis of
6-benzyloxy-4-(4-(4-(2-pyrimidinyl)piperazinyl)butyl)-
2,3,4,5-tetrahydro -1,4-benzoxazepine-3,5-dione

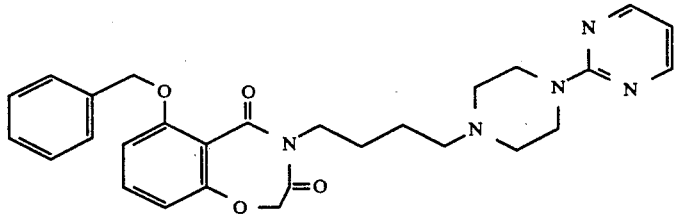

A 202 mg amount of the compound of Example 13 was dissolved in 20 ml of dioxane, and 242 mg (3 equivalents) of 1-(2-pyrimidinyl)piperazine was added, followed by heating under reflux for 7 hours. The reaction treatment and purification were conducted as in Example 75, to give 195 mg of the desired compound (yield 79%). The maleic acid salt was obtained in a conventional manner.

EXAMPLE 77

Synthesis of
6-hydroxy-4-(4-(4-(2-pyridyl)piperazinyl)butyl)-2,3,4,5-
tetrahydro -1,4-benzoxazepine-3,5-dione

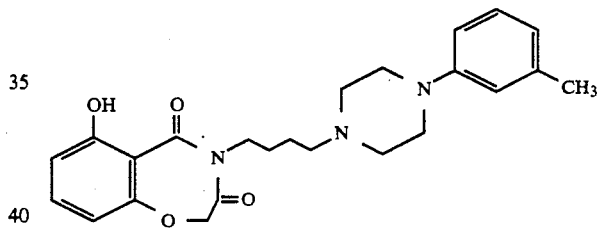

To 20.5 mg of 10% palladium-carbon, 5 ml of ethyl acetate was added, and after the atmosphere in the reaction vessel was replaced with hydrogen and the mixture was stirred at room temperature for 30 minutes, a solution of 205 mg of the compound of Example 75 dissolved in 5 ml of ethyl acetate was added, followed by stirring at room temperature for 11 hours.

The reaction mixture was filtered, the solvent was evaporated from the filtrate, and the residue was developed with hexane-ethyl acetate (1:2) by silica gel column chromatography, to give 140 mg of the desired compound (yield 83%). The hydrochloride was obtained by forming the hydrochloride in a conventional manner, followed by recrystallization from methylene chloride-ether.

EXAMPLE 78

Synthesis of 6-hydroxy-4-(4-(4-(2-pyrimidinyl)piperazinyl)butyl)-2,3,4,5-tetrahydro -1,4-benzoxazepine-3,5-dione

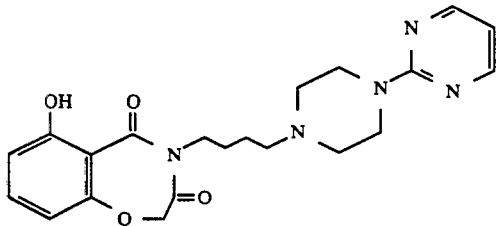

To 23.6 mg of 10% palladium-carbon, 5 ml of ethyl acetate was added, and after the atmosphere in the reaction vessel was replaced with hydrogen and the mixture was stirred at room temperature for 30 minutes, a solution of 236 mg of the compound of Example 76 dissolved in 5 ml of ethyl acetate was added, followed by stirring at room temperature for 17 hours.

The reaction treatment and purification were conducted as in Example 77, to give 160 mg of the desired compound (yield 83%). The hydrochloride was obtained by forming the hydrochloride in a conventional manner, followed by recrystallization from methylene chloride-ether.

EXAMPLE 79

Synthesis of 7-nitro-4-(4-(4-(2-pyridyl)piperazinyl)butyl)-2,3,4,5-tetrahydro -1,4-benzoxazepine-3,5-dione

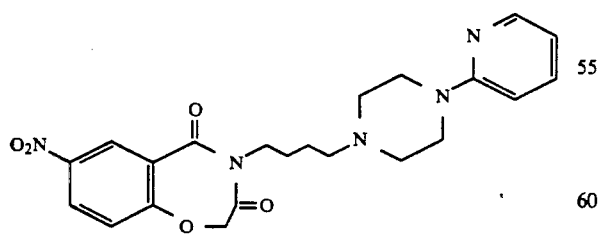

A 7.2 mg amount of the compound of Example 7 was dissolved in 3 ml of dioxane, and 0.00937 ml (3 equivalents) of 1-(2-pyridyl)piperazine was added, followed by heating while stirring under reflux for 2 hours.

The reaction treatment was conducted as in Example 19 and purification as in Example 21, to give 2.7 mg of the desired compound (yield 30%). The maleic acid salt was obtained by forming the maleic acid salt in a conventional manner, followed by recrystallization from methylene chloride-ether.

EXAMPLE 80

Synthesis of 7-nitro-4-(4-(4-(2-pyrimidinyl)piperazinyl)butyl)-2,3,4,5-tetrahydro -1,4-benzoxazepine-3,5-dione

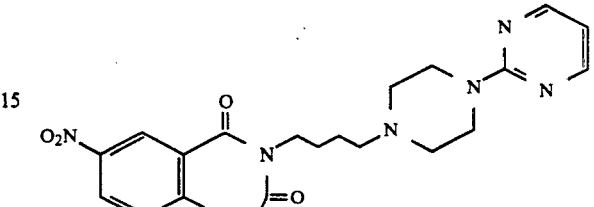

A 8.2 mg amount of the compound of Example 14 was dissolved in 3 ml of dioxane, and 11.3 mg (3 equivalents) of 1-(2-pyrimidinyl)piperazine was added, followed by heating while stirring under reflux for 4 hours.

The reaction treatment was conducted as in Example 19 and purification as in Example 21, to give 5.5 mg of the desired compound (yield 54%). The maleic acid salt was obtained by forming the maleic acid salt in a conventional manner, followed by recrystallization from methylene chloride-ether.

EXAMPLE 81

Synthesis of 7-methoxycarbonyl-4-(4-(4-(2-pyridyl)piperazinyl)butyl)-2,3,4,5-tetrahydro -1,4-benzoxazepine-3,5-dione

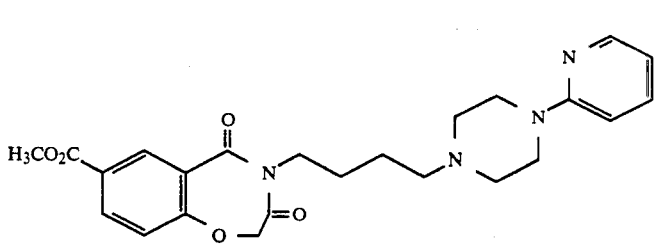

A 60 mg amount of the compound of Example 15 was dissolved in 10 ml of dioxane, and 0.0751 ml (3 equivalents) of 1-(2-pyridyl)piperazine was added, followed by heating while stirring under reflux for hours.

The reaction treatment was conducted as in Example 19 and purification as in Example 21, to give 63.4 mg of the desired compound (yield 87%). The citric acid salt was obtained by forming the citric acid salt in a conventional manner, followed by recrystallization from methylene chloride-ether.

EXAMPLE 82

Synthesis of 7-methoxycarbonyl-4-(4-(4-(2-pyrimidinyl)piperazinyl)-butyl)-2,3,4,5-tetrahydro-1,4-benzoxazepine-3,5-dione

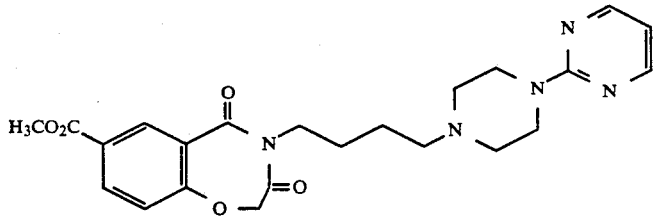

A 60 mg amount of the compound of Example 15 was dissolved in 10 ml of dioxane, and 79.3 mg (3 equivalents) of 1-(2-pyrimidinyl)piperazine was added, followed by heating while stirring under reflux for 6 hours.

The reaction treatment was conducted as in Example 19 and purification as in Example 21, to give 53.1 mg of the desired compound (yield 72%). The maleic acid salt was obtained by forming the maleic acid salt in a conventional manner, followed by recrystallization from methylene chloride-ether.

EXAMPLE 83

Synthesis of 4-(4-(4-(4-methoxy-2-pyrimidinyl)piperazinyl)butyl)-2,3,4,5-tetrahydro-1,4-benzoxazepine-3,5-dione

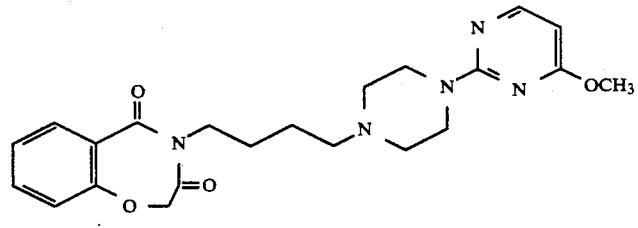

A 326 mg amount of the compound of Example 7 was dissolved in 20 ml of dioxane, and a mixture of 580 mg (3 equivalents) of 1-(4-methoxy-2-pyrimidinyl)piperazine and 1-(2-methoxy-4-pyrimidinyl)piperazine (4:1) was added, followed by refluxing for 15 hours.

The reaction treatment and purification were conducted as in Example 23, to give 271 mg of the desired compound (yield 70.4%). The hydrochloride was obtained by forming the hydrochloride in a conventional manner, followed by recrystallization from ethanol-ether.

EXAMPLE 84

Synthesis of 4-(4-(4-(2-methoxy-4-pyrimidinyl)piperazinyl)butyl)-2,3,4,5-tetrahydro-1,4-benzoxazepine-3,5-dione

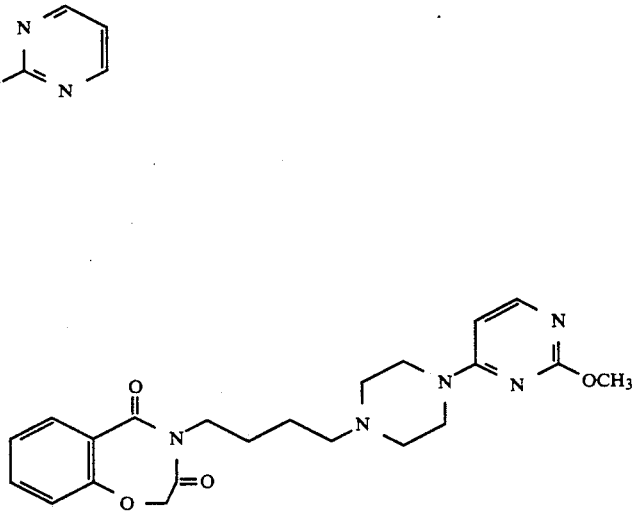

Using the same reaction and purification treatments as in Example 83, 36 mg of the desired product was obtained (yield 8.4%). The hydrochloride was obtained by forming the hydrochloride in a conventional manner, followed by recrystallization from ethanol-ether.

EXAMPLE 85

Synthesis of 4-(4-(4-(2-pyrazinyl)piperazinyl)butyl)-2,3,4,5-tetrahydro-1,4-benzoxazepine-3,5-dione

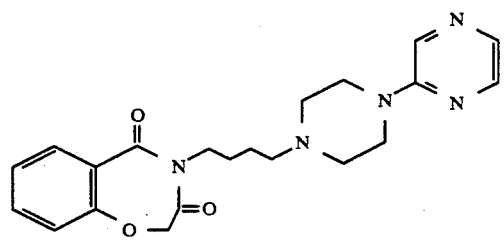

A 326 mg amount of the compound of Example 7 was dissolved in 20 ml of dioxane, and 492 mg (3 equivalents) of 1-pyrazinylpiperazine was added, followed by refluxing for 20 hours.

The reaction treatment and purification were conducted as in Example 23, to give 270 mg of the desired compound (yield 68.3%). The hydrochloride was obtained by forming the hydrochloride in a conventional

EXAMPLE 86

Synthesis of 4-(4-(4-(6-chloro-2-pyrazinyl)piperazinyl)butyl)-2,3,4,5-tetrahydro -1,4-benzoxazepine-3,5-dione

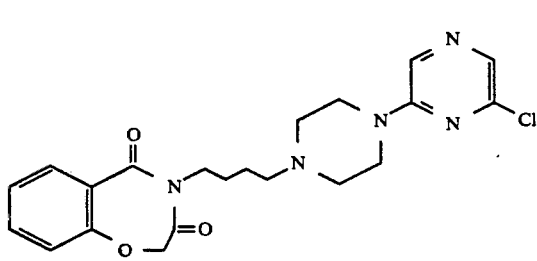

A 163 mg amount of the compound of Example 7 was dissolved in 10 ml of dioxane, and 298 mg (3 equivalents) of 1-(6-chloro-2-pyrazinyl)piperazine was added, followed by refluxing for 18 hours.

The reaction treatment and purification were conducted as in Example 23, to give 194 mg of the desired compound (yield 92.8%). The hydrochloride was obtained by forming the hydrochloride in a conventional manner, followed by recrystallization from ethanol-ether.

EXAMPLE 87

Synthesis of 4-(4-(4-(6-methoxy-2-pyrazinyl)piperazinyl)butyl-2,3,4,5-tetrahydro -1,4-benzoxazepine-3,5-dione

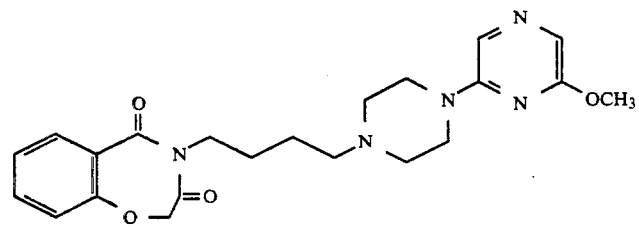

A 130 mg amount of the compound of Example 7 was dissolved in 10 ml of dioxane, and 232 mg (3 equivalents) of 1-(6-methoxy-2-pyrazinyl)piperazine was added, followed by stirring at 100° C. for 20 hours.

The reaction treatment and purification were conducted as in Example 23, to give 158 mg of the desired compound (yield 92.8%). The hydrochloride was obtained by forming the hydrochloride in a conventional manner, followed by recrystallization from methylene ethanol-ether.

EXAMPLE 88

Synthesis of 4-(5-(4-(2-pyridyl)piperazinyl)pentyl)-2,3,4,5-tetrahydro-1,4-benzoxazepine -3,5-dione

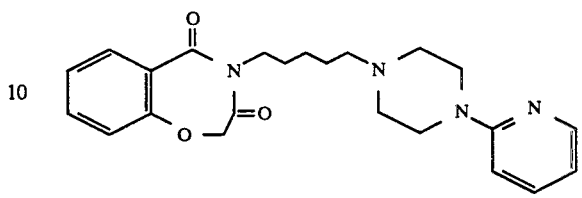

A 70 mg amount of the compound of Example 16 was dissolved in 10 ml of dioxane, and 0.167 ml (5 equivalents) of 1-(2-pyridyl)piperazine was added, followed by heating under stirring at 100° C. for 6 hours.

The reaction treatment was conducted as in Example 19 and purification as in Example 21, to give 79.4 mg of the desired compound (yield 91%). The hydrochloride was obtained by forming the hydrochloride in a conventional manner, followed by recrystallization from methylene chloride-ether.

EXAMPLE 89

Synthesis of 4-(5-(4-(2-pyrimidinyl)piperazinyl) pentyl)-2,3,4,5-tetrahydro-1,4-benzoxazepine-3,5-dione

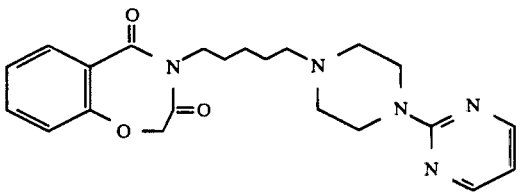

A 70 mg amount of the compound of Example 16 was dissolved in 10 ml of dioxane, and 176 mg (5 equivalents) of 1-(2-pyrimidinyl)piperazine was added, followed by heating under stirring at 100° C. for hours.

The reaction treatment was conducted as in Example 19 and purification as in Example 21, to give 69.2 mg of the title compound (yield 79%). The hydrochloride was obtained by forming the hydrochloride in a conventional manner, followed by recrystallization from methylene chloride-ether.

EXAMPLE 90

Synthesis of
7-methoxy-4-(5-(4-(2-pyridyl)piperazinyl)pentyl)-2,3,4,5-tetrahydro-1,4-benzoxazepine-3,5-dione

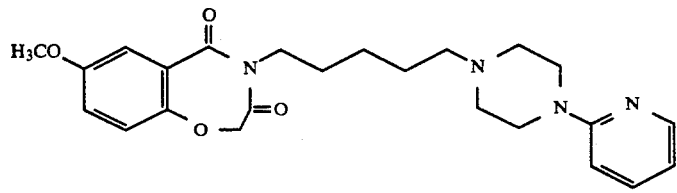

A 106 mg amount of the compound of Example 17 was dissolved in 10 ml of dioxane, and 147 mg (3 equivalents) of 1-(2-pyridyl)piperazine was added, followed by heating under stirring at 90 to 100° C. for 24 hours.

The reaction treatment and purification were conducted as in Example 23, to give 106 mg of the desired compound (yield 80.7%). The hydrochloride was obtained by forming the hydrochloride in a conventional manner, followed by recrystallization from methylene chloride-ether.

EXAMPLE 91

Synthesis of
7-methoxy-4-(5-(4-(2-pyrimidinyl)piperazinyl)pentyl)-2,3,4,5-tetrahydro-1,4-benzoxazepine-3,5-dione

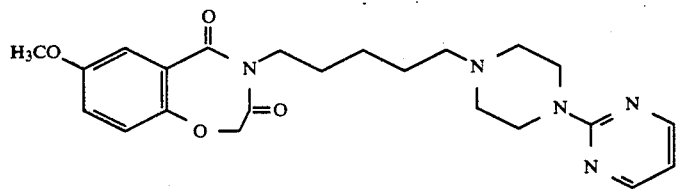

A 106 mg amount of the compound of Example 17 was dissolved in 10 ml of dioxane, and 147 mg (3 equivalents) of 1-(2-pyrimidinyl)piperazine was added, followed by heating under stirring at 90 to 100° C. for 24 hours.

The reaction treatment and purification were conducted as in Example 23, to give 106 mg of the desired compound (yield 80.5%). The hydrochloride was obtained by forming the hydrochloride in a conventional manner, followed by recrystallization from methylene chloride-ether.

EXAMPLE 92

Synthesis of
8-methyl-4-(5-(4-(2-pyridyl)piperazinyl)pentyl)-2,3,4,5-tetrahydro-1,4-benzoxazepine-3,5-dione

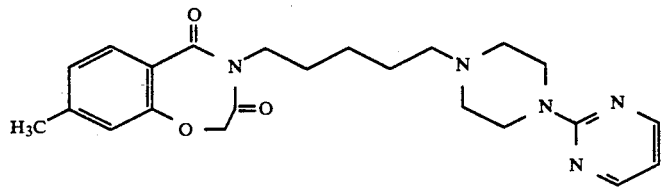

A 136 mg amount of the compound of Example 18 was dissolved in 10 ml of dioxane, and 200 mg (3 equivalents) of 1-(2-pyridyl)piperazine was added, followed by heating under stirring at 90 to 100° C. for 24 hours.

The reaction treatment and purification were conducted as in Example 23, to give 154 mg of the desired compound (yield 91.7%). The hydrochloride was obtained by forming the hydrochloride in a conventional manner, followed by recrystallization from methylene chloride-ether.

EXAMPLE 93

Synthesis of
8-methyl-4-(5-(4-(2-pyrimidinyl)piperazinyl)pentyl)-2,3,4,5-tetrahydro-1,4-benzoxazepine-3,5-di A 136 mg amount of the compound of Example 18 was dissolved in 10 ml of dioxane, and 200 mg (3 equivalents) of 1-(2-pyrimidinyl)piperazine was added, followed by heating under stirring at 90 to 100° C. for 24 hours.

The reaction treatment and purification were conducted as in Example 23, to give 140 mg of the desired compound (yield 83.1%). The hydrochloride was obtained by forming the hydrochloride in a conventional manner, followed by recrystallization from methylene chloride-ether.

EXAMPLE 94

Synthesis of 4-(4-(4-(3-acetylamino-2-pyridyl)piperadine-1-yl)butyl)-2,3,4,5-tetrahydro-1,4-benzoxazepine-3,5-dione

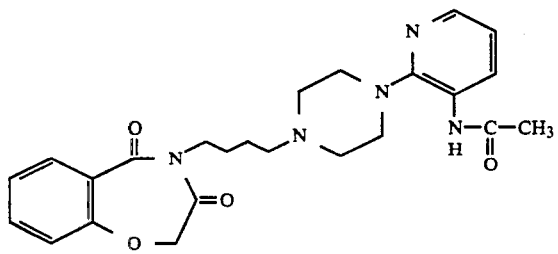

A 340 mg (0.8 mM) amount of the compound of Example 51 was dissolved in 10 ml of methylene chloride, and 252 mg (3.3 mM, 4 equivalent) of pyridine and 163 mg (1.6 mM, 2 equivalent) of acetic anhydride were added, followed by stirring at room temperature for 3 hours.

The solvent was distilled off and ethyl acetate was then added. After washing with water, the organic layer was dried over magnesium sulfate (anhydrous). The organic layer was then filtered and the solvent was distilled off. The residue was eluted with ethyl acetate by using a silica-gel chromatography. Thus, 102 mg of the desired compound was obtained (Yield 28%).

The physical data of the compounds obtained in Examples 19 to 94 as described above is shown in Table 2.

TABLE 2

| Example | m.p. | IR (cm$^{-1}$) | NMR (δ ppm) | Elemental Analysis | | | |
|---|---|---|---|---|---|---|---|
| 19 | 216–217° C. (2HCl salt) | 2930, 2800 1630, 1585 1470, 1430 1305, 1240 1205, 1100 1040, 970 760 | 1.90(quintett, 2H, J=7.2 Hz), 2.49(t, 2H, J=6.6Hz), 2.55–2.59(m, 4H), 3.51–3.56(m, 6H), 3.67(t, 2H, J=7.2Hz), 4.37(t, 2H, J=5.3Hz), 6.59–6.65(m, 2H), 7.00(d, 1H, J=7.9Hz), 7.15 (t, 1H, J=7.9Hz), 7.35–7.50(m, 2H), 7.79(dd, 1H, J=1.3Hz&7.9Hz), 8.17(dd, 1H, J=1.3Hz&5.3Hz) | 2HCl.1H$_2$O calcd. found | C 55.14 55.20 | H 6.61 6.48 | N 12.25 12.38 |
| 20 | 176–178° C. (1HCl salt) | 2930, 2870 2805, 1630 1590, 1555 1470, 1280 1230, 1205 1100, 1040 980, 940 760, 720 | 1.89(quintett, 2H, J=7.3Hz), 2.48(t, 2H, J=7.3Hz), 2.58–2.61(m, 4H), 3.17–3.21(m, 4H), 3.52(t, 2H, J=5.3Hz), 3.66(t, 2H, J=7.3Hz), 4.36(t, 2H, J=5.3Hz), 6.76–6.80(m, 2H), 6.86(s, 1H), 6.99(d, 1H, J=7.9Hz), 7.12–7.18(m, 2H), 7.40(dt, 1H, J=1.3Hz&7.9Hz), 7.80(dd, 1H, J=1.3Hz&7.9Hz) | 1HCl.1H$_2$O calcd. found | C 58.15 58.35 | H 6.43 6.13 | N 9.24 9.30 |
| 21 | 188° C. (2HCl salt) | 2950, 2770 1700, 1645 1590, 1480 1435, 1330 1310, 1290 1240, 1215 1105, 1035 975, 765 | 1.95(quintett, 2H, J=7.3Hz), 2.54(t, 2H, J=7.3Hz), 2.58–2.62(m, 4H), 3.54–3.57(m, 4H), 4.07(t, 2H, J=7.3Hz), 4.76(S, 2H), 6.57–6.65(m, 2H), 7.09(d, 1H, J=8.6Hz), 7.24(t, 1H, J=7.8Hz), 7.44–7.54(m, 2H), 8.15–8.19(m, 2H) | 2HCl.1H$_2$O calcd. found | C 53.50 53.11 | H 5.99 5.43 | N 11.80 11.80 |
| 22 | 208–209° C. (2HCl salt) | 2930, 2800 1705, 1650 1600, 1580 1545, 1480 1445, 1360 1340, 1300 1260, 1215 1120, 1040 980, 795 760, 725 | 1.96(quintett, 2H, J=7.3Hz), 2.52–2.62(m, 6H), 3.80–3.88(m, 4H), 4.07(t, 2H, J=7.3Hz), 4.77(s, 2H), 6.48(t, 1H, J=4.0Hz), 7.10 (d, 1H, J=8.2Hz), 7.25(t, 1H, J=8.2Hz), 7.52(dt, 1H, J=1.3Hz&8.2Hz), 8.16(dd, 1H, J=1.3Hz&8.2Hz), 8.30 (d, 2H, J=4.0Hz) | 2HCl calcd. found | C 52.87 53.24 | H 5.55 5.47 | N 15.42 15.54 |
| 23 | 185–188° C. (2HCl salt) | 2960, 2830 1710, 1660 1600, 1500 1440, 1350 1310, 1270 1240, 1030 780, 720 | 1.91(m, 2H), 2.50(t, 2H, J=7.3Hz), 2.56(t, 4H, J=5.3Hz), 3.53(t, 4H, J=5.3Hz), 3.84(s, 3H), 4.07(t, 2H, J=7.3Hz), 4.71(s, 2H), 6.58–6.64(m, 2H), 6.95–7.08(m, 2H), 7.46(m, 1H), 7.58(d, 1H, J=2.6Hz), 8.18 (dd, 1H, J=2.0Hz, 4.0Hz) | 2HCl.1/2H$_2$O calcd. found | C 53.66 53.91 | H 5.93 5.75 | N 11.39 11.50 |
| 24 | 213–216° C. (2HCl salt) | 2920, 2850 1710, 1660 1610, 1590 | 1.91(m, 2H), 2.46–3.53(m, 6H), 3.81(t, 4H, J=5.3Hz), 3.84(s, 3H), 4.07(t, 2H, J= | 2HCl.1/2H$_2$O calcd. | C 51.12 | H 5.66 | N 14.19 |

TABLE 2-continued

| | | | | | | | | |
|---|---|---|---|---|---|---|---|---|
| | | 1490, 1480 1440, 1360 1290, 1040 835, 800 740, | 7.3Hz), 4.72(s, 2H), 6.46(t, 1H, J=5.3Hz), 6.99-7.09 (m, 2H), 7.57(d, 1H, J= 2.6Hz), 8.29(d, 2H, J= 5.3Hz) | found | 51.36 | 5.72 | 14.39 | |
| 25 | 169-171° C. (2HCl salt) | 2960, 2820 1700, 1650 1590, 1540 1500, 1430 1390, 1360 1280, 1130 980, 760 | 1.90(m, 2H), 2.36(s, 3H), 2.48(t, 2H, J=7.3Hz), 2.54 (t, 4H, J=5.3Hz), 3.50(t, 4H, J=5.3Hz), 4.73(s, 2H), 6.58-6.63(m, 2H), 6.88(s, 1H), 7.03(dd, 1H, J=1.3Hz, 7.3Hz), 7.45(m, 1H), 8.06(d, 1H, J=5.9Hz), 8.17(dd, 1H, J=1.3Hz, 4.6Hz) | 2HCl.5/4H$_2$O calcd. found | C 53.93 53.91 | H 6.28 6.08 | N 11.44 11.47 |
| 26 | 163-165° C. (2HCl salt) | 2940, 2800 1700, 1650 1560, 1470 1450, 1360 1310, 1140 980, 730 | 1.90(m, 2H), 2.38(s, 3H), 2.45-2.49(m, 6H), 3.79(t, 4H, J=5.3Hz), 4.05(t, 2H, J=7.3Hz), 4.72(s, 2H), 6.46 (t, 1H, J=4.6Hz), 6.89(s, 1H), 7.04(d, 1H, J=7.9Hz), 8.07(d, 1H, J=7.9Hz), 8.29 (d, 2H, J=4.6Hz) | 2HCl.1/4H$_2$O calcd. found | C 53.33 52.96 | H 5.86 5.71 | N 14.81 14.72 |
| 27 | 100-101° C. (amine free) | 2930, 2805 1630, 1595 1470, 1435 1375, 1305 1240, 1205 1130, 1105 1040, 975 760, 720 | 1.62-1.74(m, 4H), 2.44(t, 2H, J=6.6Hz), 2.53-2.57 (m, 4H), 3.48(t, 2H, J= 5.3Hz), 3.52-3.56(m, 4H), 3.63(t, 2H, J=7.3Hz), 4.35 (t, 2H, J=5.3Hz), 6.60(dd, 1H, J=4.6&7.3Hz), 6.63(d, 1H, J=7.9Hz), 6.99(d, 1H, J=8.6Hz), 7.14(dd, 1H, J= 7.9&7.2Hz), 7.39(ddd, 1H, J=1.3&7.2&8.6Hz), 7.46 (dd, 1H, J=7.9&7.3Hz), 7.78(dd, 1H, J=1.3& 7.9Hz), 8.17(d, 1H, J= 4.6Hz) | 1/4H$_2$O calcd. found | C 68.63 68.54 | H 7.46 7.37 | N 14.55 14.65 |
| 28 | 171-172° C. (3HCl salt) | 2930, 2850 2800, 1630 1585, 1540 1470, 1445 1360, 1305 1260, 1210 1125, 1040 980, 795 760, 720 | 1.63-1.71(m, 4H), 2.47(t, 2H, J=6.6Hz), 2.52-2.55 (m, 4H), 3.50(t, 2H, J= 5.3Hz), 3.65(t, 2H, J= 6.6Hz), 3.83-3.87(m, 4H), 4.37(t, 2H, J=5.3Hz), 6.48 (t, 1H, J=4.6Hz), 6.99(d, 1H, J=7.9Hz), 7.16(t, 1H, J=7.9Hz), 7.38(dt, 1H, J= 2.0&7.9Hz), 7.79(dd, 1H, J=2.0&7.9Hz), 8.30(d, 2H, J=4.6Hz) | 3HCl calcd. found | C 51.38 51.28 | H 6.16 6.18 | N 14.27 13.91 |
| 29 | 210-212° C. (1HCl salt) | 2930, 2810 1640, 1595 1560, 1470 1235, 1205 1130, 1100 1040, 980 940, 760 | 1.60-1.71(m, 4H), 2.46(t, 2H, J=7.3Hz), 2.57-2.61 (m, 4H), 3.18-3.22(m, 4H), 3.49(t, 2H, J=5.3Hz), 3.64 (t, 2H, J=7.2Hz), 4.36(t, 2H, J=5.3Hz), 6.75-6.81 (m, 2H), 6.88(s, 1H), 7.00(d, 1H, J=7.9Hz, H-9), 7.12- 7.18(m, 2H), 7.40(dt, 1H, J= 1.3Hz&7.9Hz), 7.79(dd, 1H, J=1.3Hz&7.3Hz) | 1HCl calcd. found | C 61.33 60.93 | H 6.49 6.42 | N 9.33 9.29 |
| 30 | 208-210° C. (2HCl salt) | 2930, 2800 1640, 1600 1495, 1460 1300, 1235 1200, 1125 1105, 1035 1020, 740 | 1.62-1.75(m, 4H), 2.48(t, 2H, J=6.6Hz), 2.57-2.80 (m, 4H), 2.99-3.43(m, 4H), 3.49(t, 2H, J=5.3Hz), 3.64 (t, 2H, J=6.6Hz), 3.85(s, 3H), 4.36(t, 2H, J=5.3Hz), 6.84-7.02(m, 5H), 7.14(t, 1H, J=7.3Hz), 7.39(dt, 1H, J=1.3Hz&7.3Hz), 7.79(dd, 1H, J=1.3&7.3Hz) | 2HCl.1H$_2$O calcd. found | C 57.60 57.80 | H 7.05 6.89 | N 8.40 8.44 |
| 31 | 90-115° C. Hygroscopic (2HCl salt) | 2920, 2800 1665, 1595 1485, 1435 1310, 1240 1130, 1055 1020, 980 770 | 1.50-1.67(m, 4H), 2.40(t, 2H, J=7.3Hz), 2.50-2.54 (m, 4H), 3.53-3.60(m, 6H), 4.49(s, 2H), 4.69(s, 2H), 6.59-6.65(m, 2H), 7.03- 7.07(m, 2H), 7.16(dd, 1H, J= 2.0&7.9Hz), 7.29(dt, 1H, J=2.0&7.6Hz), 7.47(dt, 1H, J=7.2&2.0Hz), 8.18(dd, 1H, J=4.6&2.0Hz) | 2HCl.3/2H$_2$O calcd. found | C 55.00 55.07 | H 6.92 6.64 | N 11.66 11.77 |
| 32 | 198.5-199.0° C. (1HCl salt) | 2930, 2850 2800, 1665 | 1.54-1.70(m, 4H), 2.47- 2.54(m, 6H), 3.58(t, 2H, J= | 1HCl.1H$_2$O | C | H | N | |

| | | | | | | | |
|---|---|---|---|---|---|---|---|
| | | 1635, 1590 1545, 1490 1445, 1360 1305, 1260 1220, 1190 1135, 1055 1020, 980 795, 755 | 6.6Hz), 3.84–3.95(m, 4H), 4.51(s, 2H), 4.70(s, 2H), 6.50(t, 1H, J=4.6Hz), 7.03–7.09(m, 2H), 7.17(d, 1H, J=7.2Hz), 7.29(t, 1H, J=7.0Hz), 8.31(d, 2H, J=4.6Hz) | | calcd. found | 57.85 6.94 16.07 57.58 6.49 16.04 | |
| 33 | 214.0–215.0° C. (1HCl salt) | 2920, 2800 1660, 1645 1585, 1480 1440, 1220 1130, 1045 1015, 980 940, 750 | 1.52–1.68(m, 4H), 2.47(t, 2H, J=6.6Hz), 2.60–2.61 (m, 4H), 3.21–3.25(m, 4H), 3.58(t, 2H, J=6.7Hz), 4.50 (s, 2H), 4.70(s, 2H), 6.75–6.83(m, 2H), 6.87(d, 1H, J=2.0Hz), 7.03–7.07(m, 2H), 7.13–7.19(m, 2H), 7.30(dt, 1H, J=1.3Hz&7.9Hz) | 1HCl.1/2H$_2$O | calcd. found | C 60.13 60.20 | H 6.58 6.37 | N 9.15 9.16 |
| 34 | 205–207° C. (HCl salt) | 2950, 2830 1700, 1650 1600, 1350 1300, 1230 1120, 1060, 910, 780 760 | 1.54–1.74(m, 4H), 2.43 (t, 2H, J=7.3Hz), 2.60(t, 4H, J=5.3Hz), 3.20(t, 4H, J=5.3Hz), 4.02(t, 2H, J=7.3Hz), 4.76(s, 2H), 6.84(t, 1H, J=7.2Hz), 6.93(d, 2H, J=7.9Hz), 7.10(d, 1H, J=7.9Hz), 7.21–7.29(m, 3H), 7.51(m, 1H), 8.16(dd, 1H, J=1.3Hz, 7.9Hz) | 1HCl.H$_2$O | calcd. found | C 61.67 61.34 | H 6.74 6.34 | N 9.38 9.31 |
| 35 | 189–192° C. (1HCl salt) | 2930, 2800 1705, 1650 1605, 1500 1480, 1450 1370, 1360 1340, 1290 1235, 1210 1125, 1060 1040, 925 750 | 1.53–1.76(m, 4H), 2.44(t, 2H, J=7.6Hz), 2.62(t, 4H, J=4.9Hz), 3.11(t, 4H, J=4.9Hz), 4.02(t, 2H, J=7.6Hz), 4.75(s, 2H), 6.91–7.24(m, 6H), 7.51(dt, 1H, J=1.3Hz&7.6Hz), 8.16(dd, 1H, J=1.3Hz&7.6Hz) | 1HCl.1/2H$_2$O | calcd. found | C 60.38 60.80 | H 6.17 6.03 | N 9.19 9.23 |
| 36 | 179–181° C. (1HCl salt) | 2930, 2800 1700, 1650 1600, 1580 1475, 1440 1360, 1330 1280, 1220 1115, 1035 920, 755 720, 680 | 1.56–1.74(m, 4H), 2.45(t, 2H, J=7.2Hz), 2.58–2.66 (m, 4H), 3.06–3.09(m, 4H), 4.02(t, 2H, J=7.3Hz), 4.75 (s, 2H), 6.95–7.36(m, 6H), 7.51(dt, 1H, J=2.0Hz& 7.9Hz), 8.16(dd, 1H, J=2.0Hz&7.9Hz) | 1HCl.1/4H$_2$O | calcd. found | C 58.91 58.89 | H 5.91 5.79 | N 8.96 8.95 |
| 37 | 200.5–202.5° C. (1HCl salt) | 2930, 2800 1700, 1650 1600, 1495 1480, 1450 1290, 1235 1120, 1020 745 | 1.70–1.80(m, 4H), 2.60–2.72(m, 2H), 2.78–2.92(m, 4H), 3.18–3.30(m, 4H), 3.86 (s, 3H), 4.02(t, 2H, J=7.3Hz), 4.76(s, 2H), 6.85–7.05(m, 4H), 7.10(d, 1H, J=7.9Hz), 7.24(t, 1H, J=7.9Hz), 7.51(dt, 1H, J=1.3Hz&7.9Hz), 8.16(dd, 1H, J=1.3Hz&7.9Hz) | 1HCl.3/2H$_2$O | calcd. found | C 59.19 59.20 | H 6.42 6.45 | N 8.63 8.60 |
| 38 | 227–228° C. (1HCl salt) | 3300, 2940 2810, 1700 1645, 1600 1590, 1485 1455, 1360 1340, 1295 1245, 1220 1060, 1040 1020, 925 820, 780 750, 690 | 1.55–1.77(m, 4H), 2.46(t, 2H, J=7.3Hz, 2.62(t, 4H, J=4.6Hz), 2.90(t, 4H, J=4.6Hz), 4.03(t, 2H, J=7.3Hz), 4.76(s, 2H), 6.82–7.24(m, 6H), 7.52(dt, 1H, J=2.0Hz&7.6Hz), 8.17(dd, 1H, J=2.0Hz&7.6Hz) | 1HCl.1/4H$_2$O | calcd. found | C 61.32 61.26 | H 6.38 6.22 | N 9.33 9.34 |
| 39 | 170–172° C. (1HCl salt) | 2930, 2805 1705, 1650 1595, 1485 1455, 1290 1205, 1110 980, 940 760 | 1.63–1.80(m, 4H), 2.52–2.83(m, 6H), 3.22–3.38(m, 4H), 4.02(t, 2H, J=7.2Hz), 4.76(s, 2H), 6.76–6.84(m, 2H), 6.87(s, 1H), 7.05–7.25 (m, 3H), 7.52(dt, 1H, J=1.3Hz&7.9Hz), 8.16(dd, 1H, J=1.3Hz&8.0Hz) | 1HCl.5/4H$_2$O | calcd. found | C 56.73 56.59 | H 6.11 5.60 | N 8.63 8.62 |
| 40 | 189–191° C. (2HCl salt) | 2930, 2810 1700, 1645 1600, 1570 1480, 1445 1330, 1290 1250, 1200 1165, 1125 | 1.54–1.73(m, 4H), 2.44(t, 2H, J=7.2Hz), 2.59(t, 4H, J=4.9Hz), 2.19(t, 4H, J=4.9Hz), 3.78(s, 3H), 4.01(t, 2H, J=7.2Hz), 4.75(s, 2H), 6.38–6.57(m, 3H), 7.08–7.23(m, 3H), 7.51(dt, 1H, J= | 2HCl | calcd. found | C 58.30 58.57 | H 5.91 6.25 | N 8.50 8.55 |

TABLE 2-continued

| | | 1045, 985<br>965, 905<br>835, 760<br>720, 680 | 2.0Hz&8.6Hz), 8.16(dd, 1H,<br>J=2.0Hz&8.6Hz) | | | | |
|---|---|---|---|---|---|---|---|
| 41 | 181–182° C.<br>(1HCl salt) | 2930, 2800<br>1700, 1645<br>1595, 1480<br>1445, 1290<br>1240, 1210<br>1180, 1120<br>1040, 990<br>945, 760<br>680 | 1.49–1.76(m, 4H), 2.31(s,<br>3H), 2.43(t, 2H, J=7.6Hz),<br>2.59(t, 4H, J=4.9Hz), 3.18<br>(t, 4H, J=4.9Hz), 4.02(t,<br>2H, J=7.6Hz), 4.75(s, 2H),<br>6.66–6.72(m, 2H), 6.75(s,<br>1H), 7.08–7.30(m, 3H), 7.51<br>(dt, 1H, J=1.3Hz&6.9Hz),<br>8.16(dd, 1H, J=1.3Hz&<br>6.9Hz) | 1HCl.1/4H$_2$O<br>calcd.<br>found | C<br>64.27<br>64.32 | H<br>6.86<br>6.77 | N<br>9.37<br>9.41 |
| 42 | 157–160° C.<br>(1HCl salt) | 2930, 2810<br>1705, 1650<br>1600, 1480<br>1450, 1390<br>1350, 1315<br>1290, 1220<br>1160, 1120<br>1070, 990<br>940, 860<br>820, 780<br>760, 720,<br>690 | 1.61–1.74(m, 4H), 2.50(t,<br>2H, J=7.0Hz), 2.63–2.70<br>(m, 4H), 3.24–3.30(m, 4H),<br>4.02(t, 2H, J=7.0Hz), 4.76<br>(s, 2H), 7.04–7.37(m, 6H),<br>7.52(dt, 1H, J=1.6Hz&<br>7.6Hz), 8.16(dd, 1H, J=<br>1.6Hz&7.6Hz) | 1HCl.1/2H$_2$O<br>calcd.<br>found | C<br>56.86<br>56.40 | H<br>5.57<br>5.29 | N<br>8.29<br>8.28 |
| 43 | 181–182° C.<br>(2HCl salt) | 2940, 2800<br>1700, 1645<br>1600, 1505<br>1480, 1450<br>1335, 1290<br>1220, 1120<br>1035, 915<br>810, 760<br>700 | 1.54–1.77(m, 4H), 2.45(t,<br>2H, J=7.3Hz), 2.61(t, 4H,<br>J=5.3Hz), 3.12(t, 4H, J=<br>5.3Hz), 4.02(t, 2H, J=<br>7.3Hz), 4.75(s, 2H), 6.84–<br>7.00(m, 4H), 7.09(d, 1H, J=<br>7.2Hz), 7.24(t, 1H, J=<br>7.2Hz), 7.52(dt, 1H, J=<br>2.0Hz&7.2Hz), 8.16(dd, 1H,<br>J=2.0Hz&7.2Hz) | 2HCl, 1/4H$_2$O<br>calcd.<br>found | C<br>56.50<br>56.59 | H<br>5.88<br>5.65 | N<br>8.60<br>8.59 |
| 44 | 207–208° C.<br>(1HCl salt) | 2950, 2780<br>1700, 1650<br>1600, 1485<br>1450, 1390<br>1360, 1340<br>1290, 1230<br>1115, 1060<br>990, 910<br>810, 760 | 1.50–1.74(m, 4H), 2.43(t,<br>2H, J=7.3Hz), 2.58(t, 4H,<br>J=4.9Hz), 3.15(t, 4H, J=<br>4.9Hz), 4.02(t, 2H, J=<br>7.3Hz), 4.75(s, 2H), 6.83(d,<br>2H, J=9.2Hz), 7.10(d, 1H,<br>J=7.9Hz), 7.19(d, 2H, J=<br>9.2Hz), 7.24(t, 1H, J=<br>7.9Hz), 7.52(dt, 1H, J=<br>1.6Hz&7.9Hz), 8.16(dd, 1H,<br>J=1.6Hz&7.9Hz) | 1HCl.3/2H$_2$O<br>calcd.<br>found | C<br>56.21<br>56.18 | H<br>6.15<br>5.61 | N<br>8.55<br>8.58 |
| 45 | 200–202° C.<br>(2HCl salt) | 2930, 2800<br>1700, 1640<br>1600, 1500<br>1480, 1450<br>1340, 1290<br>1240, 1210<br>1180, 1150<br>1120, 1050<br>1035, 910<br>820, 765 | 1.53–1.76(m, 4H), 2.44(t,<br>2H, J=7.2Hz), 2.60(t, 4H,<br>J=4.9Hz), 3.09(t, 4H, J=<br>4.9Hz), 3.75(s, 3H), 4.01(t,<br>2H, J=7.2Hz), 4.74(s, 2H),<br>6.82(dd, 2H, J=2.6Hz&<br>9.2Hz), 6.89(dd, 2H, J=<br>2.0Hz&9.2Hz), 7.08(d, 1H,<br>J=7.9Hz), 7.23(t, 1H, J=<br>7.9Hz), 7.50(dt, 1H, J=<br>1.3Hz&7.9Hz), 8.15(dd, 1H,<br>J=1.3Hz&7.9Hz) | 2HCl<br>calcd.<br>found | C<br>58.30<br>58.29 | H<br>5.91<br>6.25 | N<br>8.50<br>8.49 |
| 46 | 208–210° C.<br>(1HCl salt) | 2940, 2800<br>1700, 1650<br>1600, 1480<br>1450, 1420<br>1360, 1290<br>1225, 1190<br>1120, 1055<br>950, 915<br>815, 760 | 1.54–1.77(m, 4H), 2.44(t,<br>2H, J=7.3Hz), 2.52(s, 3H),<br>2.59(t, 4H, J=4.9Hz), 3.36<br>(t, 4H, J=4.9Hz), 4.02(t,<br>2H, J=7.3Hz), 4.76(s, 2H),<br>6.86(d, 2H, J=8.6Hz), 7.10<br>(d, 1H, J=7.9Hz), 7.24(t,<br>1H, J=7.9Hz), 7.52(dt, 1H,<br>J=1.3Hz&7.9Hz), 7.86(d,<br>2H, J=8.6Hz), 8.16(dd, 1H,<br>J=1.3Hz&7.9Hz) | 1HCl<br>calcd.<br>found | C<br>63.61<br>63.46 | H<br>6.41<br>6.34 | N<br>8.90<br>8.78 |
| 47 | 180–183° C.<br>(2HCl salt) | 2900, 2780<br>1700, 1640<br>1585, 1475<br>1430, 1285<br>1240, 1120<br>975, 760 | 1.66–1.78(m, 4H), 2.52–<br>2.82(m, 6H), 3.60–3.77(m,<br>4H), 4.01(t, 2H, J=6.6Hz),<br>4.76(s, 2H), 6.63–6.67(m,<br>2H), 7.09(d, 1H, J=7.9Hz),<br>7.24(t, 1H, J=7.9Hz), 7.46–<br>7.55(m, 2H), 8.14–8.20<br>(m, 2H) | 2HCl.1H$_2$O<br>calcd.<br>found | C<br>54.43<br>54.19 | H<br>6.23<br>5.98 | N<br>11.54<br>11.56 |
| 48 | 135–137° C.<br>(2HCl salt) | 2950, 2820<br>1710, 1660<br>1605, 1580<br>1240, 1120 | 1.56–1.73(m, 4H), 2.44(t,<br>2H, J=7.3Hz), 2.60(t, 4H,<br>J=4.6Hz), 3.39(t, 4H,<br>4.6Hz), 4.02(t, 2H, J= | 2HCl.H$_2$O<br>calcd.<br>found | C<br>50.83<br>50.66 | H<br>5.62<br>5.54 | N<br>10.78<br>10.79 |

TABLE 2-continued

| | | | | | |
|---|---|---|---|---|---|
| | | 1030, 950
790, 700 | 7.3Hz), 4.75(s, 2H), 6.81 (dd, 1H, J=4.6Hz, 7.9Hz), 7.09(dd, 1H, J=1.3Hz, 7.3Hz), 7.24(m, 1H), 7.48–7.58(m, 2H), 8.14–8.17 (m, 2H) | | |
| 49 | 185–187° C. (1HCl salt) | 2900, 2800 1710, 1600 1550, 1220 1040, 940 850, 750 | 1.51–1.75(m, 4H), 2.42(t, 2H, J=7.3Hz), 2.53(t, 4H, J=5.3Hz), 3.46(t, 4H, J=5.3Hz), 4.01(t, 2H, J=7.3Hz), 4.75(s, 2H), 6.71 (dd, 1H, J=4.6Hz, 7.9Hz), 7.08(dd, 1H, J=1.3Hz, 7.9Hz), 7.24(m, 1H), 7.51(m, 1H), 8.10(dd, 1H, J=1.3Hz, 7.9Hz), 8.16(dd, 1H, J=1.3Hz, 7.9Hz), 8.31(dd, 1H, J=1.3Hz, 4.6Hz) | HCl.1/4H$_2$O<br>　　　　C　　H　　N<br>calcd.　55.00　5.56　14.58<br>found　54.74　5.42　14.48 | |
| 50 | 194–196° C. (1HCl salt) | 2930, 2205 1700, 1650 1600, 1580 1550, 1480 1440, 1290 1220, 1120 1050, 950 760 | 1.52–1.76(m, 4H), 2.43(t, 2H, J=7.3Hz), 2.58(t, 4H, J=5.3Hz), 3.74(t, 4H, J=5.3Hz), 4.02(t, 2H, J=7.9Hz), 4.75(s, 2H), 6.72 (dd, 1H, J=4.6Hz, 7.3Hz), 7.09(dd, 1H, J=1.3Hz, 7.3Hz), 7.24(m, 1H), 7.52(m, 1H), 7.75(dd, 1H, J=1.9Hz, 7.3Hz), 8.16(dd, 1H, J=1.3Hz, 7.9Hz), 8.32(dd, 1H, J=1.9Hz, 4.6Hz) | HCl.3/2H$_2$O<br>　　　　C　　H　　N<br>calcd.　57.19　6.05　14.50<br>found　57.01　5.65　14.51 | |
| 51 | 196–200° C. (2HCl salt) | 3400–3100 1700, 1640 1590, 1540 1440, 1350 1290, 1210 1190, 1120 1020, 930 790, 730 | 1.53–1.76(m, 4H), 2.44(t, 2H, J=7.3Hz), 2.60(bs, 4H), 3.14(t, 4H, J=5.3Hz), 3.75 (bs, 2H), 4.02(t, 2H, J=7.3Hz), 4.75(s, 2H), 6.81 (dd, 1H, J=4.6Hz, 7.3Hz), 6.92(dd, 1H, J=1.3Hz, 7.3Hz), 7.09(dd, 1H, J=1.3Hz, 7.9Hz), 7.23(m, 1H), 7.51(m, 1H), 7.78(dd, 1H, J=1.3Hz, 7.9Hz), 8.16(dd, 1H, J=1.3Hz, 7.9Hz) | 2HCl.1/2H$_2$O<br>　　　　C　　H　　N<br>calcd.　53.77　6.15　14.25<br>found　53.77　6.46　13.29 | |
| 52 | 145–147° C. (2HCl salt) | 2900, 2750 1700, 1640 1580, 1480 1440, 1355 1285, 1255 1210, 1120 975, 790 | 1.52–1.70(m, 4H), 2.52–2.73(m, 6H), 3.82–4.07(m, 6H), 4.76(s, 2H), 6.51(t, 1H, J=4.6Hz), 7.10(d, 1H, J=7.9Hz), 7.25(t, 1H, J=7.9Hz), 7.52(t, 1H, J=7.9Hz), 8.16(d, 1H, J=7.9Hz), 8.31(d, 2H, J=4.6Hz) | 2HCl.1/2H$_2$O<br>　　　　C　　H　　N<br>calcd.　52.83　5.91　14.67<br>found　52.70　5.73　14.78 | |
| 53 | 185–186° C. (2HCl salt) | 2950, 2840 1720, 1660 1600, 1500 1390, 1070 1030, 810 770 | 1.56–1.76(m, 4H), 2.44(t, 2H, J=7.3Hz), 2.57(t, 4H, J=5.3Hz), 3.56(t, 4H, J=5.3Hz), 3.84(s, 3H), 4.02(t, 2H, J=7.3Hz), 4.72(s, 2H), 6.59–66.5(m, 2H), 6.99–7.09(m, 2H), 7.47(m, 1H), 7.57(d, 1H, J=1.9Hz), 8.17 (dd, 1H, J=1.9Hz, 5.3Hz) | 2HCl.1/2H$_2$O<br>　　　　C　　H　　N<br>calcd.　54.54　6.16　11.06<br>found　54.84　5.95　11.11 | |
| 54 | 183–185° C. (2HCl salt) | 2940, 2830 1700, 1640 1600, 1570 1490, 1430 1280, 1110 1020, 940 | 1.53–1.76(m, 4H), 2.45(t, 2H, J=7.3Hz), 2.61(t, 4H, J=5.3Hz), 3.38(t, 4H, J=5.3Hz), 3.84(s, 3H), 4.02(t, 2H, J=7.3Hz), 4.72(s, 2H), 6.81(dd, 1H, J=4.6Hz, 7.9Hz), 6.99–7.09(m, 2H), 7.54–7.59(m, 2H), 8.17(dd, 1H, J=1.3Hz, 4.6Hz) | 2HCl<br>　　　　C　　H　　N<br>calcd.　51.94　5.50　10.53<br>found　51.98　5.45　10.56 | |
| 55 | 193–196° C. (1HCl salt) | 2940, 2800 1705, 1650 1590, 1550 1400, 1290 1120,1030 950,850 760 | 1.52–1.75(m, 4H), 2.43(t, 2H, J=7.3Hz), 2.54(t, 4H, J=5.3Hz), 3.47(t, 2H, J=7.3Hz), 3.84(s, 3H), 4.01(t, 2H, J=7.3Hz), 4.72(s, 2H), 4.6Hz, 7.9Hz), 7.57(d, 1H, J=2.6Hz), 8.10 (dd, 1H, J=1.3Hz, 7.9Hz), 8.31(dd, 1H, J=1.3Hz, 4.6Hz) | HCl.1/4H$_2$O<br>　　　　C　　H　　N<br>calcd.　54.11　5.63　13.72<br>found　54.17　5.53　13.70<br>6.99–7.-10(m, 2H), | |

TABLE 2-continued

| | | | | | | | |
|---|---|---|---|---|---|---|---|
| 56 | 189–190° C. (HCl salt) | 2950, 2800 2220, 1710 1650, 1590 1550, 1500 1290, 1140 1040, 950 830 | 1.53–1.74(m, 4H), 2.44(t, 2H, J=7.3Hz), 2.58(t, 4H, J=5.3Hz), 3.74(t, 4H, J=5.3Hz), 3.84(s, 3H), 4.02(t, 2H, J=7.3Hz), 4.72(s, 2H), 6.73(dd, 1H, J=4.6Hz, 7.9Hz), 7.00–7.09(m, 2H), 7.58(d, 1H, J=2.6Hz), 7.75 (dd, 1H, J=2.0Hz, 7.9Hz), 8.33(dd, 1H, J=2.0Hz, 4.6Hz) | HCl.1/4H$_2$O | C | H | N |
| | | | | calcd. | 58.77 | 5.86 | 14.28 |
| | | | | found | 58.69 | 5.90 | 14.25 |
| 57 | 197–201° C. (1HCl salt) | 3500–3100 2950, 2830 1700, 1650 1600, 1390 1350, 1290 1130, 1030 940, 730 | 1.54–1.76(m, 4H), 2.45(t, 2H, J=7.3Hz), 2.60(bs, 4H), 3.14(t, 4H, J=5.3Hz), 3.76 (bs, 2H), 3.84(s, 3H), 4.02 (t, 2H, J=7.3Hz), 4.72(s, 2H), 6.81(dd, 1H, J=4.6Hz, 7.9Hz), 6.92(dd, 1H, J=1.3Hz, 7.9Hz), 6.99–7.09 (m, 2H), 7.57(d, 1H, J=3.3Hz), 7.78(dd, 1H, J=1.3Hz, 4.6Hz) | HCl, 3/2H$_2$O | C | H | N |
| | | | | calcd. | 52.77 | 6.55 | 13.38 |
| | | | | found | 52.80 | 6.20 | 13.20 |
| 58 | 186–189° C. (1HCl salt) | 2940, 2830 1710, 1650 1590, 1500 1450, 1360 1290, 1260 1210, 980 800 | 1.55–1.76(m, 4H), 2.44(t, 2H, J=7.3Hz), 2.52(t, 4H, J=5.3Hz), 3.83(t, 4H, J=5.3Hz), 3.84(s, 3H), 4.02(t, 2H, J=7.3Hz), 6.45(t, 1H, J=4,6Hz), 6.99–7.10(m, 2H), 7.57(d, 1H, J=3.3Hz), 8.29 (d, 2H, J=4.6Hz) | HCl.1/2H$_2$O | C | H | N |
| | | | | calcd. | 56.11 | 6.20 | 14.87 |
| | | | | found | 56.51 | 5.97 | 14.99 |
| 59 | 197–199° C. (2HCl salt) | 2930, 2800 1705, 1650 1595, 1560 1480, 1435 1405, 1310 1280, 1240 1130, 1080 1045, 975 820, 765 725, 690 | 1.52–1.75(m, 4H), 2.41(t, 2H, J=7.2Hz), 2.54 (t, 4H, J=5.1Hz), 3.53(t, 4H, J=5.1Hz), 4.00(t, 2H, J=7.2Hz), 4.74(s, 2H), 6.58–6.65(m, 2H), 7.11(d, 1H, J=2.0Hz), 7.21(dd, 1H, J=2.0Hz&9.2Hz), 7.46(dt, 1H, J=2.0Hz&7.9Hz), 8.12(d, 1H, J=9.2Hz), 8.18(dd, 1H, J=2.0Hz&4.6Hz) | 2HCl.1/2H$_2$O | C | H | N |
| | | | | calcd. | 51.72 | 5.52 | 10.97 |
| | | | | found | 51.35 | 5.21 | 10.84 |
| 60 | 157–159° C. (2HCl salt) | 2940, 2800 1710, 1650 1600, 1575 1440, 1410 1370, 1310 1280, 1240 1130, 1080 1030, 945 820, 780 760, 690 | 1.53–1.75(m, 4H), 2.44(t, 2H, J=7.3Hz), 2.60(t, 4H, J=4.6Hz), 3.38(t, 4H, J=4.6Hz), 4.00(t, 2H, J=7.3Hz), 4.75(s, 2H), 6.81 (dd, 1H, J=4.6Hz&7.3Hz), 7.12(d, 1H, J=2.6Hz), 7.21 (dd, 1H, J=2.6Hz&8.6Hz), 7.57(dd, 1H, J=1.8Hz&7.3Hz), 8.13(d, 1H, J=8.6Hz), 8.17(dd, 1H, J=1.8Hz&4.6Hz) | 2HCl.1/2H$_2$O | C | H | N |
| | | | | calcd. | 48.45 | 4.99 | 10.28 |
| | | | | found | 48.40 | 4.91 | 10.13 |
| 61 | 176–183° C. (2HCl salt) | 2930, 2810 1730, 1710 1650, 1595 1550, 1500 1440, 1410 1330, 1280 1240, 1130 1080, 1040 945, 850 800, 755 | 1.53–1.72(m, 4H), 2.42(t, 2H, J=7.2Hz), 2.53(t, 4H, J=4.9Hz), 3.47(t, 4H, J=4.9Hz), 3.99(t, 2H, J=7.2Hz), 4.75(s, 2H), 6.73(dd 1H, J=4.6Hz&7.9Hz), 7.13 (d, 1H, J=2.0Hz), 7.22(dd, 1H, J=2.0Hz&9.2Hz), 8.11 (dd, 1H, J=2.0Hz&7.9Hz), 8.13(d, 1H, J=9.2Hz), 8.31 (dd, 1H, J=2.0Hz&4.6Hz) | 2HCl.1/4H$_2$O | C | H | N |
| | | | | calcd. | 47.92 | 4.84 | 12.70 |
| | | | | found | 48.39 | 4.87 | 12.28 |
| 62 | 202–203° C. (2HCl salt) | 2930, 2810 2220, 1710 1650, 1590 1550, 1440 1410, 1360 1280, 1230 1135, 1085 1050, 945 890, 830 790, 760 | 1.51–1.75(m, 4H), 2.43(t, 2H, J=7.2Hz), 2.58(t, 4H, J=4.9Hz), 3.74(t, 4H, J=4.9Hz), 4.00(t, 2H, J=7.2Hz), 4.75(s, 2H), 6.73 (dd, 1H, J=4.6Hz&7.9Hz), 7.12(d, 1H, J=2.0Hz), 7.22 (dd, 1H, J=2.0Hz&8.6Hz), 7.75(dd, 1H, J=2.0Hz&7.9Hz), 8.13(d, 1H, J=8.6Hz), 8.33(dd, 1H, J=2.0Hz&4.6Hz) | 2HCl.1H$_2$O | C | H | N |
| | | | | calcd. | 50.70 | 5.16 | 12.67 |
| | | | | found | 50.75 | 5.16 | 12.67 |
| 63 | 129–131° C. (2HCl salt) | 3400, 3320 2930, 2810 1730, 1710 | 1.56–1.73(m, 4H), 2.44(t, 2H, J=7.3Hz), 2.60(t, 4H, J=4.6Hz), 3.15(t, 4H, J= | 2HCl.2H$_2$O | C | H | N |
| | | | | calcd. | 47.79 | 5.83 | 12.67 |

| No. | mp | IR | NMR | Analysis |
|---|---|---|---|---|
| | | 1650, 1600<br>1450, 1410<br>1370, 1280<br>1230, 1130<br>1080, 1040<br>940, 890<br>790, 770<br>730, 690 | 4.6Hz), 3.74(s, 2H), 4.00(t,<br>2H, J=7.3Hz), 4.75(s, 2H),<br>6.82(dd, 1H, J=4.6Hz&<br>7.6Hz), 6.93(dd, 1H, J=<br>1.4Hz&7.6Hz), 7.12(d, 1H,<br>J=2.0Hz), 7.22(dd, 1H, J=<br>2.0Hz&8,6Hz), 7.79(dd, 1H,<br>J=1.4Hz&4.6Hz), 8.13(d,<br>1H, J=8.6Hz) | found   48.19   5.70   11.88 |
| 64 | 181–184° C.<br>(2HCl salt) | 2940, 2810<br>1710, 1650<br>1600, 1540<br>1500, 1440<br>1360, 1310<br>1280, 1215<br>1130, 1085<br>1055, 980<br>800, 760<br>730 | 1.52–1.72(m, 4H), 2.41(t,<br>2H, J=7.3Hz), 2.49(t, 4H,<br>J=5.3Hz), 3.82(t, 4H, J=<br>5.3Hz), 4.00(t, 2H, J=<br>7.3Hz), 4.75(s, 2H), 6.47(t,<br>1H, J=4.6Hz), 7.12(d, 1H,<br>J=2.0Hz), 7.21(dd, 1H, J=<br>2.0Hz&8.6Hz), 8.13(d, 1H,<br>J=8.6Hz), 8.29(d, 2H, J=<br>4.6Hz) | 2HCl<br>        C    H    N<br>calcd.   50.16   5.21   13.93<br>found   50.75   5.10   13.76 |
| 65 | 151–153° C.<br>(2HCl salt) | 2950, 2830<br>1710, 1650<br>1600, 1450<br>1270, 1130<br>1030, 780<br>740 | 1.52–1.79(m, 4H), 2.38(s,<br>3H), 2.44(t, 2H, J=7.3Hz),<br>2.56(t, 4H, J=4.6Hz), 3.55<br>(t, 4H, J=4.6Hz), 4.00(t,<br>2H, J=7.3Hz), 4.72(s, 2H),<br>6.58–6.65(m, 2H), 6.89(s,<br>1H), 7.04(d, 1H, J=7.6Hz),<br>7.47(m, 1H), 8.06(d, 1H, J=<br>7.6Hz), 8.18(dd, 1H, J=<br>1.3Hz, 4.6Hz) | 2HCl.2H$_2$O<br>        C    H    N<br>calcd.   53.38   6.62   10.83<br>found   53.66   6.05   10.83 |
| 66 | 163–165° C.<br>(2HCl salt) | 2940, 2810<br>1710, 1650<br>1620, 1580<br>1440, 1290<br>1240, 1140<br>1030, 850<br>760 | 1.52–1.74(m, 4H), 2.38(s,<br>3H), 2.44(t, 2H, J=7.3Hz),<br>2.60(t, 4H, J=4.6Hz), 3.38<br>(t, 4H, J=4.6Hz), 4.00(t,<br>2H, J=7.3Hz), 4.72(s, 2H),<br>6.81(dd, 1H, J=4.6Hz),<br>7.3Hz), 6.89(s, 1H), 7.03(d,<br>1H, J=7.9Hz), 7.56(dd, 1H,<br>J=1.3Hz, 7.3Hz), 8.06(d, 1H,<br>J=7.9Hz), 8.17(dd, 1H,<br>J=1.3Hz, 4.6Hz) | 2HCl.1/2H$_2$O<br>        C    H    N<br>calcd.   53.03   5.71   10.76<br>found   52.95   5.79   10.76 |
| 67 | 183–185° C.<br>(HCl salt) | 2950, 2820<br>1710, 1650<br>1600, 1560<br>1510, 1240<br>1140, 1040<br>950, 860<br>760 | 1.49–1.74(m, 4H), 2.39(s,<br>3H), 2.42(t, 2H, J=7.3Hz),<br>2.52(t, 4H, J=5.3Hz), 3.46<br>(t, 4H, J=5.3Hz), 3.99(t,<br>2H, J=7.3Hz), 4.72(s, 2H),<br>6.72(dd, 1H, J=4.6Hz,<br>7.9Hz), 6.89(s, 1H), 7.04(d<br>1H, J=7.9Hz), 8.06(d, 1H,<br>J=7.9Hz), 8.10(dd, 1H, J=<br>1.3Hz, 7.9Hz), 8.31(dd, 1H,<br>J=1.3Hz, 4.6Hz) | HCl.H$_2$O<br>        C    H    N<br>calcd.   54.38   5.95   13.79<br>found   54.25   5.94   13.66 |
| 68 | 117–123° C.<br>(2HCl salt) | 2930, 2810<br>2210, 1700<br>1650, 1580<br>1550, 1440<br>1230, 1140<br>1040, 940<br>760 | 1.51–1.74(m, 4H), 2.39(s,<br>3H), 2.43(t, 2H, J=7.3Hz),<br>2.57(t, 4H, J=5.3Hz), 3.74<br>(t, 4H, J=5.3Hz), 4.00(t,<br>2H, J=7.3Hz), 4.72(s, 2H),<br>6.72(dd, 1H, J=4.6Hz),<br>7.3Hz), 6.89(s, 1H), 7.04(d,<br>1H, J=7.9Hz), 7.54(dd, 1H,<br>J=1.9Hz, 7.3Hz), 8.06(d,<br>1H, J=7.9Hz), 8.33(dd, 1H,<br>J=1.9Hz, 4.6Hz) | 2HCl.H$_2$O<br>        C    H    N<br>calcd.   54.69   5.96   13.35<br>found   55.19   5.61   13.32 |
| 69 | 131–135° C.<br>(2HCl salt) | 3500–3300<br>2950, 2820<br>1710, 1650<br>1620, 1460<br>1290, 1240<br>1140, 1040<br>770 | 1.52–1.75(m, 4H), 2.39(s,<br>3H), 2.44(t, 2H, J=7.3Hz),<br>2.60(b.s. 4H), 3.14(t, 4H,<br>J=4.6Hz), 3.75(s, 2H), 4.00<br>(t, 2H, J=7.3Hz), 4.72(s,<br>2H), 6.81(dd, 1H, J=4.6Hz,<br>7.9Hz), 6.89–6.95(m, 2H),<br>7.04(d, 1H, J=7.3Hz), 7.79<br>(dd, 1H, J=1.9Hz, 4.6Hz),<br>8.06(d, 1H, J=7.3Hz) | 2HCl.1/2H$_2$O<br>        C    H    N<br>calcd.   54.66   6.38   13.86<br>found   54.21   6.22   13.69 |
| 70 | 164–166° C.<br>(2HCl salt) | 2960, 2825<br>1710, 1650<br>1620, 1580<br>1550, 1480<br>1450, 1360<br>1140, 800<br>740 | 1.51–1.75(m, 4H), 2.39(s,<br>3H), 2.38–2.60(m, 6H), 3.84<br>(b.s., 4H), 4.00(t, 2H, J=<br>7.3Hz), 4.72(s, 2H), 6.48(t,<br>1H, J=4.6Hz), 6.89(s, 1H),<br>7.04(d, 1H, J=7.9Hz), 8.06<br>(d, 1H, J=7.9Hz), 8.30(d,<br>2H, 4.6Hz) | 2HCl.1/2H$_2$O<br>        C    H    N<br>calcd.   53.77   6.15   14.25<br>found   53.31   5.90   14.10 |
| 71 | 184.5–185.0° C.<br>(2HCl salt) | 2930, 2800<br>1700, 1640 | 1.52–1.74(m, 4H), 2.41(t,<br>2H, J=7.3Hz), 2.54(t, 4H, | 2HCl.1/2H$_2$O<br>        C    H    N |

-continued

| # | mp | IR | NMR | Formula / Analysis |
|---|---|---|---|---|
| | | 1600, 1480<br>1430, 1270<br>1225, 1160<br>1130, 1020<br>1075, 975<br>930, 770<br>725 | J=5.3Hz), 3.53(t, 4H, J=<br>5.3Hz), 3.85(s, 3H), 3.98(t,<br>2H, J=7.3Hz), 4.72(s, 2H),<br>6.53(d, 1H, J=2.0Hz), 6.58–<br>6.64(m, 2H), 6.76(dd, 1H,<br>J=2.0Hz&8.6Hz), 7.46(dt,<br>1H, J=2.0Hz&7.9Hz), 8.14<br>(d, 1H, J=8.6Hz), 8.18(dd,<br>1H, J=2.0Hz&5.9Hz) | calcd.  54.54  6.17  11.06<br>found  54.12  6.01  10.85 |
| 72 | 179–182° C.<br>(2HCl salt) | 2930, 2800<br>1700, 1640<br>1605, 1580<br>1540, 1490<br>1445, 1360<br>1270, 1225<br>1130, 980<br>840, 790<br>760, 725 | 1.52–1.74(m, 4H), 2.40(t,<br>2H, J=7.3Hz), 2.48(t, 4H,<br>J=4.9Hz), 3.81(t, 4H, J=<br>4.9Hz), 3.86(s, 3H), 3.99(t,<br>2H, J=7.3Hz), 4.73(s, 2H),<br>6.46(t, 1H, J=4.6Hz), 6.54<br>(d, 1H, J=2.6Hz),<br>6.77(dd, 1H, J=2.6Hz&<br>9.2Hz), 8.14(d, 1H, J=<br>9.2Hz), 8.29(d, 2H, J=<br>4.6Hz) | 2HCl<br>        C     H     N<br>calcd.  53.01  5.87  14.05<br>found  52.78  5.83  13.94 |
| 73 | Hygroscopic<br>(2HCl salt) | 2930, 2810<br>1710, 1660<br>1600, 1480<br>1435, 1310<br>1270, 1240<br>1100, 1050<br>980, 940<br>805, 775<br>730, 705 | 1.54–1.78(m, 4H), 2.44(t,<br>2H, J=7.3Hz), 2.56(t, 4H,<br>J=5.3Hz), 3.55(t, 4H, J=<br>5.3Hz), 3.88(s, 3H), 4.03(t,<br>2H, J=7.3Hz), 4.71(s, 2H),<br>6.59–6.66(m, 2H), 6.69(d,<br>1H, J=8.6Hz), 6.81(d, 1H,<br>J=8.6Hz), 7.39(t, 1H, J=<br>8.6Hz), 7.47(dt, 1H, J=<br>2.0Hz&7.3Hz), 8.18(dd, 1H,<br>J=2.0Hz&5.3Hz) | 2HCl.5/2H$_2$O<br>        C     H     N<br>calcd.  50.92  6.50  10.33<br>found  50.79  6.34  10.00 |
| 74 | 180–182° C.<br>(HCl salt) | 2940, 2840<br>1700, 1660<br>1600, 1580<br>1540, 1470<br>1440, 1355<br>1245, 1095<br>980, 810<br>790, 770<br>720, 680 | 1.51–1.72(m, 4H), 2.43(t,<br>2H, J=7.3Hz), 2.50(t, 4H,<br>J=5.3Hz), 3.83(t, 4H, J=<br>5.3Hz), 3.88(s, 3H), 4.03(t,<br>2H, J=7.3Hz), 4.71(s, 2H),<br>6.47(t, 1H, J=4.6Hz), 6.69<br>(d, 1H, J=7.9Hz), 6.80(d,<br>1H, J=7.9Hz), 7.39(t, 1H,<br>J=7.9Hz), 8.30(d, 2H, J=<br>4.6Hz) | 1HCl.5/2H$_2$O<br>        C     H     N<br>calcd.  52.12  6.56  13.81<br>found  51.92  6.47  13.23 |
| 75 | 58–62° C.<br>(maleic acid<br>salt) | 2930, 2800<br>1705, 1660<br>1590, 1470<br>1430, 1305<br>1270, 1240<br>1155, 1090<br>1040, 975<br>805, 770<br>730, 690 | 1.54–1.76(m, 4H), 2.37(t,<br>2H, J=7.3Hz), 2.52(t, 4H,<br>J=4.9Hz), 3.52(t, 4H, J=<br>4.9Hz), 4.04(t, 2H, J=<br>7.3Hz), 4.72(s, 2H), 5.17(s,<br>2H), 6.58–6.64(m, 2H), 6.70<br>(d, 1H, J=8.6Hz), 6.84(d,<br>1H, J=8.6Hz), 7.27–7.50<br>(m, 7H), 8.18(dd, 1H, J=<br>1.6Hz&4.3Hz) | CHCOOH<br>‖      .1/2H$_2$O<br>CHCOOH<br>        C     h     N<br>calcd.  63.14  5.94  8.92<br>found  62.80  5.84  8.74 |
| 76 | 58–62° C.<br>(maleic acid<br>salt) | 2920, 2800<br>1705, 1660<br>1600, 1580<br>1540, 1445<br>1355, 1250<br>1095, 1040<br>980, 950<br>800, 755<br>730, 705<br>690 | 1.54–1.74(m, 4H), 2.36(t,<br>2H, J=7.3Hz), 2.46(t, 4H,<br>J=5.3Hz), 3.80(t, 4H, J=<br>5.3Hz), 4.04(t, 2H, J=<br>7.3Hz), 4.72(s, 2H), 5.17(s,<br>2H), 6.47(t, 1H, J=4.6Hz),<br>6.70(d, 1H, J=8.6Hz), 6.84<br>(d, 1H, J=8.6Hz), 7.27–<br>7.46(m, 6H), 8.29(d, 2H, J=<br>4.6Hz) | CHCOOH<br>‖      .H$_2$O<br>CHCOOH<br>        C     H     N<br>calcd.  60.46  5.87  11.01<br>found  60.62  5.87  10.74 |
| 77 | 199–202° C.<br>(2HCl salt) | 3450, 2950<br>2800, 1705<br>1630, 1590<br>1480, 1450<br>1435, 1350<br>1310, 1240<br>1195, 1150<br>1065, 980<br>810, 770<br>730, 700 | 1.56–1.76(m, 4H), 2.43(t,<br>2H, J=7.6Hz), 2.55(t, 4H,<br>J=5.3Hz), 3.54(t, 4H, J=<br>5.3Hz), 4.01(t, 2H, J=<br>7.6Hz), 4.70(s, 2H), 6.57–<br>6.79(m, 3H), 6.80(d, 1H, J=<br>8.1Hz), 7.38(t, 1H, J=<br>8.1Hz), 7.47(dt, 1H, J=<br>1.7Hz&7.3Hz), 8.18(dd, 1H,<br>J=1.7Hz&5.1Hz), 12.29<br>(br.s, 1H) | 2HCl.1/4H$_2$O<br>        C     H     N<br>calcd.  54.16  5.89  11.48<br>found  54.07  5.78  11.47 |
| 78 | 197–198° C.<br>(2HCl salt) | 2930, 2750<br>1700, 1630<br>1580, 1540<br>1445, 1355<br>1305, 1255<br>1210, 1180<br>1060, 980<br>805, 790 | 1.55–1.78(m, 4H), 2.43(t,<br>2H, J=7.6Hz), 2.51(t, 4H,<br>J=5.3Hz), 3.83(t, 4H, J=<br>5.3Hz), 4.01(t, 2H, J=<br>7.6Hz), 4.70(s, 2H), 6.48(t,<br>1H, J=4.9Hz), 6.59(d, 1H,<br>J=7.9Hz), 6.80(d, 1H, J=<br>7.9Hz), 7.38(t, 1H, H=<br>7.9Hz), 8.30(d, 2H, J=<br>4.9Hz), 12.29(br.s, 1H) | 2HCl<br>        C     H     N<br>calcd.  52.07  5.62  14.46<br>found  52.08  5.59  14.39 |

-continued

| | | | | |
|---|---|---|---|---|
| 79 | 68–72° C. (maleic acid salt) | 2920, 2750 1730, 1690 1670, 1610 1590, 1480 1430, 1340 1300, 1240 1200, 1120 1100, 1170 1120, 770 | 1.52–1.79(m, 4H), 2.38(t, 2H, J=7.3Hz), 2.51(t, 4H, J=4.9Hz), 3.52(t, 4H, J=4.9Hz), 4.00–4.12(m, 2H), 4.71(s, 2H), 6.60–6.68(m, 2H), 7.44–7.54(m, 2H), 8.17–8.20(m, 1H), 8.45(dd, 1H, J=2.6Hz&9.2Hz), 8.76(d, 1H, J=2.6Hz) | CHCOOH ‖ .H$_2$O CHCOOH<br><br>    C    H    N<br>calcd. 54.45 5.45 12.21<br>found 54.59 5.15 11.97 |
| 80 | 175–178° C. (maleic acid salt) | 2920, 2750 1730, 1685 1605, 1580 1480, 1430 1340, 1253 1200, 1120 980, 790 770 | 1.51–1.79(m, 4H), 2.37(t, 2H, J=7.3Hz), 2.45(t, 4H, J=5.3Hz), 3.81(t, 4H, J=5.3Hz), 4.03–4.07(m, 2H), 4.71(s, 2H), 6.48(t, 1H, J=4.6Hz), 7.53(d, 1H, J=9.2Hz), 8.30(d, 2H, J=4.6Hz), 8.45(dd, 1H, J=2.6Hz&9.2Hz), 8.76(d, 1H, J=2.6Hz) | CHCOOH ‖ .H$_2$O CHCOOH<br><br>    C    H    N<br>calcd. 53.95 5.07 15.10<br>found 53.63 5.04 14.83 |
| 81 | 71–75° C. (citric acid salt) | 2930, 2800 1710, 1650 1590, 1480 1430, 1380 1360, 1305 1270, 1245 1150, 1110 1040, 975 930, 840 765, 725 | 1.55–1.78(m, 4H), 2.44(t, 2H, J=7.3Hz), 2.56(t, 4H, J=5.3Hz), 3.55(t, 4H, J=5.3Hz), 3.95(s, 3H), 4.04(t, 2H, J=7.3Hz), 4.80(s, 2H), 6.60–6.67(m, 2H, 7.17(d, 1H, J=8.6Hz), 7.45–7.51 (m, 1H), 8.15–8.21(m, 2H), 8.91(d, 1H, J=2.6Hz) | CH$_2$COOH<br>\|<br>HOCCOOH  .3/2H$_2$O<br>\|<br>CH$_2$COOH<br><br>    C    H    N<br>calcd. 53.64 5.85 8.34<br>found 53.33 5.47 7.99 |
| 82 | 134–135° C. (maleic acid salt) | 2930, 2800 1710, 1650 1600, 1580 1540, 1480 1435, 1350 1245, 1110 1040, 980 840, 790 765 | 1.50–1.74(m, 4H), 2.41(t, 2H, J=7.3Hz), 2.49(t, 4H, J=4.9Hz), 3.82(t, 4H, J=4.9Hz), 3.94(s, 3H), 4.02(t, 2H, J=7.3Hz), 4.78(s, 2H), 6.47(t, 1H, J=4.6Hz), 7.15 (d, 1H, J=8.6Hz), 8.17(dd, 1H, J=2.0Hz&8.6Hz), 8.30 (d, 2H, J=4.6Hz), 8.90(d, 1H, J=2.0Hz) | CHCOOH<br>‖<br>CHCOOH<br><br>    C    H    N<br>calcd. 56.93 5.49 12.30<br>found 56.74 5.48 12.13 |
| 83 | 154–156° C. (2HCl salt) | 2940, 2850 1710, 1650 1580, 1460 1300, 1130 1030, 990 790, 770 | 1.53–1.76(m, 4H), 2.42(t, 2H, J=7.3Hz), 2.49(t, 4H, J=5.3Hz), 3.81(t, 4H, J=5.3Hz), 3.88(s, 3H), 4.02(t, 2H, J=7.3Hz), 4.75(s, 2H), 5.96(d, 1H, J=5.3Hz), 7.09 (dd, 1H, J=1.3Hz, 7.9Hz), 7.24(m, 1H), 7.52(m, 1H), 8.04(d, 1H, J=5.3Hz), 8.16 (dd, 1H, J=1.9Hz, 7.9Hz) | 2HCl.3/2H$_2$O<br>    C    H    N<br>calcd. 50.29 6.14 13.33<br>found 50.30 5.54 13.29 |
| 84 | 138–145° C. (2HCl salt) | 1700, 1650 1600, 1540 1340, 1300 1220, 1120 1080, 960 790, 770 | 1.51–1.76(m, 4H), 2.41(t, 2H, J=7.3Hz), 2.48(t, 4H, J=5.3Hz), 3.64(t, 4H, J=5.3Hz), 3.92(s, 3H), 4.01(t, 2H, J=7.3Hz), 4.76(s, 2H), 6.15(d, 1H, J=5.9Hz), 7.09 (dd, 1H, J=1.3Hz, 7.9Hz), 7.24(m, 1H), 7.52(m, 1H), 8.01(d, 1H, J=5.9Hz), 8.16 (dd, 1H, J=1.3Hz, 7.9Hz) | 2HCl.3/2H$_2$O<br>    C    H    N<br>calcd. 50.29 6.14 13.33<br>found 50.09 6.02 13.63 |
| 85 | 199–201° C. (HCl salt) | 2950, 1700 1650, 1600 1520, 1480 1430, 1290 1120, 990 920, 820 780, 760 | 1.50–1.74(m, 4H), 2.43(t, 2H, J=7.3Hz), 2.55(t, 4H, J=4.6Hz), 3.58(t, 4H, J=4.6Hz), 3.99(t, 2H, J=7.3Hz), 4.76(s, 2H), 7.10(d, 1H, J=7.9Hz), 7.24(m, 1H), 7.52(m, 1H), 7.84(d, 1H, J=2.6Hz), 8.05(d, 1H, J=2.6Hz), 8.12(s, 1H), 8.16(d, 1H, J=7.9Hz) | HCl<br>    C    H    N<br>calcd. 58.39 6.06 16.21<br>found 57.88 6.07 15.87 |
| 86 | 173–175° C. (HCl salt) | 2950, 2810 1710, 1660 1610, 1570 1480, 1300 1140, 1040 890, 820 770, 740 | 1.51–1.76(m, 4H), 2.43(t, 2H, J=7.3Hz), 2.52(t, 4H, J=5.3Hz), 3.60(t, 4H, J=5.3Hz), 4.02(t, 2H, J=7.3Hz), 4.76(s, 2H), 7.10 (dd, 1H, J=1.3Hz, 7.9Hz), 7.24(m, 1H), 7.51(m, 1H), 7.80(s, 1H), 7.95(s, 1H), 8.16(dd, 1H, J=1.3Hz, 7.9Hz) | HCl.H$_2$O<br>    C    H    N<br>calcd. 51.96 5.61 14.43<br>found 51.66 5.35 14.25 |
| 87 | 152–155° C. (2HCl salt) | 2950, 2820 1710, 1650 1600, 1570 | 1.52–1.76(m, 4H), 2.43(t, 2H, J=7.3Hz), 2.54(t, 4H, J=5.3Hz), 3.56(t, 4H, J= | 2HCl<br>    C    H    N<br>calcd. 53.02 5.86 14.05 |

-continued

| | | | | | | | |
|---|---|---|---|---|---|---|---|
| | | 1540, 1490<br>1450, 1290<br>1190, 990<br>910, 820<br>730 | 5.3Hz), 3.89(s, 3H), 4.02(t,<br>2H, J=7.3Hz), 4.76(s, 2H),<br>7.09(dd, 1H, J=1.3Hz,<br>7.3Hz), 7.24(m, 1H), 7.51(s,<br>1H), 7.52(m, 1H), 7.62(s,<br>1H), 8.16(dd, 1H, J=1.9Hz,<br>7.9Hz) | found | 52.95 | 5.87 | 13.89 |
| 88 | 176–177° C.<br>(2HCl salt) | 2930, 2800<br>1705, 1650<br>1600, 1595<br>1480, 1435<br>1360, 1305<br>1240, 1155<br>1120, 1040<br>980, 765<br>725 | 1.39(quintett, 2H, J=<br>7.6Hz), 1.59(quintett, 2H,<br>J=7.6Hz), 1.69(quintett, 2H,<br>J=7.6Hz), 2.39(t, 2H, J=<br>7.6Hz), 2.55(t, 4H, J=<br>4.9Hz), 3.55(t, 4H, J=<br>4.9Hz), 3.98(t, 2H, J=<br>7.6Hz), 4.75(s, 2H), 6.59–<br>6.66(m, 2H), 7.09(d, 1H, J=<br>7.9Hz), 7.24(t, 1H, J=<br>7.9Hz), 7.44–7.54(m, 2H),<br>8.15–8.19(m, 2H) | 2HCl.1H$_2$O<br>calcd.<br>found | C<br>55.31<br>54.77 | H<br>6.46<br>5.87 | N<br>11.21<br>11.10 |
| 89 | 160–161° C.<br>(1HCl salt) | 2930, 2840<br>1700, 1650<br>1580, 1540<br>1480, 1445<br>1360, 1300<br>1255, 1215<br>1120, 980<br>795, 760 | 1.39(quintett, 2H, J=<br>7.6Hz), 1.59(quintett, 2H,<br>J=7.6Hz), 1.69(quintett, 2H,<br>J=7.6Hz), 2.38(t, 2H, J=<br>7.6Hz), 2.49(t, 4H, J=<br>4.9Hz), 3.83(t, 4H, J=<br>4.9Hz), 3.98(t, 2H, J=<br>7.6Hz), 4.75(s, 2H), 6.47(t,<br>1H, J=4.6Hz), 7.09)d, 1H,<br>J=7.9Hz), 7.24(t, 1H, J=<br>7.9Hz), 7.51(dt, 1H, J=<br>1.6Hz&7.9Hz), 8.16(dd, 1H,<br>J=1.6Hz&7.9Hz), 8.30(d,<br>2H, J=4.6Hz) | 1HCl.1/4H$_2$O<br>calcd.<br>found | C<br>58.65<br>58.70 | H<br>6.38<br>6.29 | N<br>15.55<br>15.56 |
| 90 | 175–178° C.<br>(2HCl salt) | 2940, 2840<br>1710, 1650<br>1590, 1500<br>1290, 1030<br>780, 730 | 1.41(m, 2H), 1.55–1.74(m,<br>4H), 2.41(t, 2H, J=7.3Hz),<br>2.57(t, 4H, J=4.6Hz), 3.56<br>(t, 4H, J=4.6Hz), 3.83(s,<br>3H), 3.99(t, 4H, J=7.3Hz),<br>4.71(s, 2H), 6.59–6.65(m,<br>2H), 6.69–7.09(m, 2H), 7.47<br>(m, 1H), 7.58(d, 1H, J=<br>2.6Hz), 8.18(dd, 1H, J=<br>1.3Hz, 5.3Hz) | 2HCl 1/4H$_2$O<br>calcd.<br>found | C<br>55.86<br>55.88 | H<br>6.35<br>6.09 | N<br>10.86<br>10.89 |
| 91 | 152–155° C.<br>(2HCl salt) | 2940, 1700<br>1650, 1600<br>1510, 1290<br>1060, 1030<br>960, 800 | 1.40(m, 2H), 1.54–1.74(m,<br>4H), 2.40(t, 2H, J=7.3Hz),<br>2.51(t, 4H, J=4.6Hz), 3.83<br>(t, 4H, J=4.6Hz), 3.84(s,<br>3H), 3.98(t, 2H, J=7.3Hz),<br>4.72(s, 2H), 6.47(t, 1H, J=<br>4.6Hz), 6.99–7.09(m, 2H),<br>7.58(d, 1H, J=2.6Hz), 8.30<br>(d, 2H, J=4.6Hz) | 2HCl<br>calcd.<br>found | C<br>53.91<br>54.10 | H<br>6.10<br>6.02 | N<br>13.67<br>13.77 |
| 92 | 147–150° C.<br>(2HCl salt) | 2940, 2810<br>1700, 1650<br>1620, 1590<br>1480, 1410<br>1370, 1250<br>1140, 980<br>770 | 1.39(m, 2H), 1.52–1.73(m,<br>4H), 2.36(t, 2H, J=7.3Hz),<br>2.37(s, 3H), 2.53(t, 4H, J=<br>5.3Hz), 3.53(t, 4H, J=<br>5.3Hz), 3.97(t, 2H, J=<br>7.3Hz), 4.72(s, 2H), 6.58–<br>6.65(m, 2H), 6.88(s, 1H),<br>7.03(d, 1H, J=7.9Hz), 7.46<br>(m, 1H), 8.05(d, 1H, J=<br>7.9Hz), 8.18(dd, 1H, J=<br>1.3Hz, 7.3Hz) | 2HCl.3/2H$_2$O<br>calcd.<br>found | C<br>55.17<br>54.96 | H<br>6.75<br>6.51 | N<br>10.72<br>10.72 |
| 93 | 167–169° C.<br>(2HCl salt) | 2940, 1700<br>1650, 1590<br>1460, 1360<br>1300, 1140<br>980, 830<br>800 | 1.39(m, 2H), 1.52–1.73(m,<br>4H), 2.36(t, 2H, J=7.3Hz),<br>2.38(s, 3H), 2.48(t, 4H, J=<br>5.3Hz), 3.82(t, 4H, J=<br>5.3Hz), 3.97(t, 2H, J=<br>7.3Hz), 4.72(s, 2H), 6.47(t,<br>1H, J=5.3Hz), 6.89(s, 1H),<br>7.04(d, 1H, J=7.9Hz), 8.06<br>(d, 1H, J=7.9Hz), 8.29(d,<br>2H, J=5.3Hz) | 2HCl 1/2H$_2$O<br>calcd.<br>found | C<br>54.65<br>54.79 | H<br>6.38<br>6.62 | N<br>13.86<br>13.90 |
| 94 | oily product | 3330–3000<br>1700, 1650<br>1600, 1490<br>1410, 1360<br>1290, 1200<br>1110, 920<br>710 | 1.54–1.77(m, 4H)<br>2.23(S, 3H), 2.47(t, 2H,<br>J=7.3Hz), 2.62(m, 4H), 3.07<br>(m, 4H) 4.02(t, 2H,<br>J=7.3Hz) 4.76(S, 2H)<br>7.02(dd, 1H, J=4.6Hz,<br>7.9Hz) 7.10(d, 1H, J=7.3Hz)<br>7.24(m, 1H) 7.52(m, 1H)<br>7.91(brs, 1H), 8.07(dd, | | | | |

| |
|---|
| 1H, J=1.3Hz, 4.6Hz) 8.16 (dd, m, J=7.3Hz) J=1.3Hz, 7.9Hz) 8.53(dd, 1H, J=1.3Hz, 7.9Hz) |

The compound of the present invention exhibits a high affinity for a serotonin receptor and an anticonflict activity and is useful as a psychotropic agent against an anxiety neurosis, phobic disorder, and obsessive-compulsive disorder, etc. The pharmocological test results are described below.

Affinity for Serotonin Receptor

Test Method

The test was conducted according to the method of S. T. Perouka (J. Neurochem., 47, 529-540 (1986)).

To the cerebral cortex enucleated from a Wistarstrain male rat was added 50 mM Tris-HCl (pH 7.7) buffer and the mixture was homogenized by using Polytron®. The homogenate was centrifuged at 40,000 G for 10 minutes, and to the obtained precipitate was added the same buffer to effect homogenization, followed by incubation at 37° C. for 30 minutes. The suspension was centrifuged again at 40,000 G for 10 minutes, and to the obtained precipitate was added the same buffer to effect homogenization, followed by centrifugation at 40,000 G for 10 minutes. To the final obtained precipitate was added 50 mM Tris-HCl (10 μm pargyline, 4 mM CaCl$_2$, 0.1% ascorbic acid) (pH 7.4) buffer, to effect homogenization, and the homogenate was used for the binding test. The ($^3$H) 8-OH-DPAT used for the binding test was 0.4 nM, with a protein amount of 0.4 to 0.6 mg/ml, and a total amount of 1 ml. After incubation at 25° C. for 30 minutes, the mixture was filtered by a filtration method using a Whatman GF/B filter, and the filter was washed three times with 5 ml of the same buffer.

To the filter was added a scintillation cocktail, and a measurement was conducted by a liquid scintillation counter.

Results

As a result of the above test, all the compounds of Examples according to the present invention were found to have a strong affinity at a dose of a μM order or less. Among them, the following compounds have extremely strong affinity at nM order (see Table 3).

TABLE 3

| Compound (Example No.) | [$^3$H]8-OH-DPAT IC$_{50}$ (nM) |
|---|---|
| 27 | 6.15 |
| 30 | 2.62 |
| 36 | 2.31 |
| 39 | 1.41 |
| 43 | 2.48 |
| 48 | 2.77 |
| 52 | 3.75 |
| 54 | 4.91 |
| 58 | 5.02 |
| 59 | 1.78 |
| 64 | 4.10 |
| 65 | 1.55 |
| 70 | 4.75 |
| 72 | 4.26 |
| 83 | 4.16 |

We claim:

1. A compound having the formula:

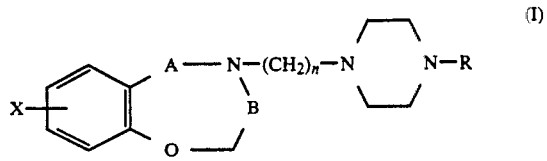

wherein A and B are both carbonyl groups, or one thereof represents a methylene group and the other a carbonyl group, R represents A C$_6$-C$_{20}$ aromatic group or a 5 to 7 membered heterocyclic group selected from the group consisting of a pyridine ring, a pyrimidinyl ring, a pyrazinyl ring, imidazolyl ring and pyridazinyl ring which may be substituted with at least one group selected from the group consisting of halogen atoms, a hydroxyl group, C$_1$-C$_6$ lower alkyl groups, C$_1$-C$_5$ alkoxy groups, C$_7$-C$_9$ arylalkoxy groups, a cyano group, a nitro group, an amino group, an amido group, a trifluoromethyl group, and an ester group, X represents a hydrogen atom, a halogen atom, a C$_1$-C$_5$ lower alkyl group, a C$_1$-C$_5$ lower alkoxy group, a C$_7$-C$_{11}$ arylalkoxy group, a hydroxyl group, a nitro group, or a C$_1$-C$_5$ lower alkyl ester group, and n is an integer of 2 to 10 and pharmaceutically acceptable salts thereof.

2. A compound as claimed in claim 1, wherein A represents a carbonyl group and B represents a carbonyl group or a methylene group.

3. A compound as claimed in claim 1, wherein R represents a 5-7 membered heterocyclic group selected from the group consisting of a pyridine ring, a pyrimidinyl ring, pyrazinyl ring, imidazolyl ring and pyridazinyl ring or a C$_6$-C$_{10}$ aromatic group, which may be substituted with at least one group selected from the group consisting of halogen atoms, a hydroxyl gruop, C$_1$-C$_6$ lower alkyl groups, C$_1$-C$_5$ alkoxy groups, C$_7$-C$_9$ arylalkoxy groups, a cyano group, a nitro group, an amino group, an amido group, a trifluoromethyl group, and an ester group.

4. A compound as claimed in claim 2, wherein the heterocyclic group is selected from the group consisting of pyridyl, pyrimidinyl, pyrazinyl, pyridazinyl, and imidazolyl and the aromatic ring is phenyl or naphthyl, which may be substituted.

5. A compound having the formula:

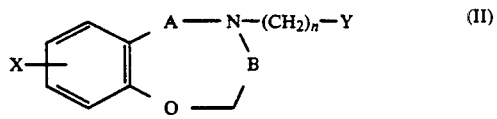

wherein A and B are both carbonyl groups, or one thereof represents a methylene group and the other a carbonyl group, X represents a hydrogen atom, a halogen atom, a C$_1$-C$_5$ lower alkyl group, a C$_1$-C$_5$ lower alkoxy group, a C$_7$-C$_{11}$ arylalkoxy group, a hydroxyl group, a cyano group, a nitro group or a C$_1$-C$_5$ lower alkyl ester group, Y represents a halogen atom, and n is an integer of 2 to 10, and salts thereof.

6. A compound as claimed in claim 5, wherein A represents a carbonyl group and B represents a carbonyl group or a methylene group.

7. A compound as claimed in claim 5, wherein Y represents bromine or chlorine.

8. A psychotropic composition comprising a compound according to claim 1 or a pharmaceutically acceptable salt thereof in an amount sufficient to treat psychotic disorders, as an active ingredient, and a carrier thereof.

9. An antianxiety pharmaceutical composition of claim 8.

10. A pharmaceutical composition for diseases related to serotonerigic ceuron system comprising a compound according to claim 1 or a pharmacologically acceptable salt thereof, as an active ingredient in an amount sufficient to treat psychotic disorders, and a carrier therefor.

11. A psychotropic composition according to claim 8, wherein A represents a carbonyl group and B represents a carbonyl group or a methylene group.

12. A pharmaceutical composition for diseases related to the serotonergic nervous system according to claim 10, wherein A represents a carbonyl group and B represents a carbonyl group or a methylene group.

13. A method for treating a disease relating to the serotonergic nervous system, comprising administering an effective amount to treat the serotonergic nervous system of a compound having the formula:

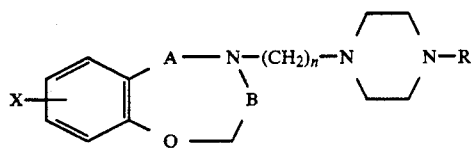

wherein A and B are both carbonyl groups, or one thereof represents a methylene group and the other a carbonyl group, R represents a $C_6$–$C_{20}$ aromatic group or a 5 to 7 membered heterocyclic group selected from the group consisting of a pyridine ring, a pyrimidinyl ring, pyrazinyl ring, imidazolyl ring and pyridazinyl ring which may be substituted with at least one group selected from the group consisting of halogen atoms, a hydroxyl group, $C_1$–$C_6$ lower alkyl groups, $C_1$–$C_5$ alkoxy groups, $C_7$–$C_9$ arylalkoxy groups, a cyano group, a nitro group, an amino group, an amido group, a trifluoromethyl group, and an ester group, X represents a hydrogen atom, a halogen atom, a $C_1$–$C_5$ lower alkyl group, a $C_1$–$C_5$ lower alkoxy gruop, a $C_7$–$C_{11}$ arylalkoxy group, a hydroxyl group, a nitro group, or a $C_1$–$C_5$ lower alkyl ester group, and n is an integer of 2 to 10 or a pharmaceutically acceptable salt thereof to a patient in need of such treatment.

14. A method for treating a disease relating to the serotonergic nervous system according to the method of claim 13, wherein A represents a carbonyl group and B represents a carbonyl group or a methylene group.

15. A method for treating a psychotic disorder comprising administering an effective amount to treat the psychotic disorder of a compound having the formula:

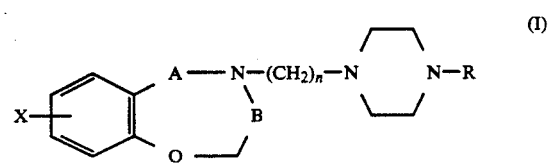

wherein A and B are both carbonyl groups, or one thereof represents a methylene group and the other a carbonyl group, R represents a $C_6$–$C_{20}$ aromatic group or a 5 to 7 membered heterocyclic group selected from the group consisting of a pyridine ring, a pyrimidinyl ring, pyrazinyl ring, imidazolyl ring and pyridazinyl ring which may be substituted with at least one group selected from the group consisting of halogen atoms, a hydroxyl group, $C_1$–$C_6$ lower alkyl groups, $C_1$–$C_5$ alkoxy groups, $C_7$–$C_9$ arylalkoxy groups, a cyano group, a nitro group, an amino group, an amido group, a trifluoromethyl group, and an ester group, X represents a hydrogen atom, a halogen atom, a $C_1$–$C_5$ lower alkyl group, a $C_1$–$C_5$ lower alkoxy group, a $C_7$–$C_{11}$ arylalkoxy group, a hydroxyl group, a nitro group, or a $C_1$–$C_5$ lower alkyl ester group, and n is an integer of 2 to 10 or a pharmaceutically acceptable salt thereof to a patient in need of such treatment.

16. A method for treating a psychotic disorder according to the method of claim 15, wherein A represents a carbonyl gruop and B represents a carbonyl group or a methylene group.

* * * * *